(12) United States Patent
Petersen

(10) Patent No.: US 10,159,692 B2
(45) Date of Patent: *Dec. 25, 2018

(54) POLYMER-CONJUGATED METAP2 INHIBITORS, AND THERAPEUTIC METHODS OF USE THEREOF

(71) Applicant: SynDevRx, Inc., Cambridge, MA (US)

(72) Inventor: John S. Petersen, Acton, MA (US)

(73) Assignee: SynDevRx, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/660,343

(22) Filed: Jul. 26, 2017

(65) Prior Publication Data

US 2018/0008630 A1 Jan. 11, 2018

Related U.S. Application Data

(63) Continuation of application No. 15/065,513, filed on Mar. 9, 2016, now Pat. No. 9,730,955, which is a continuation of application No. 13/696,743, filed as application No. PCT/US2011/037857 on May 25, 2011, now Pat. No. 9,320,805.

(60) Provisional application No. 61/347,924, filed on May 25, 2010.

(51) Int. Cl.

| | |
|---|---|
| *A61K 31/785* | (2006.01) |
| *A61K 47/58* | (2017.01) |
| *C07D 303/18* | (2006.01) |
| *C07D 405/14* | (2006.01) |
| *C07D 473/34* | (2006.01) |
| *C07K 7/06* | (2006.01) |
| *C08F 220/58* | (2006.01) |
| *A61K 31/336* | (2006.01) |
| *C07D 407/04* | (2006.01) |

(52) U.S. Cl.
CPC .......... *A61K 31/785* (2013.01); *A61K 31/336* (2013.01); *A61K 47/58* (2017.08); *C07D 303/18* (2013.01); *C07D 405/14* (2013.01); *C07D 407/04* (2013.01); *C07D 473/34* (2013.01); *C07K 7/06* (2013.01); *C08F 220/58* (2013.01)

(58) Field of Classification Search
CPC ...... A61K 31/336; A61K 47/58; A61K 47/65; A61K 31/485; A61K 31/77; A61K 38/06; A61K 47/542; A61K 31/785; A61K 47/48176; A61K 47/64; C07D 405/14; C07D 407/04; C07D 303/18; C07D 473/34; C07K 7/06; C07K 5/00; C08F 220/58

See application file for complete search history.

(56) References Cited

U.S. PATENT DOCUMENTS

| | | | |
|---|---|---|---|
| 4,997,878 A | 3/1991 | Bock et al. | |
| 5,037,883 A | 8/1991 | Kopecek et al. | |
| 5,037,957 A | 8/1991 | Grubb et al. | |
| 5,166,172 A | 11/1992 | Kishimoto et al. | |
| 5,258,453 A | 11/1993 | Kopecek et al. | |
| 5,773,522 A | 6/1998 | Angelucci et al. | |
| 6,063,812 A | 5/2000 | Hong et al. | |
| 6,291,671 B1 | 9/2001 | Inoue et al. | |
| 6,306,819 B1 | 10/2001 | Rubnick et al. | |
| 6,436,912 B1 | 8/2002 | Inoue et al. | |
| 6,464,850 B1 | 10/2002 | Zhang et al. | |
| 6,548,477 B1 | 4/2003 | Olson et al. | |
| 6,759,509 B1 | 7/2004 | King et al. | |
| 6,803,438 B1 | 10/2004 | Brocchini et al. | |
| 6,811,996 B1 | 11/2004 | Inoue et al. | |
| 6,835,807 B1 | 12/2004 | Susaki et al. | |
| 6,949,584 B2 | 9/2005 | Folkman et al. | |
| 7,041,818 B2 | 5/2006 | Susaki et al. | |
| 7,091,186 B2 | 8/2006 | Senter et al. | |
| 7,223,837 B2 | 5/2007 | De Groot et al. | |
| 7,332,523 B2 | 2/2008 | Folkman et al. | |
| 7,553,816 B2 | 6/2009 | Senter et al. | |
| 7,943,569 B2 | 5/2011 | Gemeinhart et al. | |
| 8,349,891 B2 | 1/2013 | Crawford et al. | |
| 8,367,721 B2 | 2/2013 | Huges et al. | |
| 8,399,512 B2 | 3/2013 | Akullian et al. | |
| 9,173,956 B2 * | 11/2015 | Petersen | A61K 31/336 |
| 9,320,805 B2 * | 4/2016 | Petersen | C07D 303/18 |
| 9,433,600 B2 * | 9/2016 | Petersen | A61K 31/336 |
| 9,585,909 B2 * | 3/2017 | Petersen | C07D 303/18 |
| 9,730,955 B2 * | 8/2017 | Petersen | C07D 303/18 |
| 9,750,737 B2 * | 9/2017 | Petersen | A61K 31/336 |
| 9,757,373 B2 | 9/2017 | Petersen | |
| 2002/0076442 A1 | 6/2002 | Burke et al. | |
| 2004/0001801 A1 | 1/2004 | Madison et al. | |
| 2004/0116348 A1 | 6/2004 | Chau et al. | |

(Continued)

FOREIGN PATENT DOCUMENTS

| | | |
|---|---|---|
| CA | 1305053 | 7/1992 |
| EP | 0673258 | 5/2003 |

(Continued)

OTHER PUBLICATIONS

Arico-Muendel, C.C. et al., "Carbamate Analogues of Fumagillin as Potent, Targeted Inhibitors of Methionine Aminopeptidase-2", *J. Med. Chem.*, 52:8047-8056 (2009).

(Continued)

*Primary Examiner* — Mark V Stevens
(74) *Attorney, Agent, or Firm* — Cooley LLP; Ivor R. Elrifi; Matthew Pavao

(57) ABSTRACT

One aspect of the invention provides polymer conjugated MetAP2 inhibitors. While not being bound by any particular theory, it is believed that coupling the MetAP2 inhibitory core via the linkers described herein provides compounds with superior efficacy to the parent small molecules and superior pharmacokinetic profiles. In one aspect of the invention, the polymer conjugated MetAP2 inhibitors are useful in methods of treating disease, comprising administering to a subject in need thereof a therapeutically effective amount of a polymer conjugated MetAP2 inhibitor.

2 Claims, 4 Drawing Sheets

(56) References Cited

U.S. PATENT DOCUMENTS

| | | |
|---|---|---|
| 2004/0229945 A1 | 11/2004 | Satchi-Fainaro et al. |
| 2005/0036948 A1 | 2/2005 | Kasina et al. |
| 2006/0206948 A1 | 9/2006 | Zhao |
| 2006/0276512 A1 | 12/2006 | Han et al. |
| 2007/0142302 A1 | 6/2007 | Mitra et al. |
| 2007/0287680 A1 | 12/2007 | Cuchelkar et al. |
| 2008/0112919 A1 | 5/2008 | Satchi-Fainaro et al. |
| 2008/0248030 A1 | 10/2008 | Folkman et al. |
| 2009/0093014 A1 | 4/2009 | Burnet et al. |
| 2010/0111894 A1 | 5/2010 | Benny-Ratsaby et al. |
| 2011/0263561 A1 | 10/2011 | Heinrich et al. |
| 2011/0294952 A1 | 12/2011 | Petersen |
| 2013/0064832 A1 | 3/2013 | Aikawa et al. |
| 2013/0137831 A1 | 5/2013 | Petersen |
| 2013/0216494 A1 | 8/2013 | Petersen |
| 2014/0308235 A1 | 10/2014 | Petersen et al. |
| 2015/0141580 A1 | 5/2015 | Petersen |
| 2015/0374657 A1 | 12/2015 | Petersen et al. |
| 2016/0184345 A1 | 6/2016 | Petersen |
| 2016/0256483 A1 | 9/2016 | Petersen |
| 2016/0346244 A1 | 12/2016 | Petersen et al. |
| 2017/0028014 A1 | 2/2017 | Petersen et al. |
| 2017/0196830 A1 | 7/2017 | Shanahan et al. |
| 2017/0258925 A1 | 9/2017 | Petersen |

FOREIGN PATENT DOCUMENTS

| | | | |
|---|---|---|---|
| WO | WO 2003/086382 | 10/2003 | |
| WO | WO 2004/110358 | 12/2004 | |
| WO | WO-2008011114 A2 * | 1/2008 | ............ A61K 38/05 |
| WO | WO 2009/036108 | 3/2009 | |
| WO | WO 2009/051706 | 4/2009 | |
| WO | WO 2009/073445 | 6/2009 | |
| WO | WO 2009/141826 | 11/2009 | |
| WO | WO 2010/003475 | 1/2010 | |
| WO | WO 2010/065877 | 6/2010 | |
| WO | WO 2010/096603 | 8/2010 | |
| WO | WO 2011/127304 | 10/2011 | |
| WO | WO 2011/150022 | 12/2011 | |
| WO | WO 2011/150088 | 12/2011 | |
| WO | WO 2012/122264 | 9/2012 | |

OTHER PUBLICATIONS

Bernier, S.G. et al., "Fumagillin class inhibitors of methionine aminopeptidase-2", Drugs of the Future, 30(5):497-508 (2005).
Blencowe, C.A. et al., "Self-immolative linkers in polymeric delivery systems", Polym. Chem., 2:773-790 (2011).
Chau, Y. et al., "Antitumor efficacy of a novel polymer-peptide-drug conjugate in human tumor xenograft models", Int. J. Cancer, 118:1519-1526 (2006).
D'Souza, A.J.M. et al., "Release from Polymeric Prodrugs: Linkages and Their Degradation", J. Pharm. Sci., 93(8):1962-1979 (2004).
Ducry, L. and Stump, B., "Antibody-Drug Conjugates: Linking Cytotoxic Payloads to Monoclonal Antibodies", Bioconj. Chem., 21:5-13 (2010).
Esposito et al. "The metabolic syndrome and inflammation: association or causation?" Nutr. Metab. Cardiovasc. Dis. 14(5):228-232 (2004).
Golub et al. Science, v. 286, Oct. 15, 1999, pp. 531-537.
Han, C.K. et al., "Design and synthesis of highly potent fumagillin analogues from homology modeling for a human MetAP-2", Biorg. Med. Chem. Lett., 10:39-43 (2000).
Herbst, R.S. et al., "Safety and Pharmacokinetic Effects of TNP-470, an Angiogenesis Inhibitor, Combined with Paclitaxel in Patients with Solid Tumors: Evidence for Activity in Non-Small-Cell Lung Cancer", Journal of Clinical Oncology, 20(22):4440-4447 (2002).
Hughes, T. "ZGN-201 (ZGN), a Methionine Aminopeptidase 2 (MetAP2) Inhibitor, Durably Eliminates Excess Body Fat in Obese Mice through Regulation of Fat Metabolism and Food Intake", American Diabetes Association, Sep. 20, 2010; 2 Pages, Retrieved from the internet: https://professional.diabetes.org/abstract/zgn-201-zgn-methionine-aminopeptidase-2-metap2-inhibitor-durably-eliminates-excess-body-fat.
Jeong, B-S. et al., "Total synthesis and antiangiogenic activity of cyclopentane analogues of fumagillol", Bioorganic and Medicinal Chemistry Letters, 15:3580-3583 (2005).
Joharapurkar et al. "Inhibition of the methionine aminopeptidase 2 enzyme for the treatment of obesity", Diabetes, Metabolic Syndrome and Obesity: Targets and Therapy. 2014:7; pp. 73-84 (2014).
Kahn et al. Mechanisms Linking Obesity to Insulin Resistance and type 2 diabetes. Nature, (2006) 444, p. 840-846.
Kim et al, "5-Demethoxyfumagillol, a Potent Angiogenesis Inhibitor Isolated from Aspergillus fumigatus", Chem. Pham. Bull., 52(4): 447-450 (2004).
Klok, M. D. et al., "The role of leptin and ghrelin in the regulation of food intake and body weight in humans: a review", Obesity Reviews (2007), vol. 8, pp. 21-34.
Law and Tung, "Proteolysis: A Biological Process Adapted in Drug Delivery, Therapy, and Imaging", Bioconjugate Chem., 20(9):1683-1695 (2009).
Lee, H.W. et al., "Design, Synthesis, and Antiangiogenic Effects of a Series of Potent Novel Fumagillin Analogues", Chem. Pharm. Bull., 55(7):1024-1029 (2007).
Mann-Steinberg and Satchi-Fainaro, "TNP-470: The Resurrection of the First Synthetic Angiogenesis Inhibitor", Folkman and Figg, Angiogenesis: An Integrative Approach from Science to Medicine, 35:395-414 (2008).
Mason, S. D. and Joyce, J.A. "Proteolytic networks in cancer", Trends in Cell Biology (2011); 21(4): 228-237.
Satchi-Fainaro, R. et al. "Targeting angiogenesis with a conjugate of HPMA copolymer and TNP-470", Nature Med., 10(3): 255-261 (2004).
Segal, E. et al., "Design and development of polymer conjugates as anti-angiogenic agents", Adv. Drug. Deliv. Reviews, 61(13):1159-1176 (2009).
Shiose, Y. et al., "Relationship between Drug Release of DE-310, Macromolecular Prodrug of DX-8951f, and Cathepsins Activity in Several Tumors", Biol. Pharm. Bull., 30(12):2365-2370 (2007).
Shiose, Y. et al., "Systematic Research of Peptide Spacers Controlling Drug Release from Macromolecular Prodrug System, Carboxymethyldextran Polyalcohol—Peptide—Drug Conjugates", Bioconjugate Chem., 20(1):60-70 (2009).
Subr, V. et al., "Poly[N-(2-hydroxypropyl)methacrylamide] Conjugates of Methotrexate Synthesis and in vitro Drug Release", J Controlled Release, 49:123-132 (1997).
Sutherland, J. et al. "The Metabolic Syndrome and Inflammation" Metabolic Syndrome and Related Disorders 2(2):82-104 (2004).
Bae et al., J. Diabetes and its Complications, (2016) v. 30, pp. 212-220.
Brakenhielm et al. "Angiogenesis Inhibitor, TNP-470, Prevents Diet-Induced and Genetic Obesity in Mice", Circulation Research, 2004, vol. 94, p. 1579-1588.
Kim et al. "Assessment of the anti-obesity effects of the TNP-470 analog, CKD-732", Journal of Molecular Endocrinology, 2007, vol. 38, p. 455-465.
Lijnen et al. "Fumagillin Reduces Adipose Tissue Formation in Murine Models of Nutritionally Induced Obesity", Obesity, 2010, vol. 18, No. 12, p. 2241-2246.

* cited by examiner

POLYMER-CONJUGATED METAP2 INHIBITORS, AND THERAPEUTIC METHODS OF USE THEREOF

RELATED APPLICATIONS

This application is a continuation application of U.S. patent application Ser. No. 15/065,513, filed Mar. 9, 2017, now allowed, which is a continuation of Ser. No. 13/696,743, filed Nov. 7, 2012, now U.S. Pat. No. 9,320,805, which is a 35 U.S.C. 371 NATL phase entry of PCT/US2011/037857, filed May 25, 2011, which claims the benefit of, and priority to, U.S. Provisional Patent Application Ser. No. 61/347,924, filed May 25, 2010.

BACKGROUND

Helmut Ringsdorf provided a theoretical framework for the design of polymer conjugates of small molecule drugs over thirty years ago (See Ringsdorf, "Structure and Properties of Pharmacologically Active Polymers", J. POLYMER SCI.: Symposium No. 51, 135-153 (1975)). While many conjugates have been synthesized and evaluated in animals, few have progressed to clinical trials and those trials have been largely disappointing. The identification of polymer drug conjugates that represent improvements over the parent small molecules remains an area of active research.

Fumagillin is a small molecule which has been used as an antimicrobial and antiprotozoal agent. Its physiochemical properties and method of production are well known (See U.S. Pat. No. 2,803,586 (Peterson, et al, incorporated herein by reference) and Turner, J. R. et al, The Stereochemistry of Fumagillin, Proc. Natl. Acad. Sci. 48, 733-735 (1962)). The fermentation product, fumagillin, may be hydrolyzed to yield the alcohol fumagillol which in turn may be converted into various derivatives including carbamoylfumagillol, MW 325. The synthesis and preparation of carbamoylfumagillol and some small molecule derivatives are described in U.S. Pat. No. 5,166,172.

Fumagillin and related compounds are believed to exert their biological effects through the inhibition of methionine aminopeptidase-2 (MetAP2), a metalloprotease. This enzyme removes N-terminal methionine from nascent cellular proteins. (See Tucker, L. A., et al "Ectopic Expression of Methionine Aminopeptidase-2 Causes Cell Transformation and Stimulates Proliferation", Oncogene 27, 3967 (2008).)

Carbamoylfumagillol and derivatives as well as other inhibitors of MetAP2 have shown therapeutic benefits in preclinical and clinical studies. These compounds inhibit cell proliferation and angiogenesis as described in U.S. Pat. No. 5,166,172 (Kishimoto, et al, incorporated herein by reference). One of these derivatives, chloroacetylcarbamoylfumagillol (TNP-470) has been extensively studied. (See H. Mann-Steinberg, et al., "TNP-470: The Resurrection of the First Synthetic Angiogenesis Inhibitor", Chapter 35 in Folkman and Figg, Angiogenesis: An Integrative Approach from Science to Medicine, Springer NY (2008).) TNP-470 has shown activity against many cancers, including lung cancer, cervical cancer, ovarian cancer, breast cancer, and colon cancer. Because of dose-limiting neurotoxicity, TNP-470 has been tested using multiple dosing regimens, but these attempts to limit its toxicity have been unsuccessful. Thus, TNP-470 has been found to be too toxic for human use. With few exceptions, unacceptable weight loss or failure to gain weight was observed in animals receiving TNP-470. TNP-470 has a short half-life and requires extended intravenous administration for therapeutic use. A metabolite of TNP-470, carbamoylfumagillol has a half-life of 12 minutes in man. (See Herbst et al., "Safety and Pharmacokinetic Effects of TNP-470, an Angiogenesis Inhibitor, Combined with Paclitaxel in Patients with Solid Tumors: Evidence for Activity in Non-Small-Cell Lung Cancer", Journal of Clinical Oncology 20(22) 4440-4447 (2002). In addition, fumagillin and its derivatives are hydrophobic and difficult to formulate.

Methionine aminopeptidase-2 (MetAP2), a metalloprotease, is an enzyme that processes N-terminal methionine from nascent cellular proteins. Inhibition of MetAP2 has been shown to block angiogenesis and suppress tumor growth in preclinical tumor models. Interestingly, fumagillin, chloroacetylcarbamoylfumagillol, carbamoylfumagillol and related compounds have been shown to be inhibitors of MetAP2. (See Tucker, L. A., et al. "Ectopic Expression of Methionine Aminopeptidase-2 Causes Cell Transformation and Stimulates Proliferation", Oncogene 27, 3967 (2008).)

SUMMARY

One aspect of the present invention relates to a compound or pharmaceutically acceptable salt thereof, comprising:

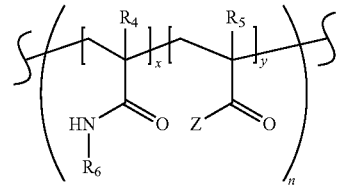

wherein, independently for each occurrence,
$R_4$ is H or $C_1$-$C_6$ alkyl;
$R_5$ is H or $C_1$-$C_6$ alkyl;
$R_6$ is $C_2$-$C_6$ hydroxyalkyl;
Z is —NH-$AA_1$-$AA_2$-$AA_3$-$AA_4$-$AA_5$-$AA_6$-C(O)-L or —NH-$AA_1$-$AA_2$-$AA_3$-$AA_4$-$AA_5$-$AA_6$-C(O)-Q-X—Y—C(O)—W;
$AA_1$ is glycine, alanine, or $H_2N(CH_2)MCO_2H$, wherein m is 2, 3, 4 or 5;
$AA_2$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine;
$AA_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine;
$AA_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine;
$AA_5$ is a bond, or glycine, valine, tyrosine, tryptophan, phenylalanine, methionine, leucine, isoleucine, or asparagine;
$AA_6$ is a bond, or alanine, asparagine, citrulline, glutamine, glycine, leucine, methionine, phenylalanine, serine, threonine, tryptophan, tyrosine, valine, or $H_2N(CH_2)_mCO_2H$, wherein m is 2, 3, 4 or 5;

L is —OH, —O-succinimide, —O-sulfosuccinimide, alkoxy, aryloxy, acyloxy, aroyloxy, alkoxycarbonyloxy, aryloxycarbonyloxy, —NH$_2$, —NH(C$_2$-C$_6$ hydroxyalkyl), halide or perfluoroalkyloxy;

Q is NR, O, or S;

X is M-(C(R)$_2$)$_p$-M-J-M-(C(R)$_2$)$_p$-M-V;

M is a bond, or C(O);

J is a bond, or ((CH$_2$)$_q$Q)$_r$, C$_5$-C$_8$ cycloalkyl, aryl, heteroaryl, NR, O, or S;

Y is NR, O, or S;

R is H or alkyl;

V is a bond or

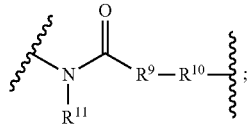

R$_9$ is alkyl, aryl, aralkyl, or a bond; or R$_9$ taken together with Y forms a heterocyclic ring;

R$_{10}$ is amido or a bond;

R$_{11}$ is H or alkyl;

W is a MetAP2 inhibitor moiety or alkyl;

x is in the range of 1 to about 450;

y is in the range of 1 to about 30;

n is in the range of 1 to about 50;

p is 0 to 20;

q is 2 or 3;

r is 1, 2, 3, 4, 5, or 6; and the compound has a molecular weight of less than about 60 kDa.

Another aspect of the present invention relates to a compound or pharmaceutically acceptable salt thereof, represented by Z-Q-X—Y—C(O)—W; wherein, independently for each occurrence, Z is H$_2$N-AA$_6$-C(O)— or H;

AA$_6$ is alanine, asparagine, citrulline, glutamine, glycine, leucine, methionine, phenylalanine, serine, threonine, tryptophan, tyrosine, valine or H$_2$N(CH$_2$)$_m$CO$_2$H, wherein m is 2, 3, 4 or 5;

Q is NR, O, or S;

X is M-(C(R)$_2$)$_p$-M-J-M-(C(R)$_2$)$_p$-M-V;

M is a bond, or C(O);

J is a bond, or ((CH$_2$)$_q$Q)$_r$, C$_5$-C$_8$ cycloalkyl, aryl, heteroaryl, NR, O, or S;

Y is NR, O, or S;

R is H or alkyl;

V is a bond or

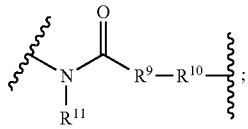

R$^9$ is alkyl, aryl, aralkyl, or a bond; or R$^9$ taken together with Y forms a heterocyclic ring;

R$^{10}$ is amido or a bond;

R$^{11}$ is H or alkyl;

W is a MetAP2 inhibitor moiety;

p is 0 to 20;

q is 2 or 3; and r is 1, 2, 3, 4, 5, or 6.

Another aspect of the invention relates to the use of a compound of the invention to treat a disease (e.g., cancer) in a mammal in need thereof.

DETAILED DESCRIPTION

Figure 1:
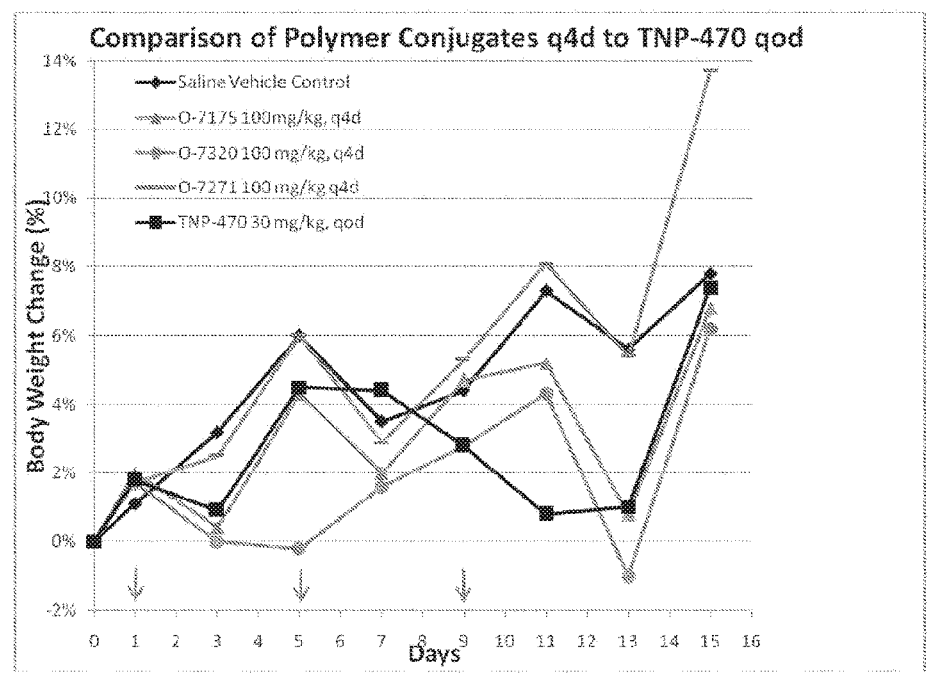
FIG. 1 shows percentage weight change as a function of time for C57Bl/6 mice, injected initially with B16-F10 tumor cells (1×10$^5$), to which one of three polymer conjugates (dosed at 100 mg/kg, q4d) has been administered. Comparative data are included for TNP-470 (dosed at 30 mg/kg, qod) and saline control.

One aspect of the present invention relates to a compound or pharmaceutically acceptable salt thereof, comprising:

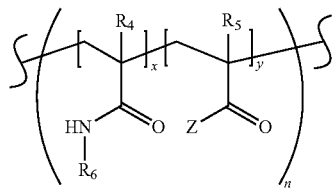

wherein, independently for each occurrence,

R$_4$ is H or C$_1$-C$_6$ alkyl;

R$_5$ is H or C$_1$-C$_6$ alkyl;

R$_5$ is C$_2$-C$_6$ hydroxyalkyl;

Z is —NH-AA$_1$-AA$_2$-AA$_3$-AA$_4$-AA$_5$-AA$_6$-C(O)-L or —NH-AA$_1$-AA$_2$-AA$_3$-AA$_4$-AA$_5$-AA$_6$-C(O)-Q-X—Y—C(O)—W;

AA$_1$ is glycine, alanine, or H$_2$N(CH$_2$)$_m$CO$_2$H, wherein m is 2, 3, 4 or 5;

AA$_2$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine;

AA$_3$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine;

AA$_4$ is a bond, or alanine, cysteine, aspartic acid, glutamic acid, phenylalanine, glycine, histidine, isoleucine, lysine, leucine, methionine, asparagine, proline, glutamine, arginine, serine, threonine, valine, tryptophan, or tyrosine;

$AA_5$ is a bond, or glycine, valine, tyrosine, tryptophan, phenylalanine, methionine, leucine, isoleucine, or asparagine;

$AA_6$ is a bond, or alanine, asparagine, citrulline, glutamine, glycine, leucine, methionine, phenylalanine, serine, threonine, tryptophan, tyrosine, valine, or $H_2N(CH_2)_mCO_2H$, wherein m is 2, 3, 4 or 5;

L is —OH, —O-succinimide, —O-sulfosuccinimide, alkoxy, aryloxy, acyloxy, aroyloxy, alkoxycarbonyloxy, aryloxycarbonyloxy, —$NH_2$, —$NH(C_2-C_6$ hydroxyalkyl), halide or perfluoroalkyloxy;

Q is NR, O, or S;

X is M-$(C(R)_2)_p$-M-J-M-$(C(R)_2)_p$-M-V;

M is a bond, or C(O);

J is a bond, or $((CH_2)_qQ)_r$, $C_5-C_8$ cycloalkyl, aryl, heteroaryl, NR, O, or S;

Y is NR, O, or S;

R is H or alkyl;

V is a bond or

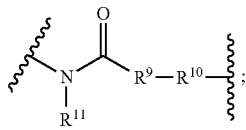

$R^9$ is alkyl, aryl, aralkyl, or a bond; or $R^9$ taken together with Y forms a heterocyclic ring;

$R^{10}$ amido or a bond;

$R^{11}$ is H or alkyl;

W is a MetAP2 inhibitor moiety or alkyl;

x is in the range of 1 to about 450;

y is in the range of 1 to about 30;

n is in the range of 1 to about 50;

p is 0 to 20;

q is 2 or 3;

r is 1, 2, 3, 4, 5, or 6; and the compound has a molecular weight of less than about 60 kDa.

In certain embodiments, P is $C_1-C_6$ alkyl. In certain embodiments, $R_4$ is methyl. In certain embodiments, $R_5$ is $C_1-C_6$ alkyl. In certain embodiments, $R_5$ is methyl. In certain embodiments, $R_6$ is 2-hydroxyethyl, 2-hydroxypropyl or 3-hydroxypropyl. In certain embodiments, $R_6$ is 2-hydroxypropyl.

In other embodiments, the molecular weight is less than about 45 kDa. In other embodiments, the molecular weight is less than about 35 kDa.

In certain embodiments, the ratio of x toy is in the range of about 30:1 to about 3:1. In other embodiments, the ratio of x toy is in the range of about 20:1 to about 4:1. In certain embodiments, the ratio of x toy is in the range of about 15:1 to about 6:1. In certain embodiments, the ratio of x toy is about 15:1. In certain embodiments, the ratio of x to y is about 11:1. In certain embodiments, the ratio of x to y is about 6:1.

In certain embodiments, Z is —NH-$AA_1$-$AA_2$-$AA_3$-$AA_4$-$AA_5$-$AA_6$-C(O)-L.

In certain embodiments, L is methoxy, ethoxy, pentafluorophenyloxy, phenyloxy, acetoxy, fluoride, chloride, methoxycarbonyloxy; ethoxycarbonyloxy, phenyloxycarbonyloxy, 4-nitrophenyloxy, trifluoromethoxy, pentafluoroethoxy, or trifluoroethoxy. In certain embodiments, L is 4-nitrophenyloxy.

In certain embodiments, Z is —NH-$AA_1$-$AA_2$-$AA_3$-$AA_4$-$AA_5$-$AA_6$-C(O)-Q-X—Y—C(O)—W. In certain embodiments, $AA_1$ is glycine. In certain embodiments, $AA_2$ is glycine. In certain embodiments, $AA_3$ is glycine. In certain embodiments, $AA_4$ is glycine or phenylalanine. In certain embodiments, $AA_5$ is leucine, phenylalanine, valine or tyrosine. In certain embodiments, $AA_6$ is asparagine, citrulline, glutamine, glycine, leucine, methionine, threonine or tyrosine. In certain embodiments, $AA_5$-$AA_6$ is Leu-Cit, Leu-Gln, Leu-Gly, Leu-Leu, Leu-Met, Leu-Thr, Phe-Cit, Phe-Gln, Phe-Leu, Phe-Met, Phe-Thr, Val-Asn, Val-Cit, Val-Gln, Val-Leu, Val-Met, Val-Thr, Tyr-Cit, Tyr-Leu, or Tyr-Met. In certain embodiments, $AA_1$, $AA_3$ and $AA_5$ are glycine, valine, tyrosine, tryptophan, phenylalanine, methionine, leucine, isoleucine, or asparagine. In certain embodiments, $AA_2$, $AA_4$ and $AA_6$ are glycine, asparagine, citrulline, glutamine, glycine, leucine, methionine, phenylalanine, threonine or tyrosine. In certain embodiments, $AA_2$ is a bond; and $AA_3$ is a bond. In certain embodiments, $AA_1$ is glycine; $AA_4$ is phenylalanine; $AA_5$ is leucine; and $AA_6$ is glycine.

In certain embodiments, W is

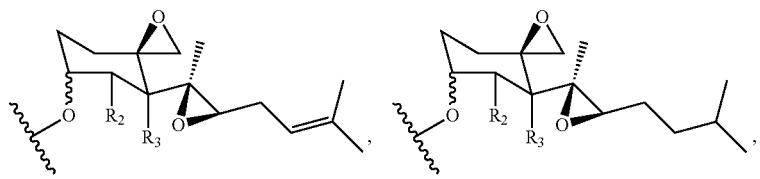

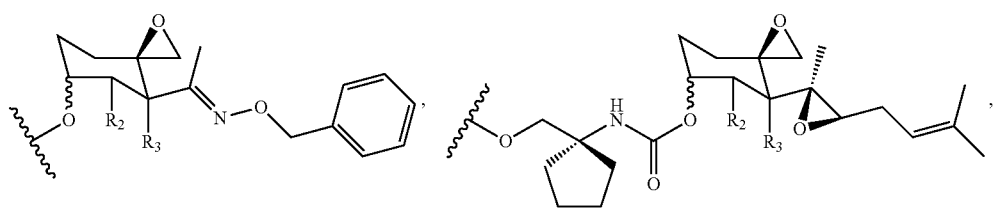

-continued
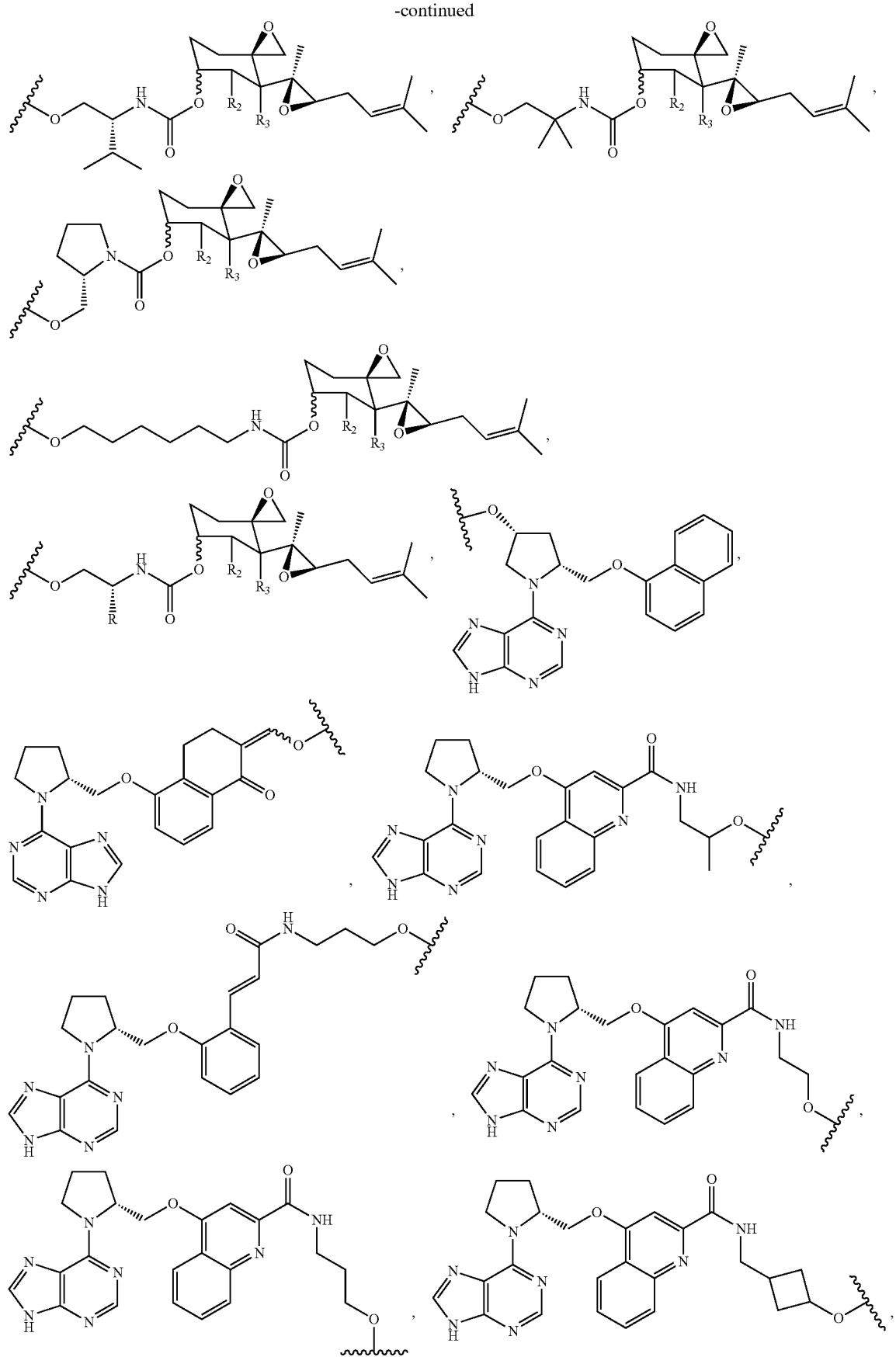

-continued
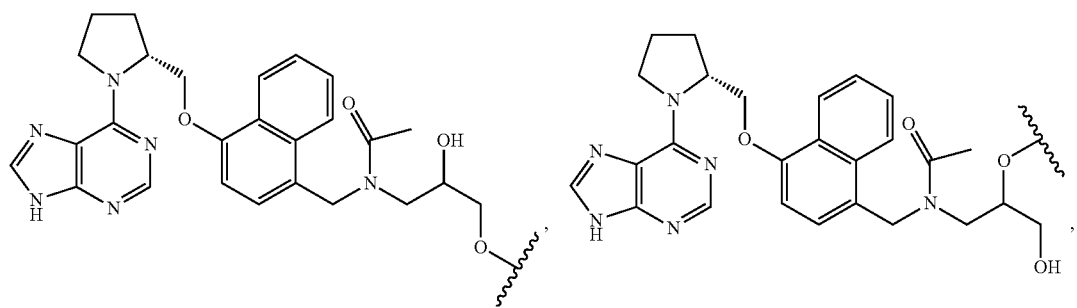
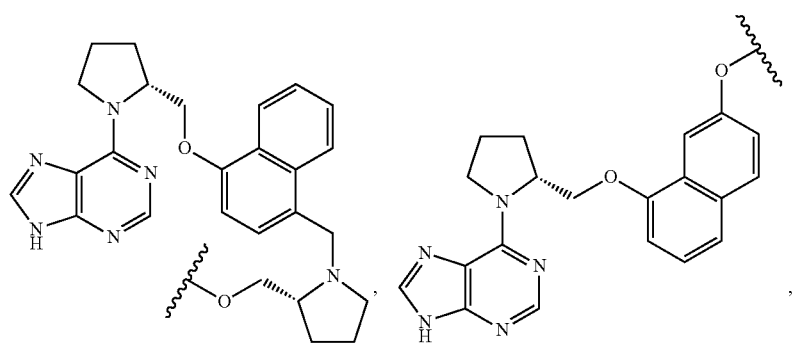
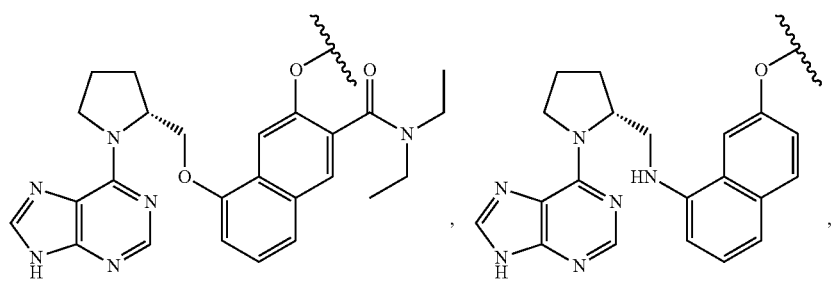
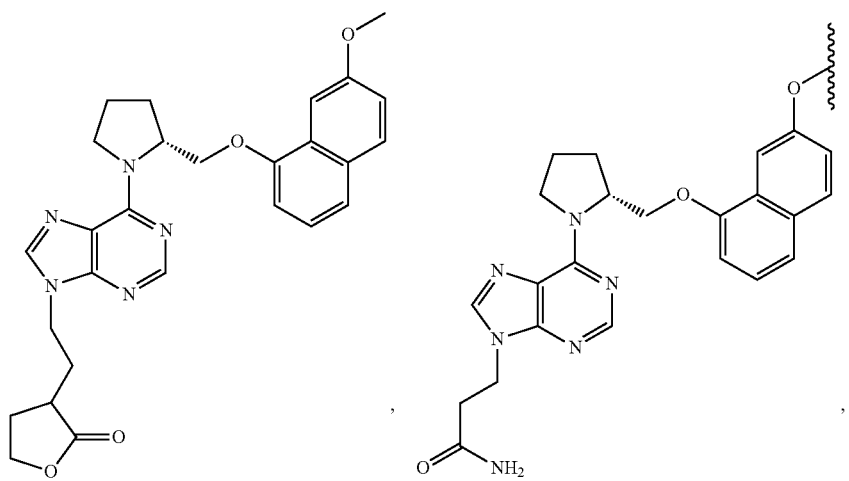

-continued
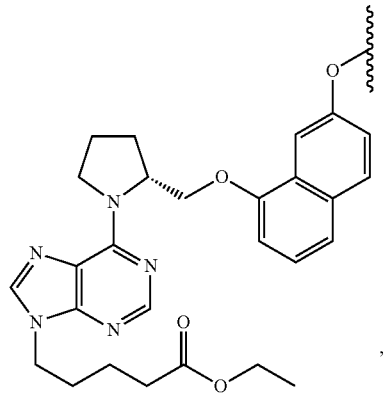,
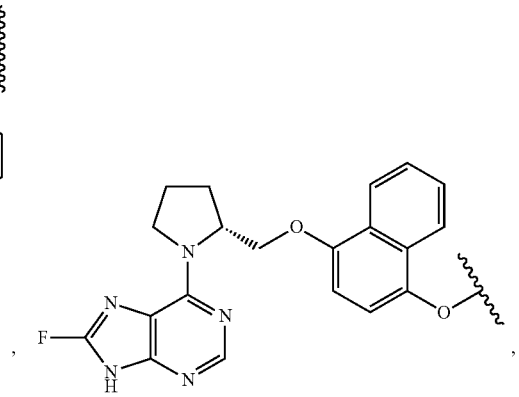,
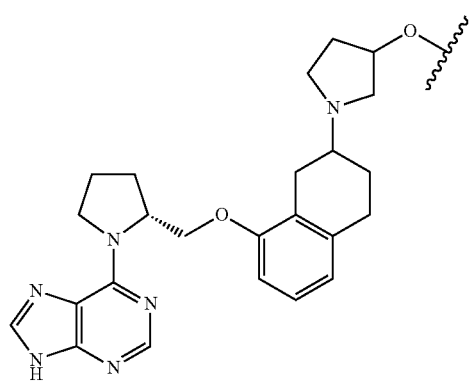,
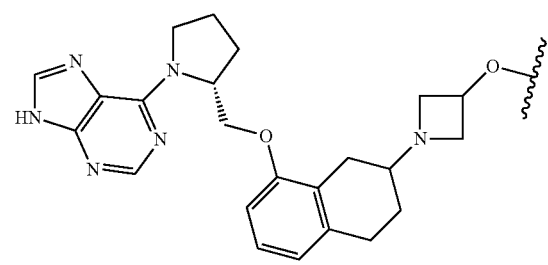,
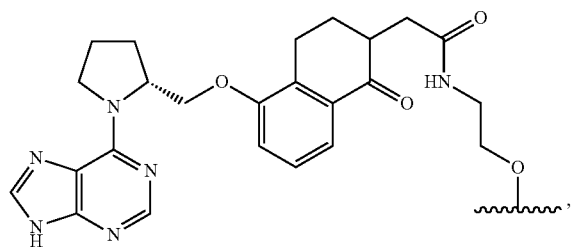,
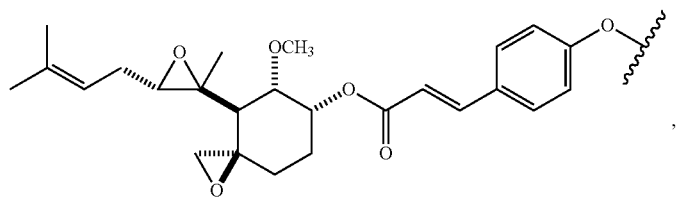,
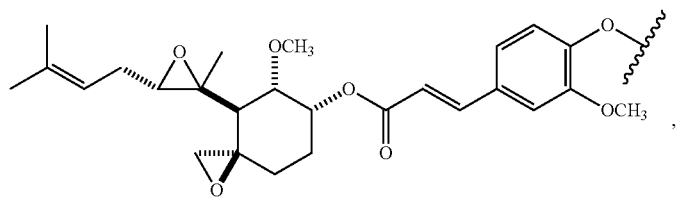,
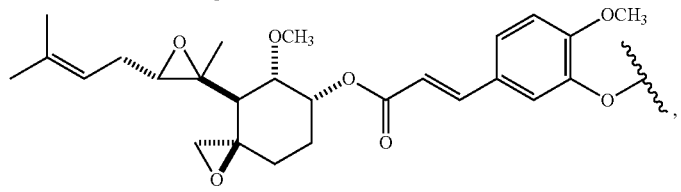,

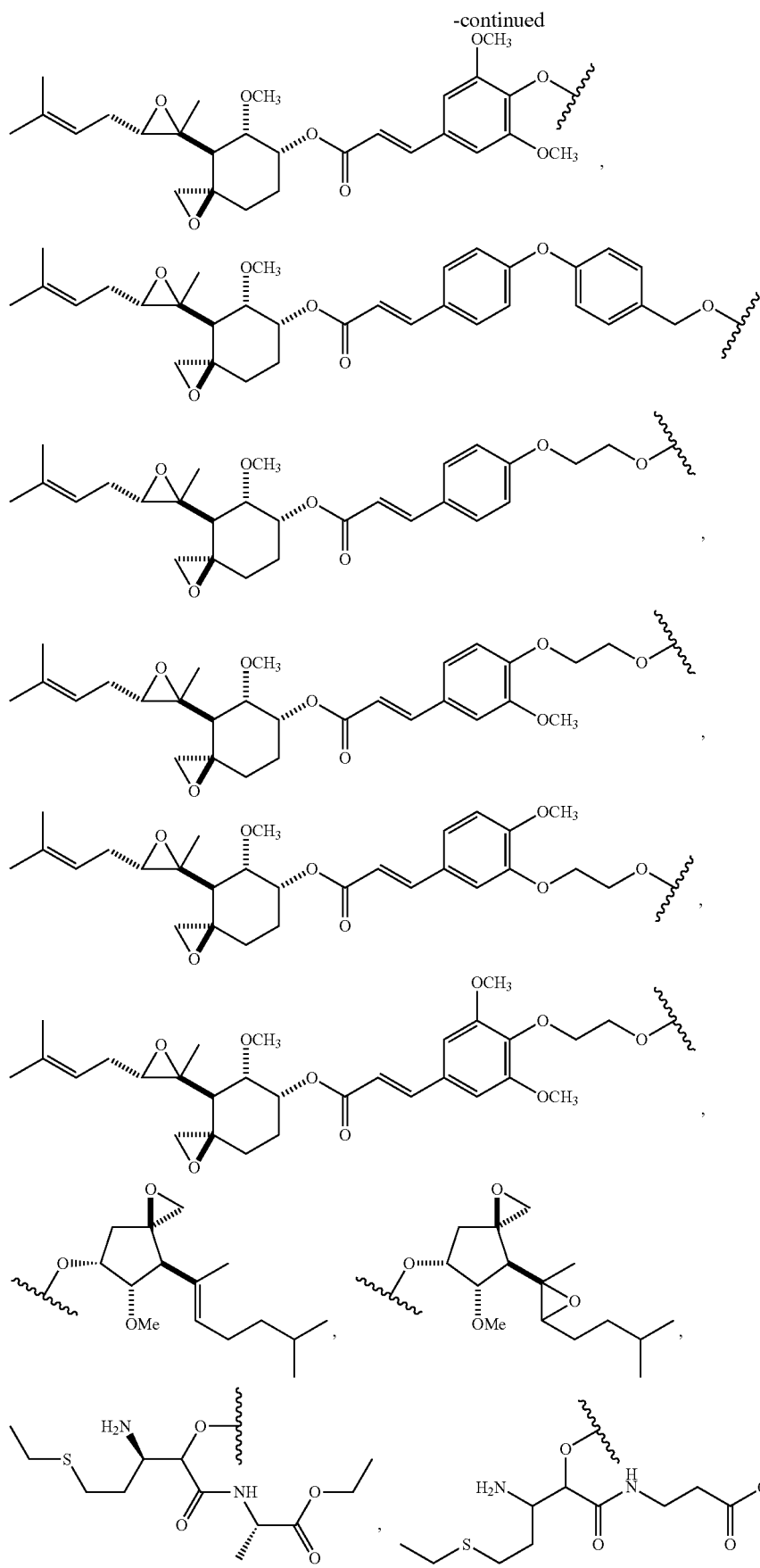

-continued
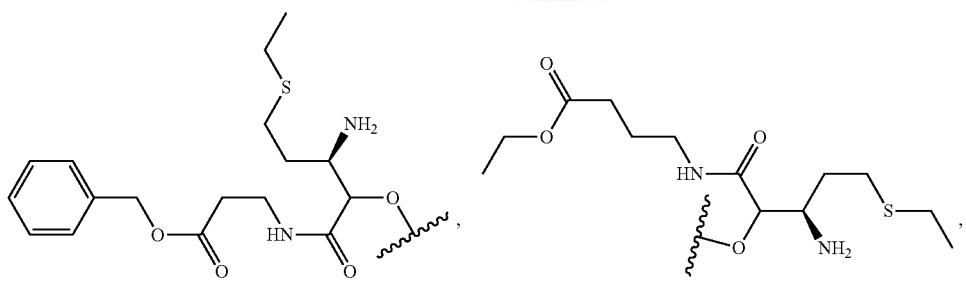
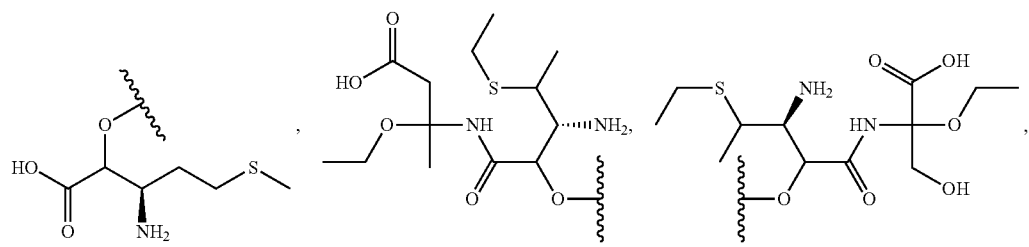
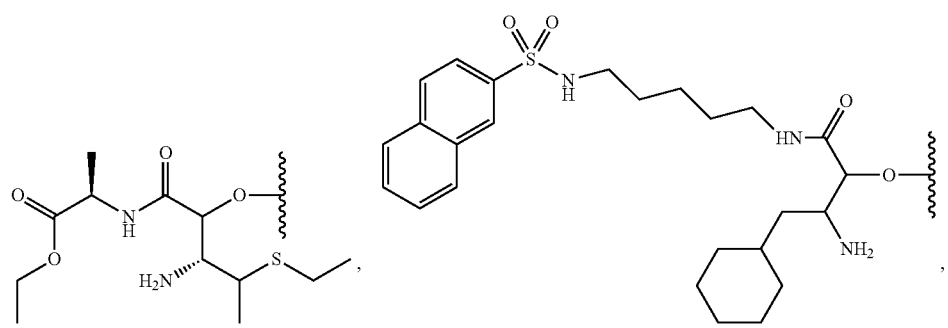
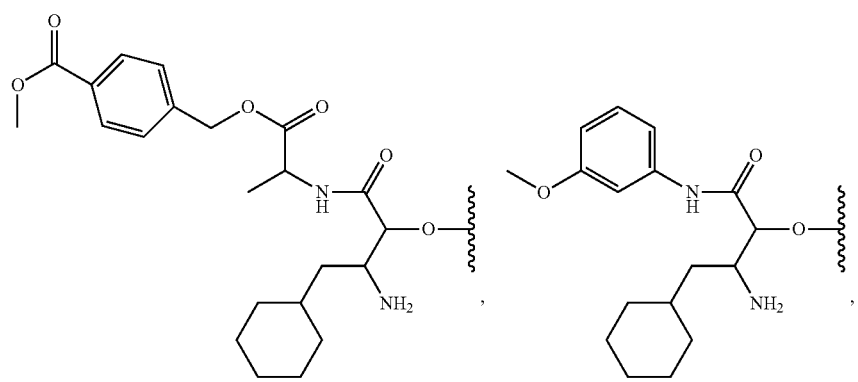
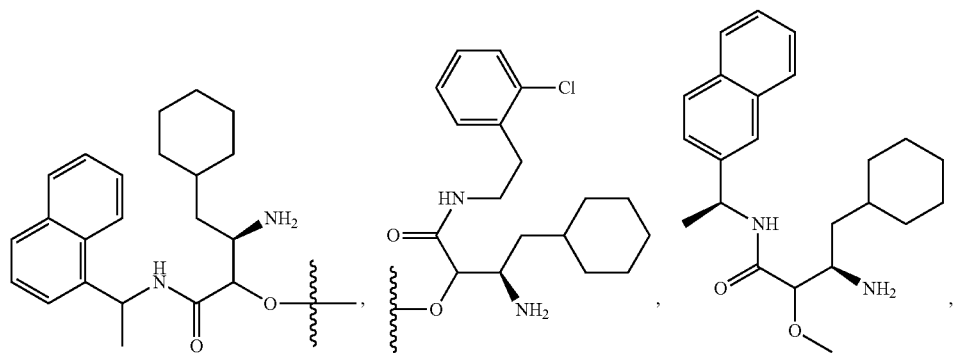

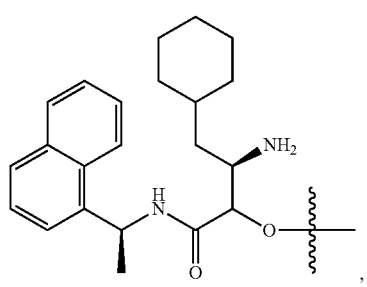
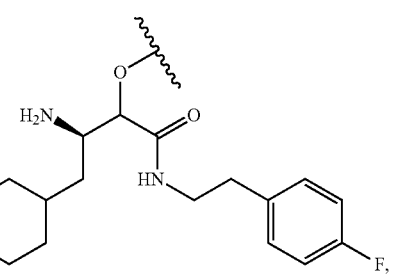
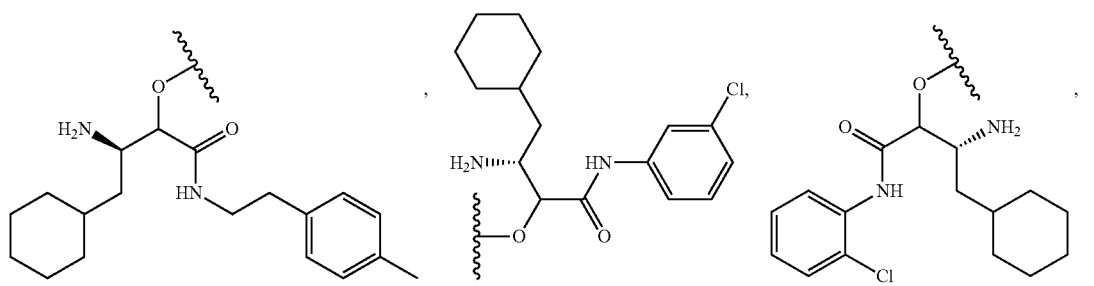
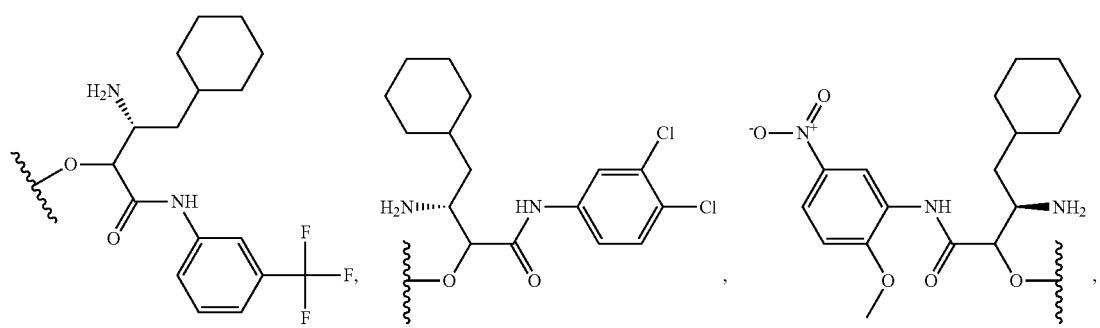
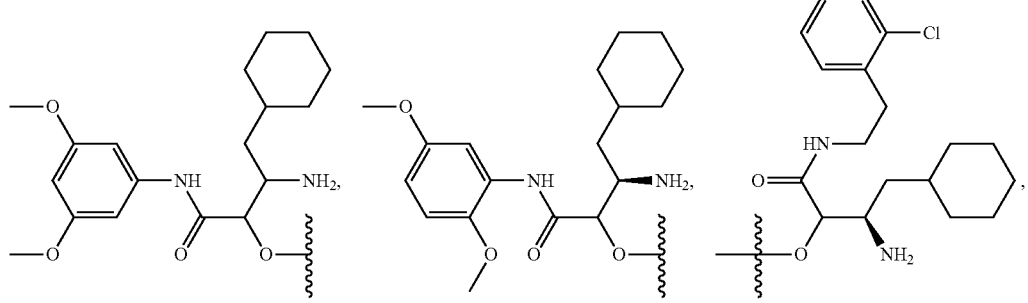
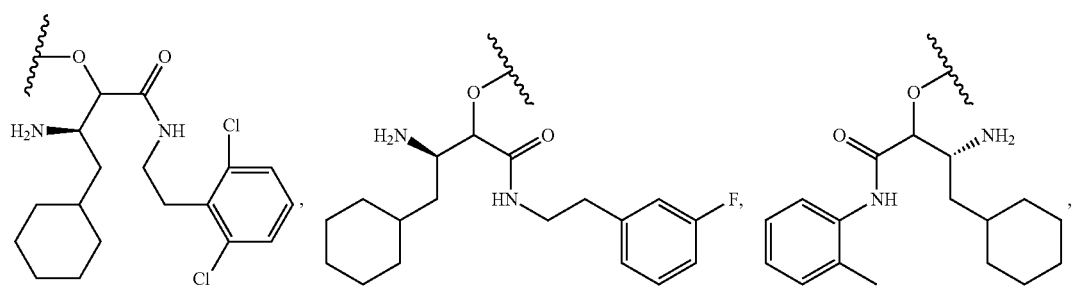

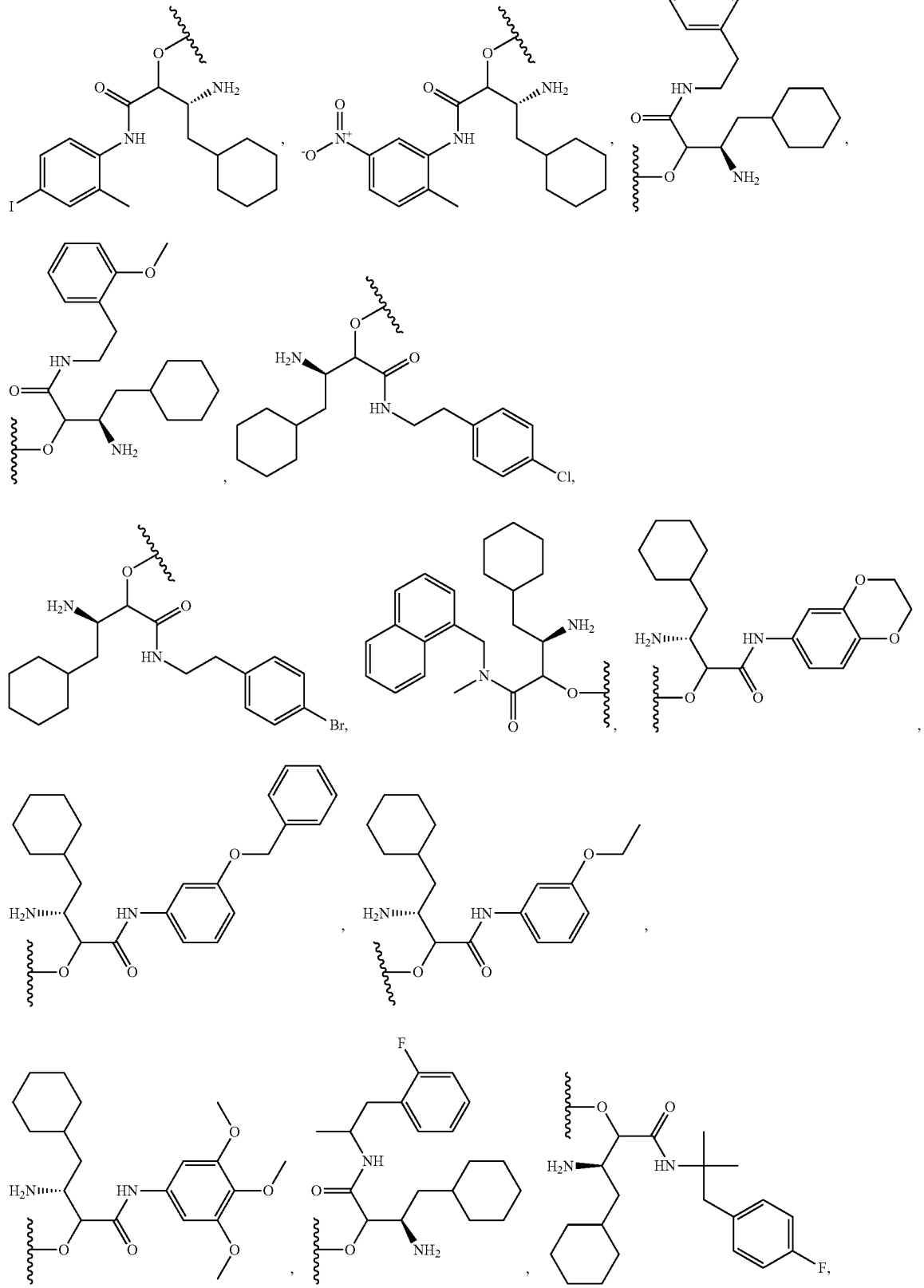

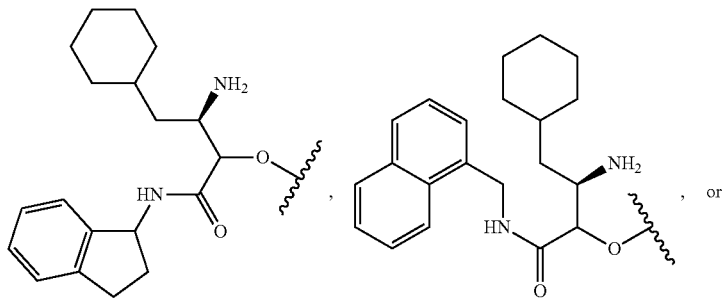
wherein $R_2$ is —OH or methoxy; and $R_3$ is H, —OH or methoxy.
In certain embodiments, W is
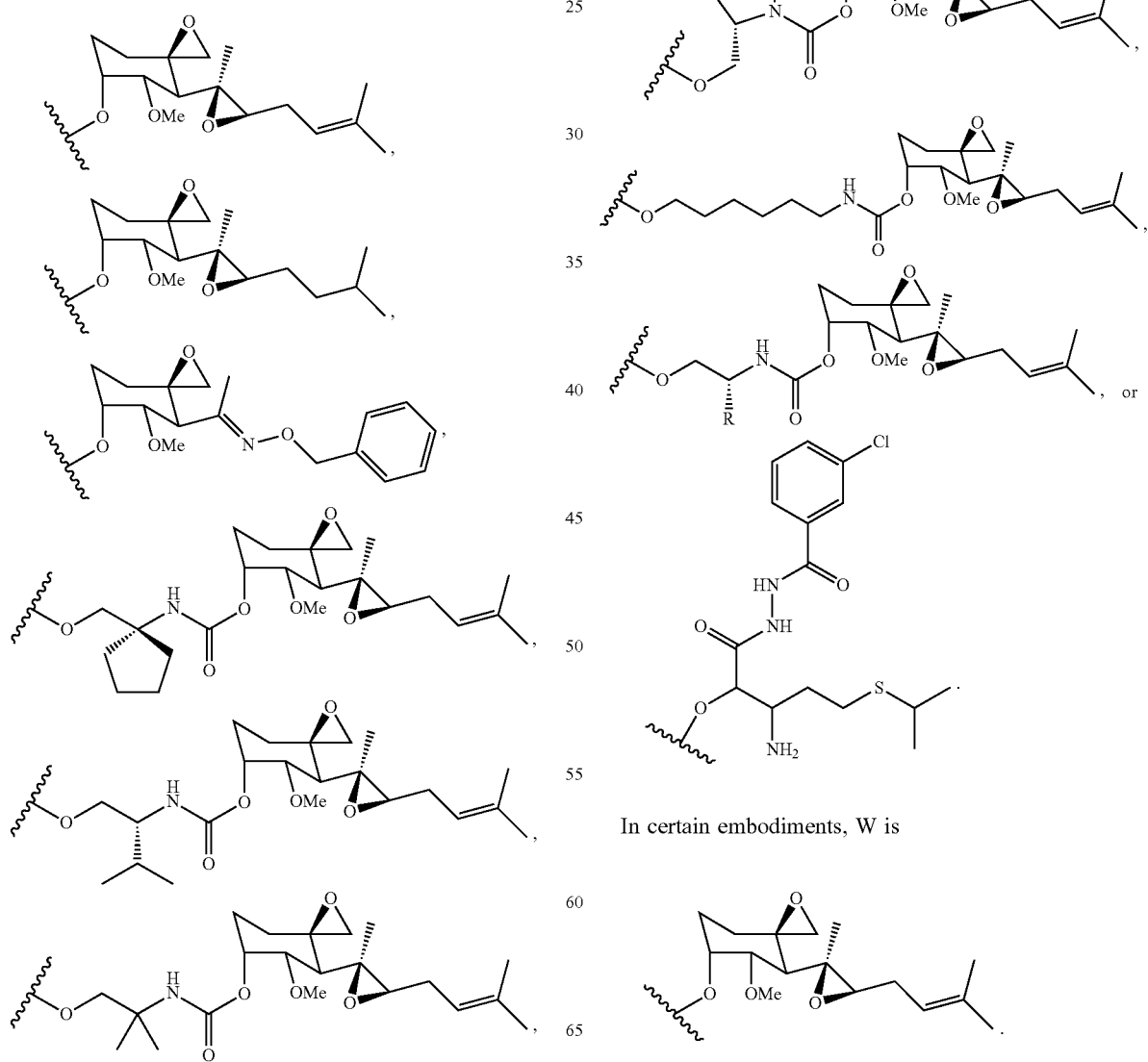
In certain embodiments, W is In certain embodiments, Q is NR. In other embodiments, Q is S.
In certain embodiments, J is NR. In other embodiments, J is $((CH_2)_qQ)_r$. In other embodiments, J is $C_5$-$C_8$ cycloalkyl. In certain embodiments, J is aryl.
In certain embodiments, Y is NR. In other embodiments, Y is S.
In certain embodiments, -Q-X—Y— is
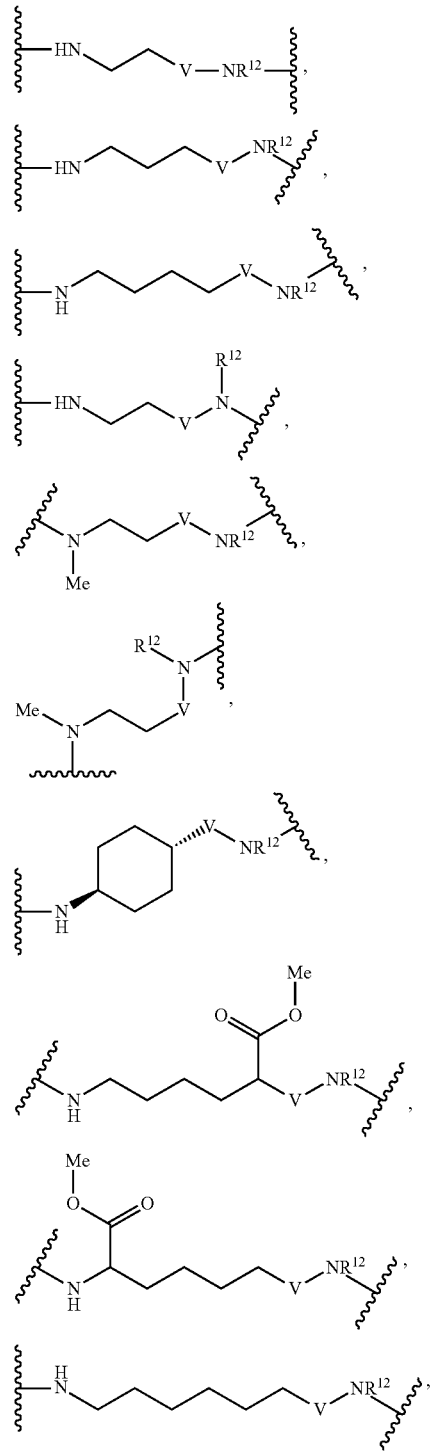
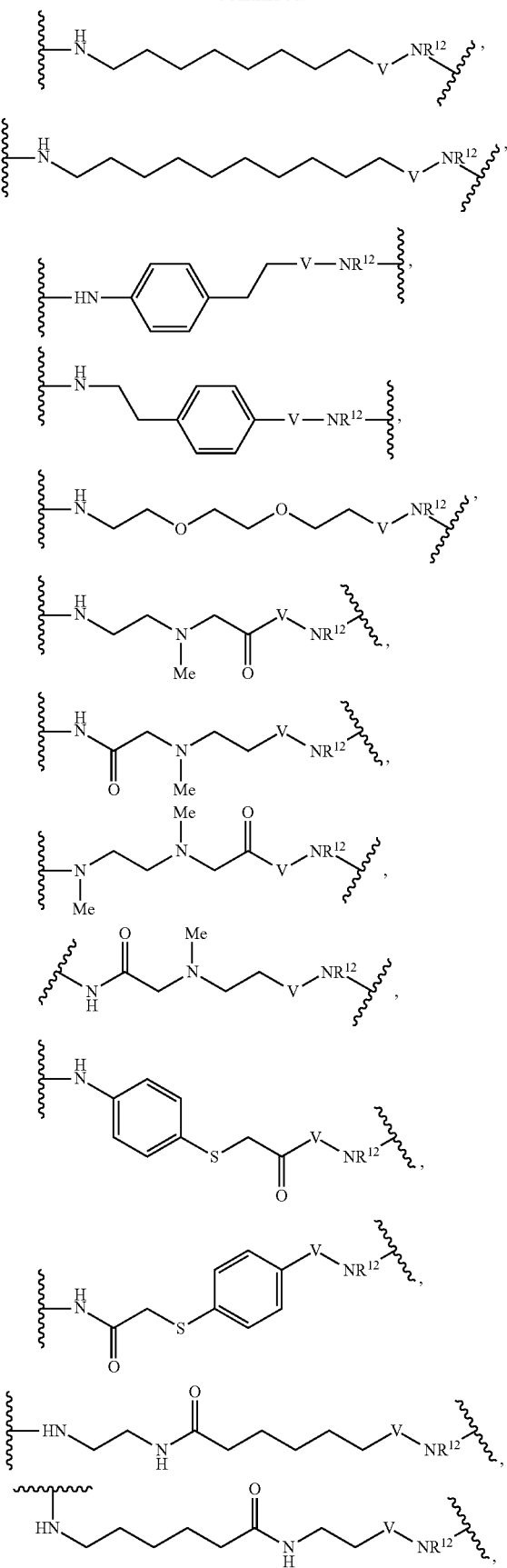

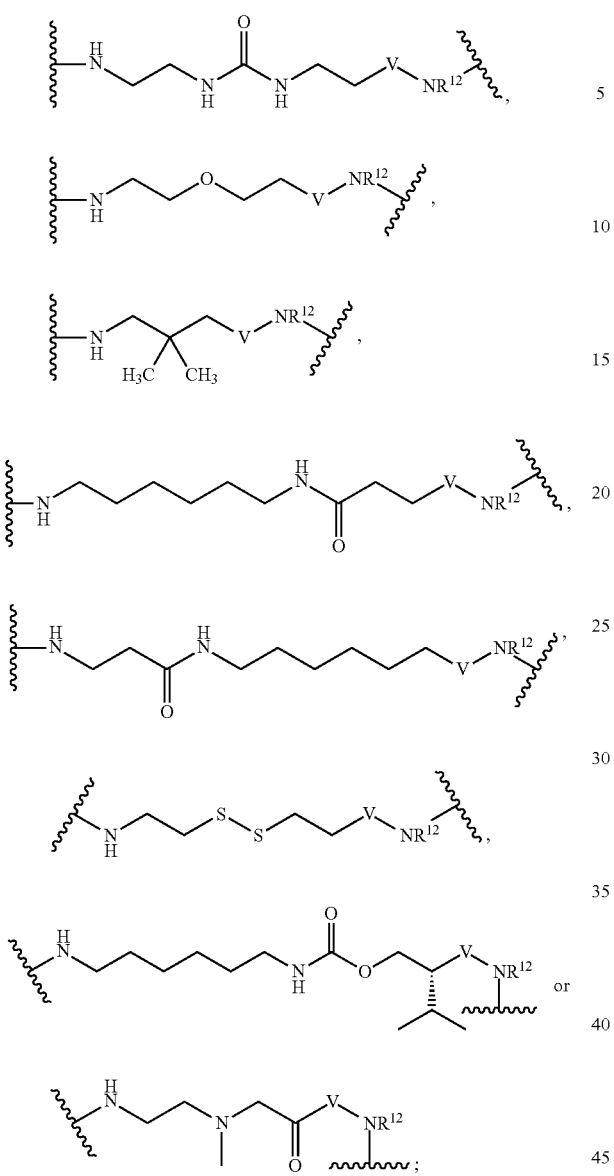
V is:
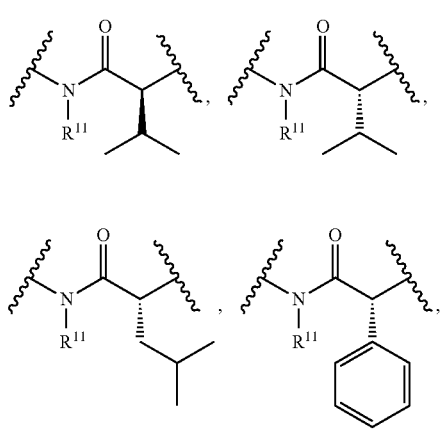
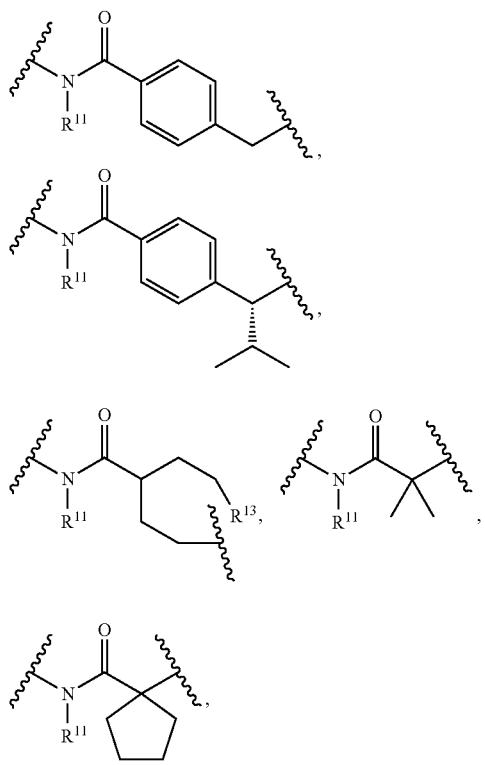
or a bond;
R$^{12}$ is H or Me; or R taken together with R forms a piperidine ring;
R$^{11}$ is H or Me; and
R$^{13}$ taken together with R$^{12}$ forms a piperidine ring.
In certain embodiments, -Q-X—Y— is
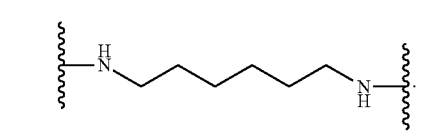 [SMILES: *NCCCCCCN*]
In certain embodiments, -Q-X—Y— is
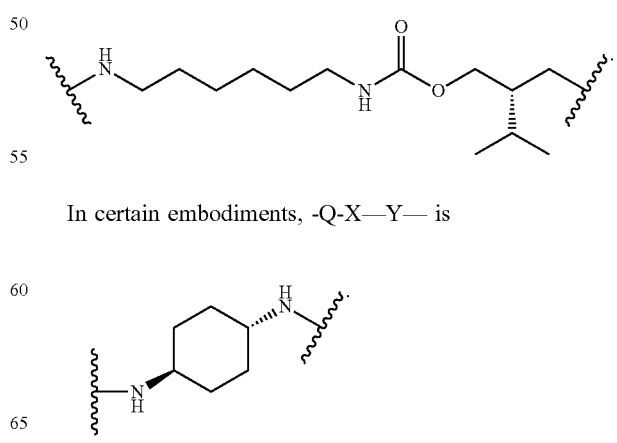
In certain embodiments, -Q-X—Y— is In certain embodiments, -Q-X—Y— is

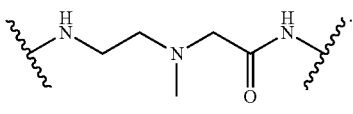 [SMILES: *NCCN(C)CC(=O)N*]

In certain embodiments, $R_4$ and $R_5$ are methyl; is 2-hydroxypropyl; Z is —NH-$AA_1$-$AA_2$-$AA_3$-$AA_4$-$AA_5$-$AA_6$-C(O)-Q-X—Y—C(O)—W; $AA_1$ is glycine; $AA_2$ is a bond; $AA_3$ is a bond; $AA_4$ is phenylalanine; $AA_5$ is leucine; $AA_6$ is glycine; -Q-X—Y— is

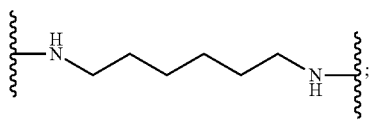 [SMILES: *NCCCCCCN*]

and W is

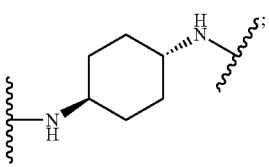

In certain embodiments, $R_4$ and $R_5$ are methyl; is 2-hydroxypropyl; Z is —NH-$AA_1$-$AA_2$-$AA_3$-$AA_4$-$AA_5$-$AA_6$-C(O)-Q-X—Y—C(O)—W; $AA_1$ is glycine; $AA_2$ is a bond; $AA_3$ is a bond; $AA_4$ is phenylalanine; $AA_5$ is leucine; $AA_6$ is glycine; -Q-X—Y— is

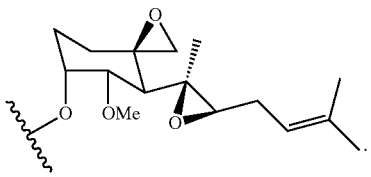

and W is

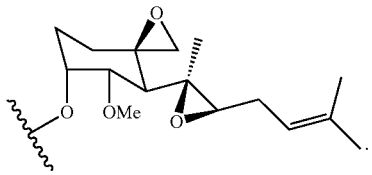

In certain embodiments, $R_4$ and $R_5$ are methyl; $R_6$ is 2-hydroxypropyl; Z is —NH-$AA_1$-$AA_2$-$AA_3$-$AA_4$-$AA_5$-$AA_6$-C(O)-Q-X—Y—C(O)—W; $AA_1$ is glycine; $AA_2$ is a bond; $AA_3$ is a bond; $AA_4$ is phenylalanine; $AA_5$ is leucine, $AA_6$ is glycine; -Q-X—Y— is

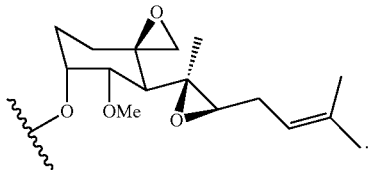

and W is

In certain embodiments, -Q-X—Y— is a self-immolating linker that releases the MetAP2 inhibitor in the form of a carbamate derivative, as shown in the scheme below:

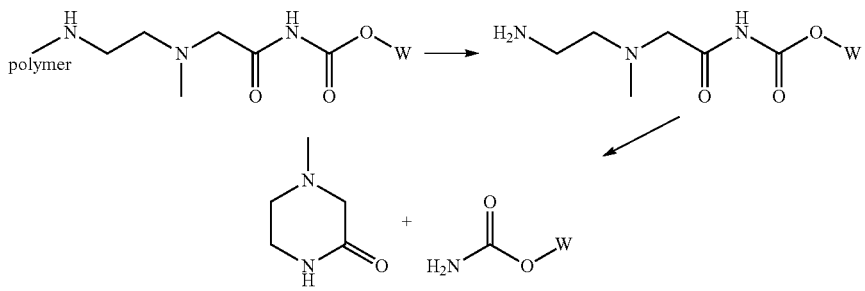

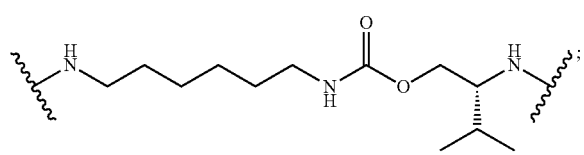 [SMILES: *NCCCCCCNC(=O)OC[C@H](N*)C(C)C]

Another aspect of the present invention relates to a compound or pharmaceutically acceptable salt thereof, represented by

Z-Q-X—Y—C(O)—W wherein, independently for each occurrence,

Z is $H_2N$-$AA_6$-C(O)— or H;

$AA_6$ is alanine, asparagine, citrulline, glutamine, glycine, leucine, methionine, phenylalanine, serine, threonine, tryptophan, tyrosine, valine or $H_2N(CH_2)_m CO_2H$, wherein m is 2, 3, 4 or 5;

Q is NR, O, or S;

X is M-$(C(R)_2)_p$-M-J-M-$(C(R)_2)_p$-M-V;

M is a bond, or C(O);
J is a bond, or $((CH_2)_qQ)_r$, $C_5$-$C_8$ cycloalkyl, aryl, heteroaryl, NR, O, or S;
Y is NR, O, or S;
R is H or alkyl;
V is a bond or
$R^9$ is alkyl, aryl, aralkyl, or a bond; or $R^9$ taken together with Y forms a heterocyclic ring;
$R^{10}$ is amido or a bond;
$R^{11}$ is H or alkyl;
W is a MetAP2 inhibitor moiety;

p is 0 to 20;
q is 2 or 3; and
r is 1, 2, 3, 4, 5, or 6.

In certain embodiments, Z is H. In other embodiments, Z is $H_2N$-$AA_6$-C(O)—

In certain embodiments, $AA_6$ is glycine.
In certain embodiments, Q is NR.
In certain embodiments, M is a bond.
In certain embodiments, J is a bond.
In certain embodiments, Y is NR.
In certain embodiments, W is:

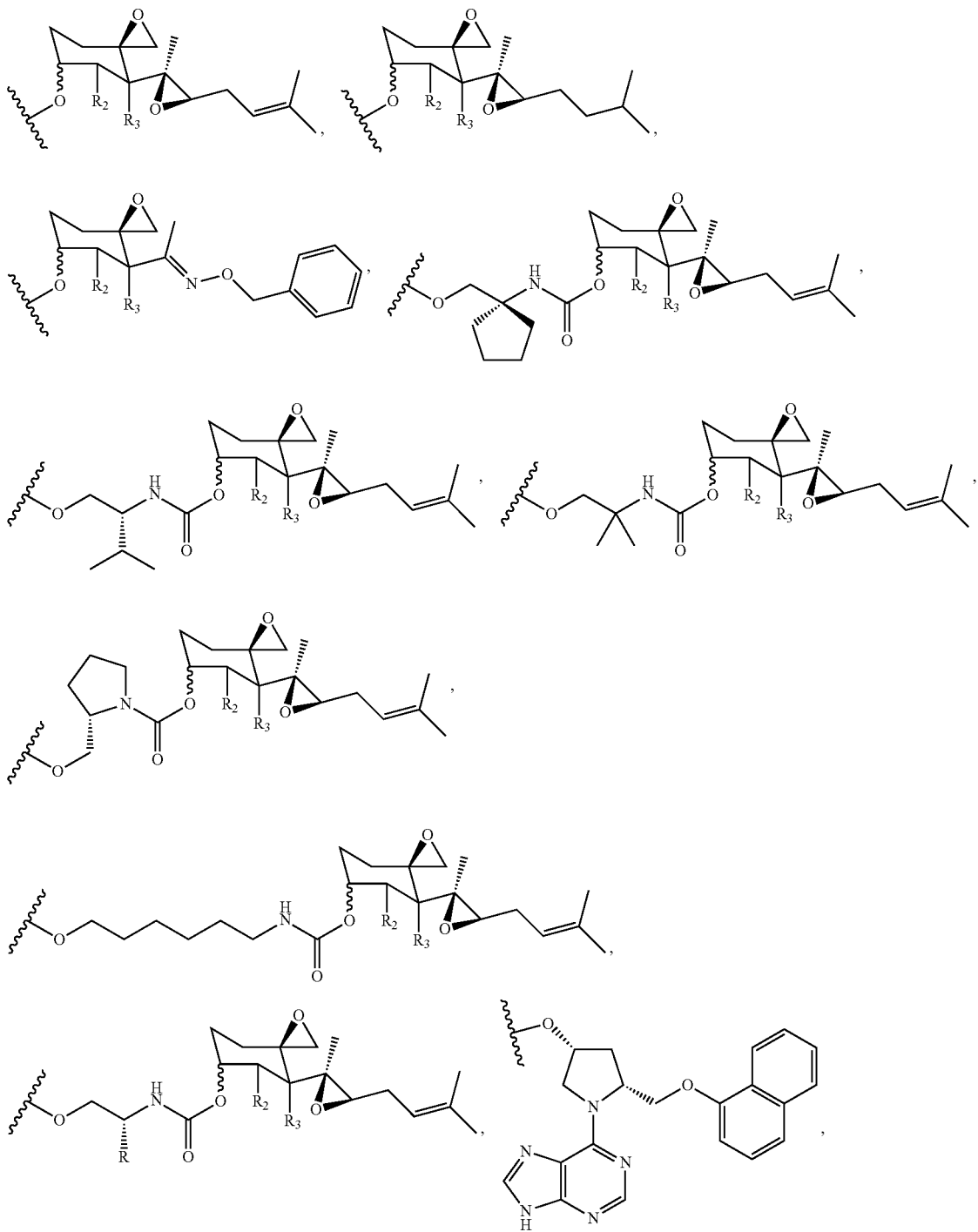

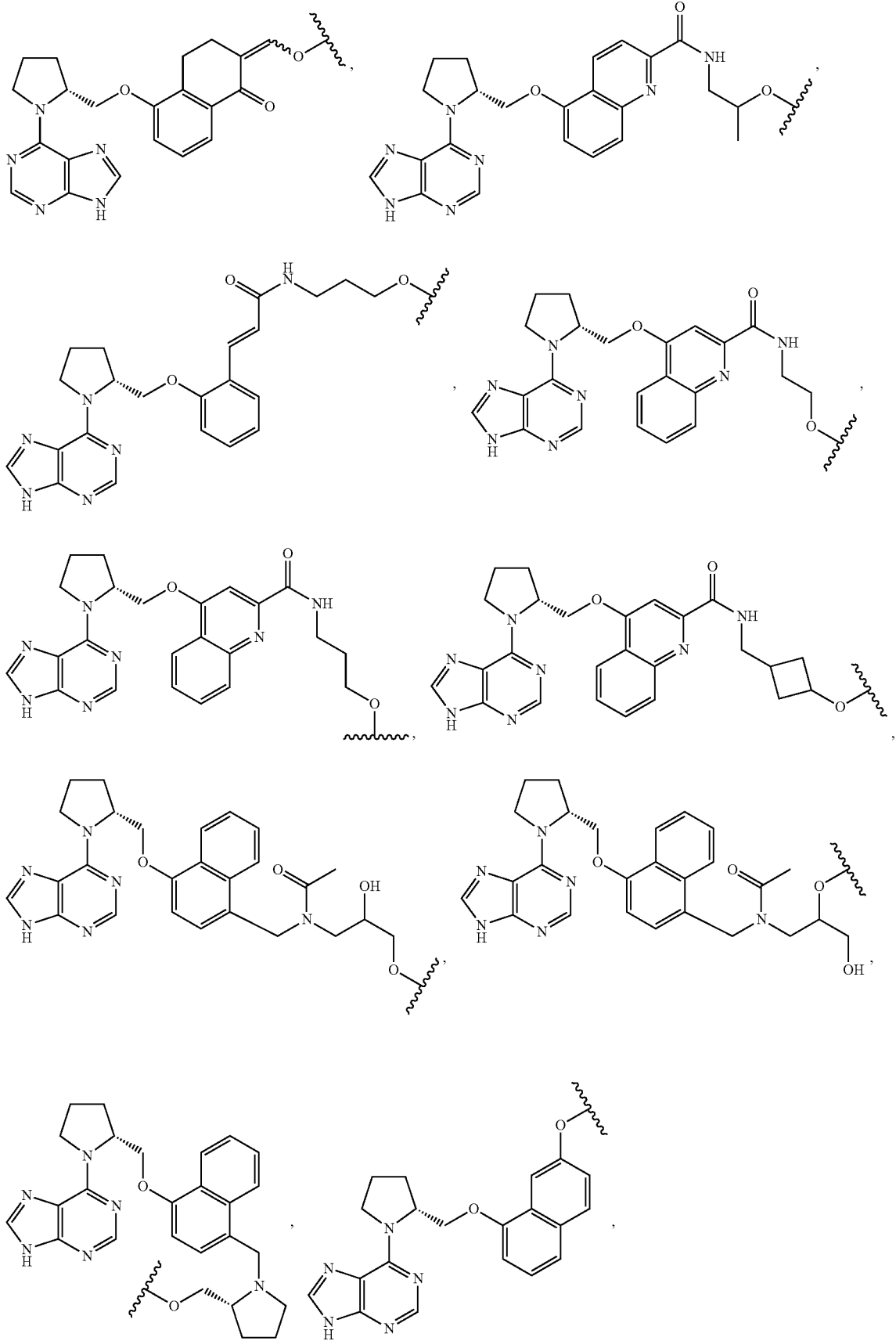

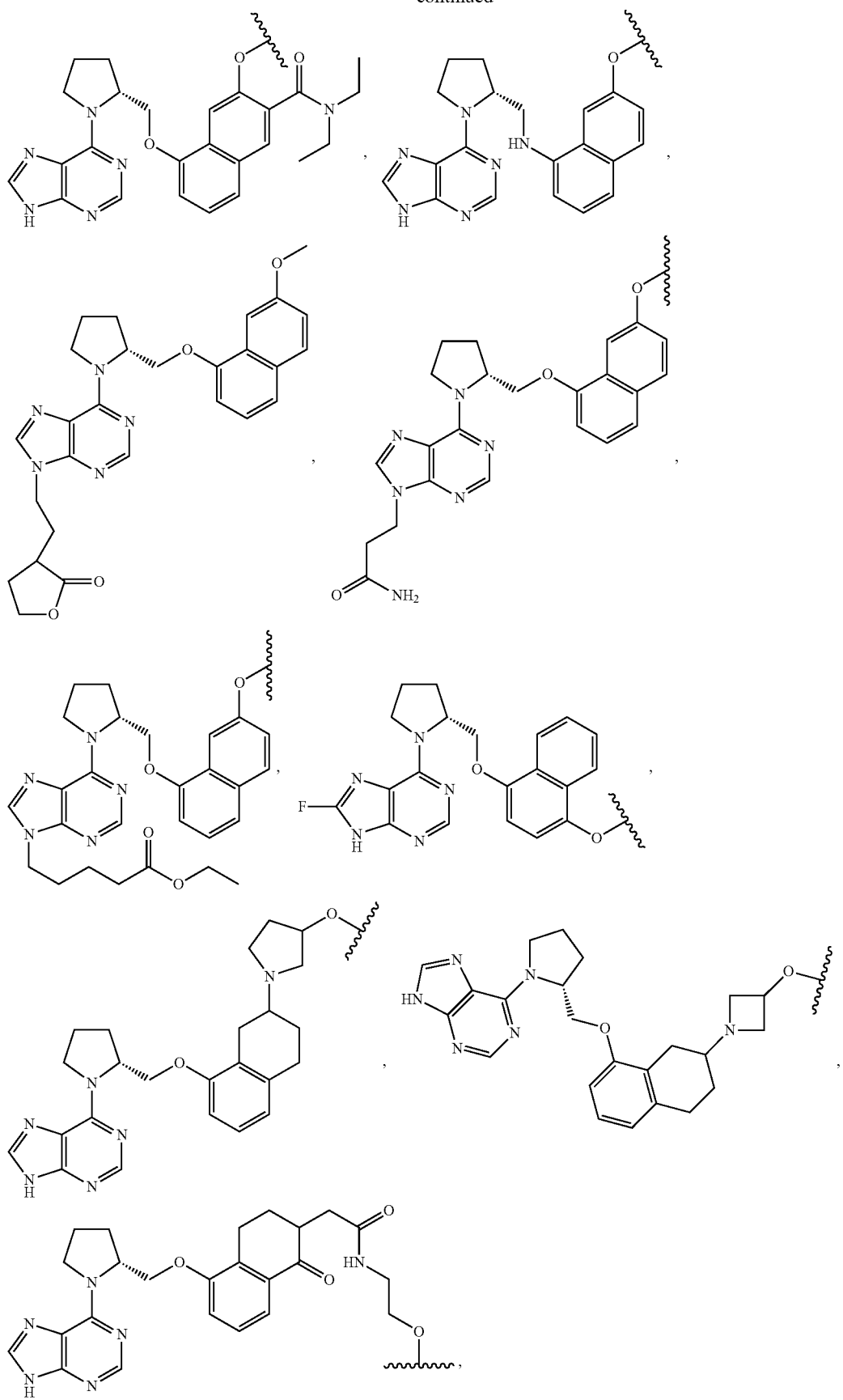

-continued
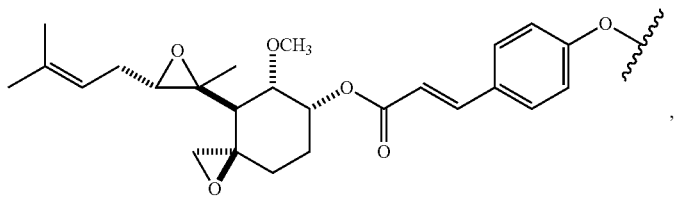
,
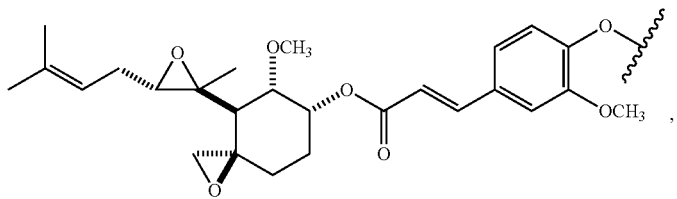
,
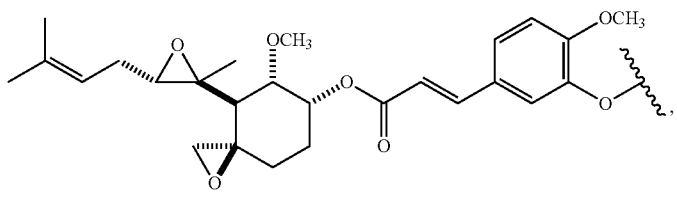
,
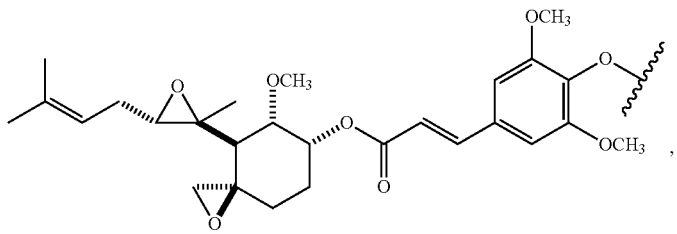
,
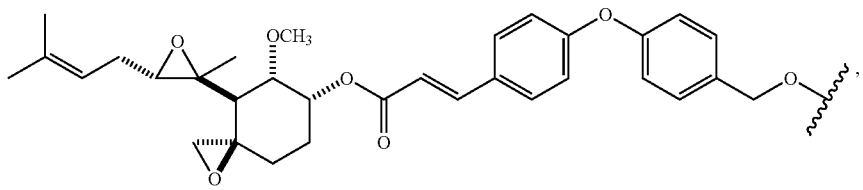
,
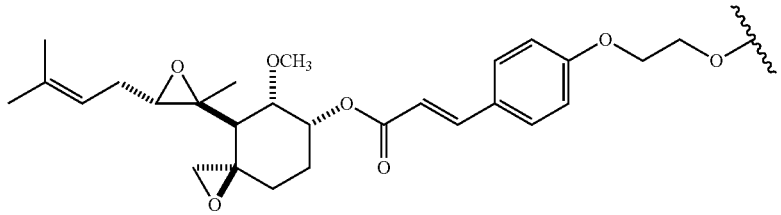
,
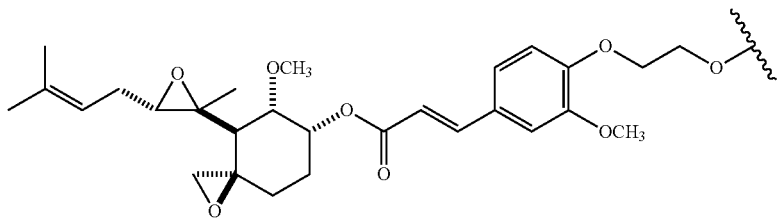
,
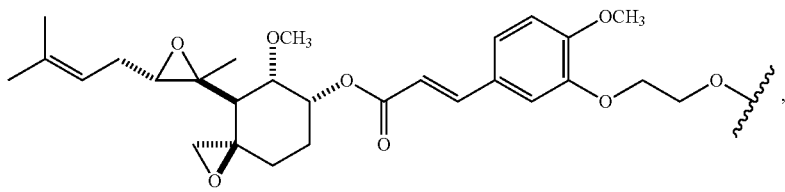
,

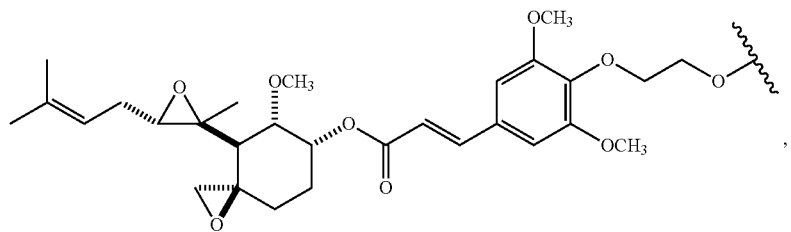
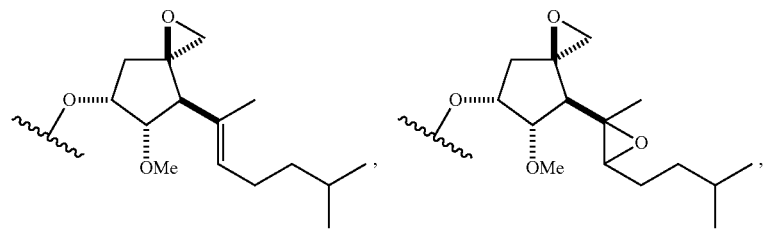
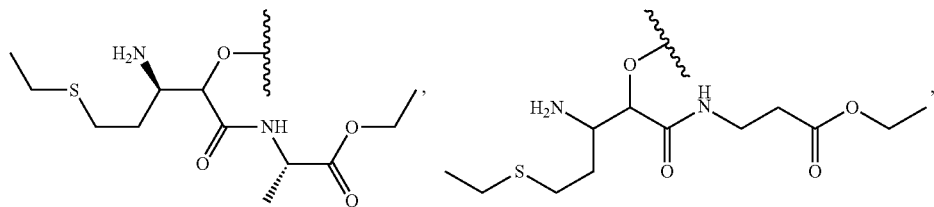
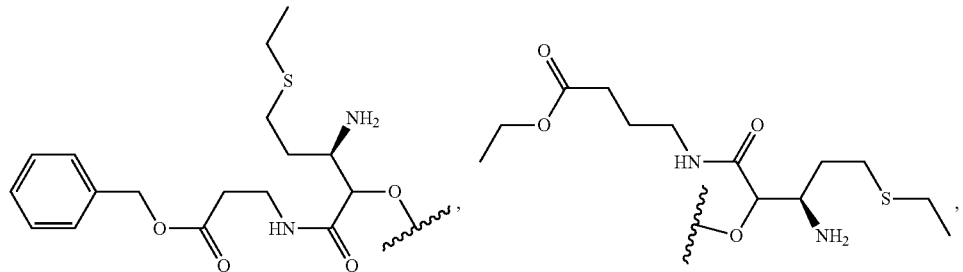
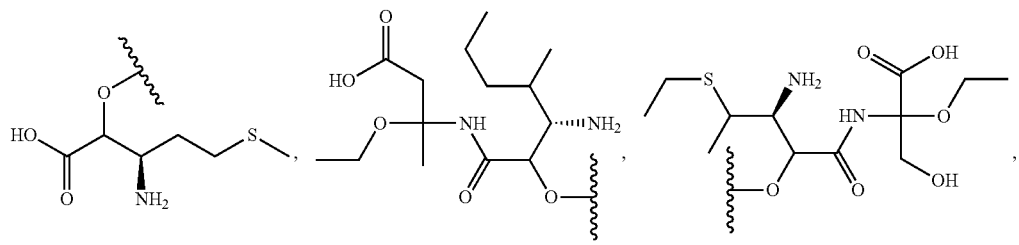
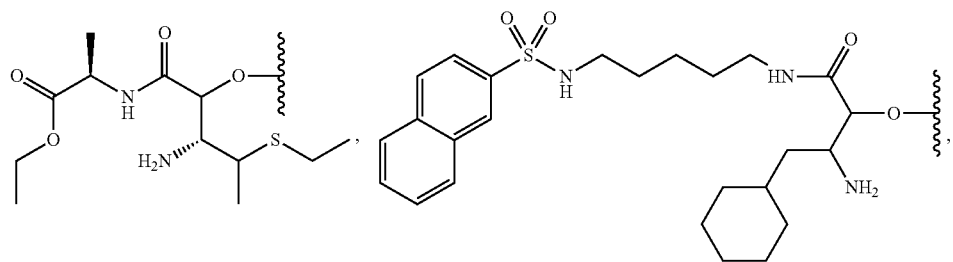

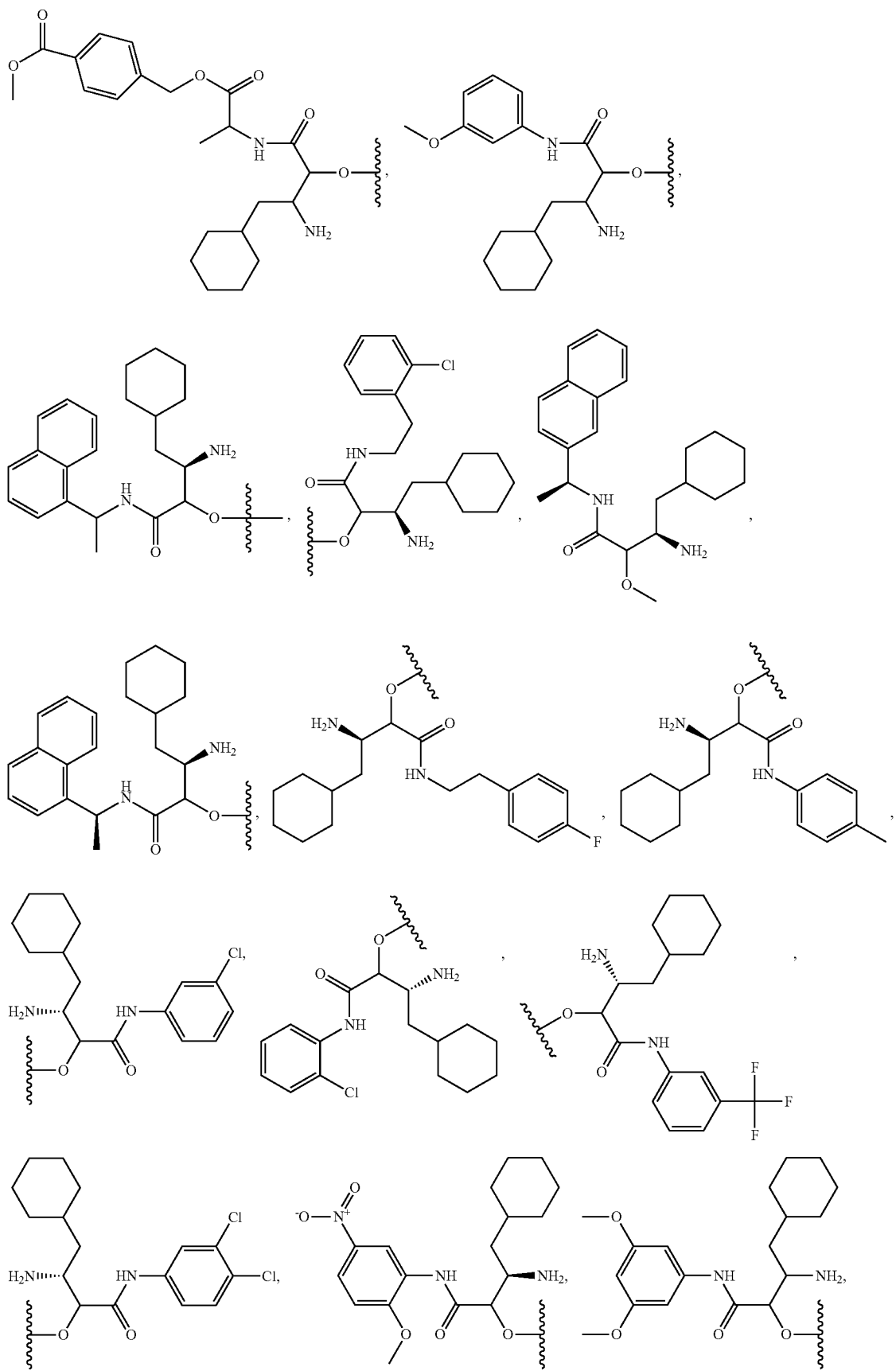

-continued
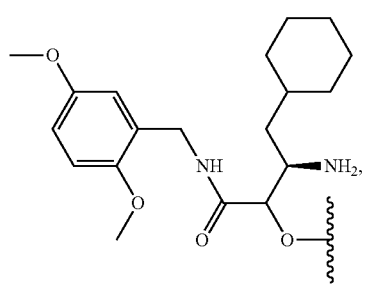 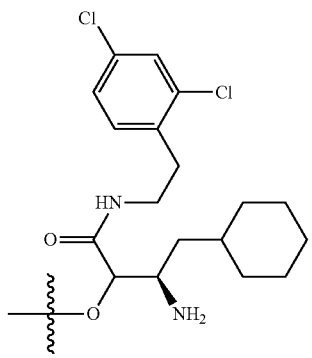 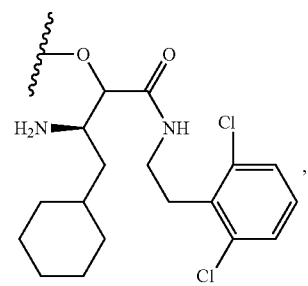
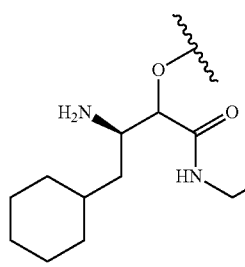 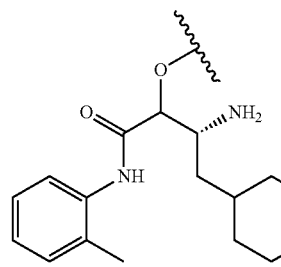 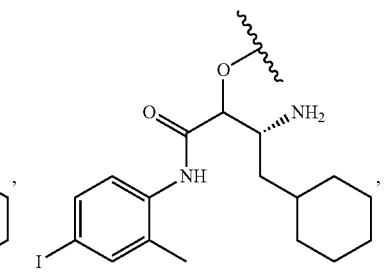
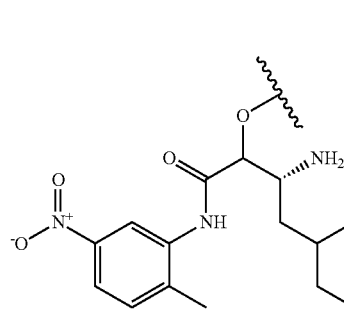 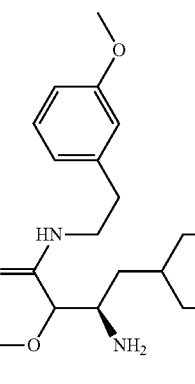 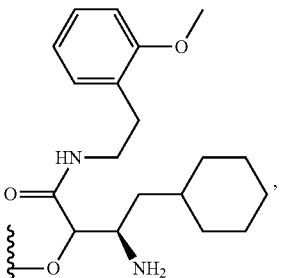
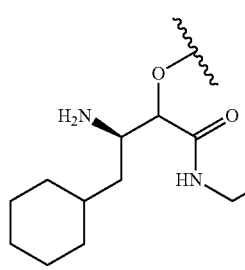 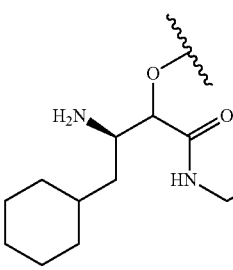 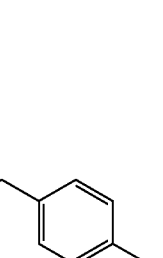
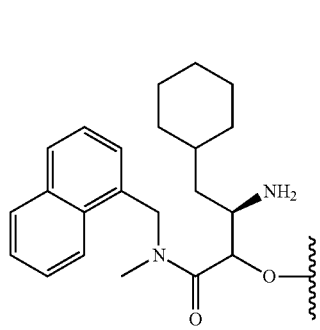 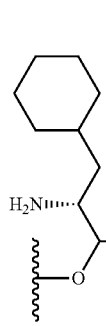 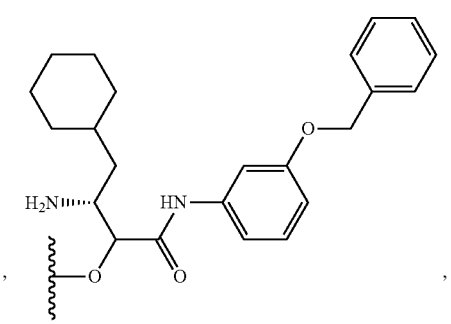

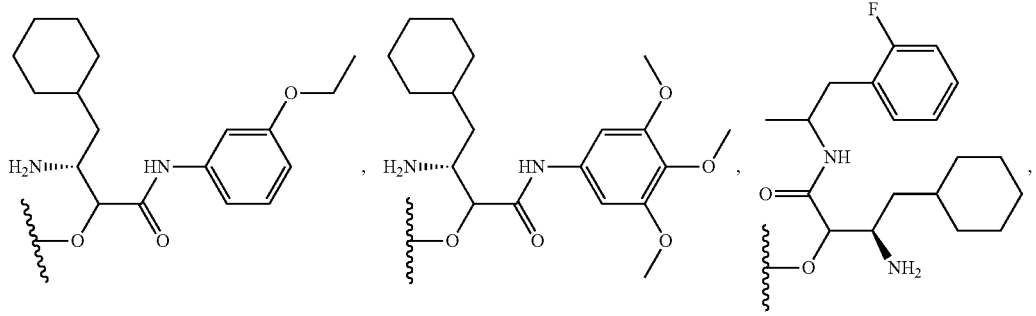
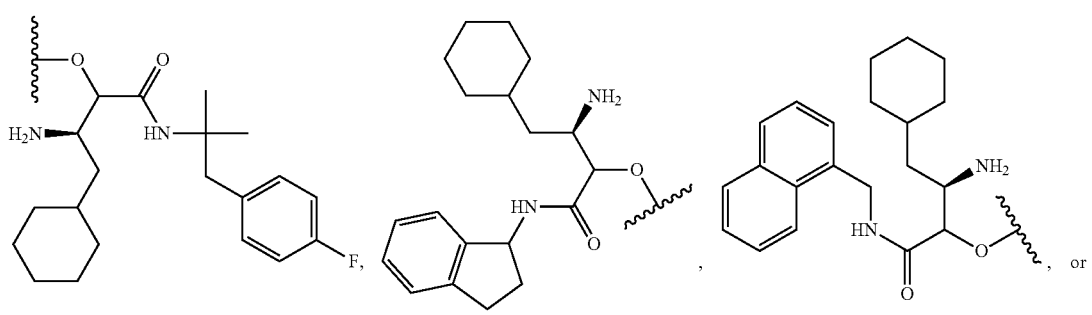
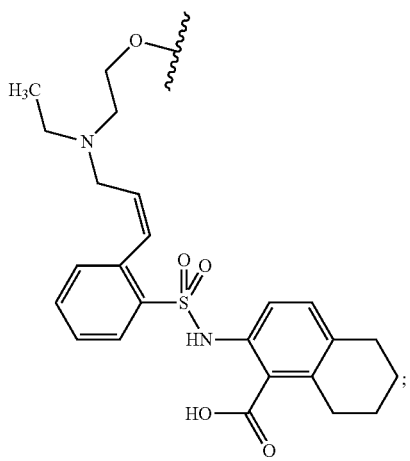
wherein $R_2$ is —OH or methoxy; and $R_3$ is H, —OH or methoxy.
In certain embodiments, W is
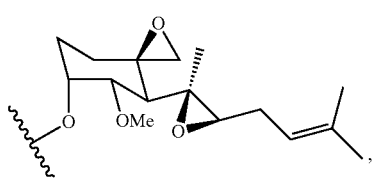
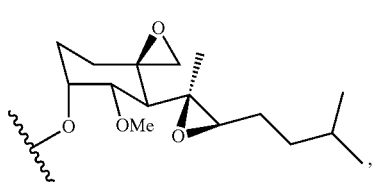
-continued
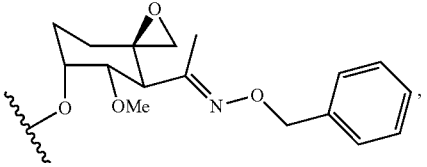
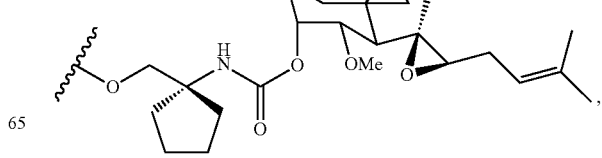

-continued
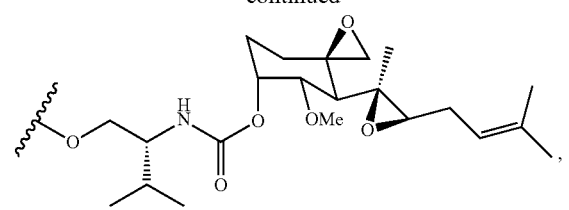
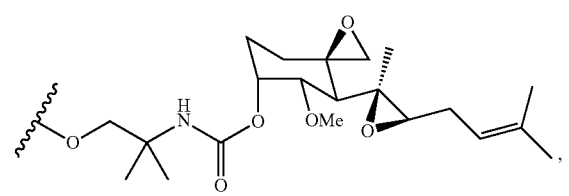
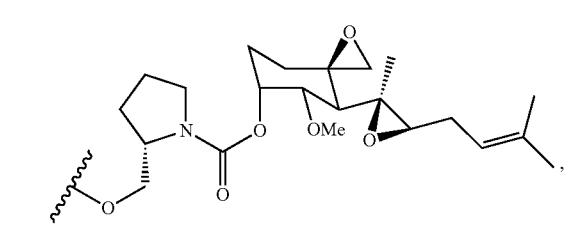
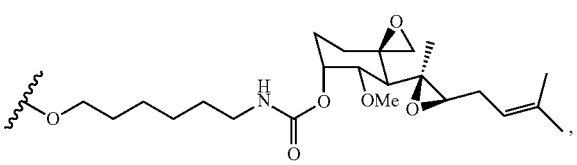
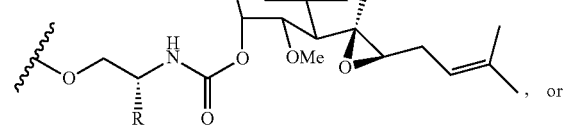
, or
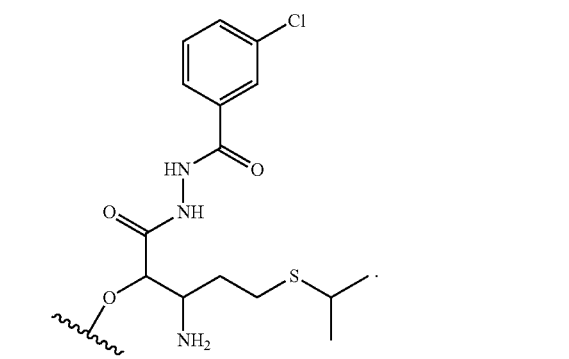
In certain embodiments, W is
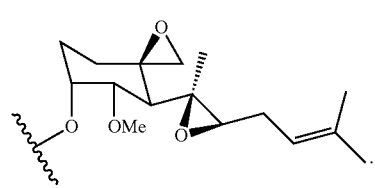
In certain embodiments, -Q-X—Y— is
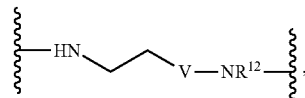
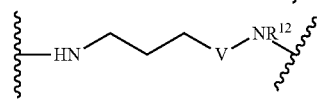
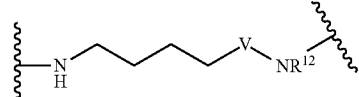
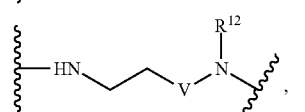
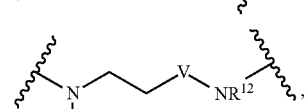
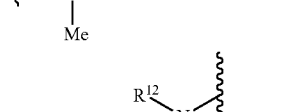
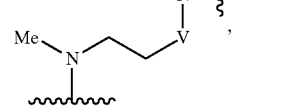
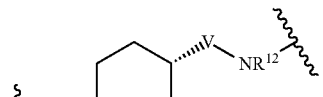
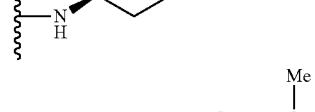
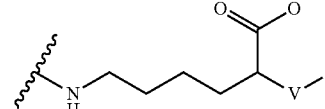
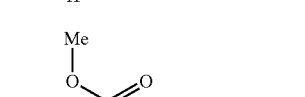
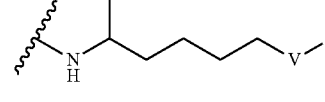
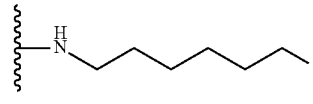
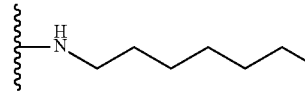
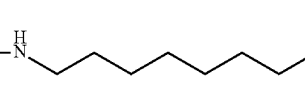

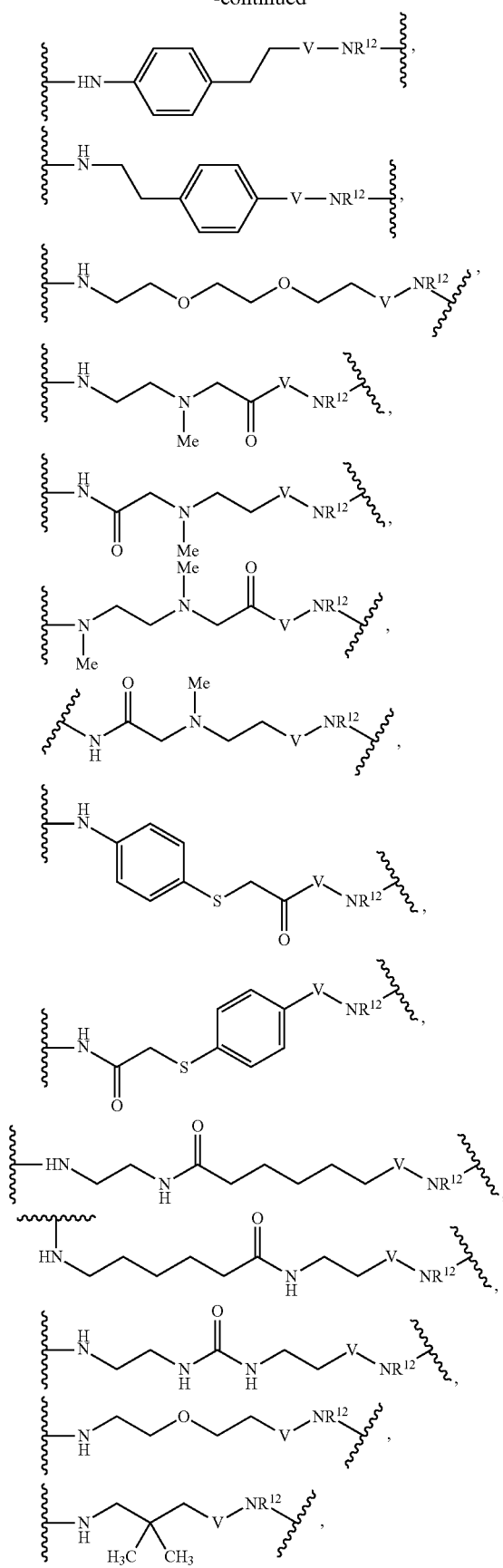
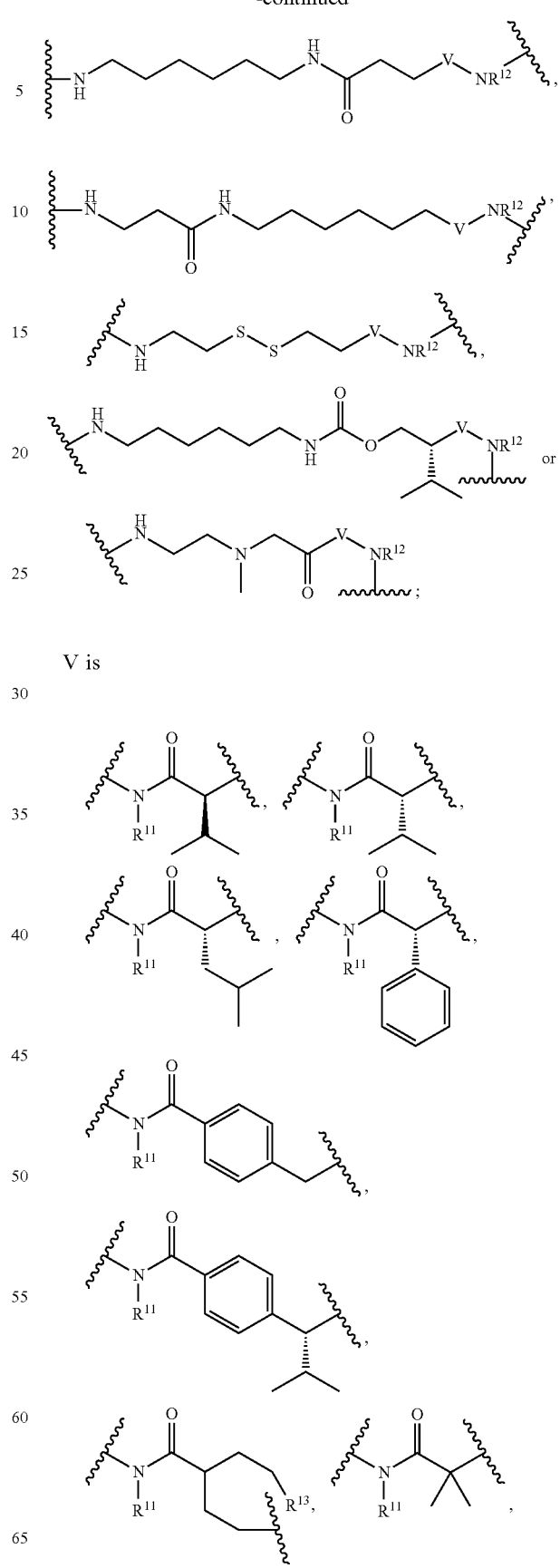
V is

-continued

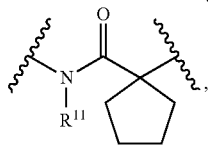

or a bond;
R$^{12}$ is H or Me; or R$^{12}$ taken together with R$^{14}$ forms a piperidine ring;
R$^{11}$ is H or Me; and
R$^{13}$ taken together with R$^{12}$ forms a piperidine ring.

In certain embodiments, Z is H$_2$N-AA$_6$-C(O)—; AA$_6$ is glycine; Q-X—Y is

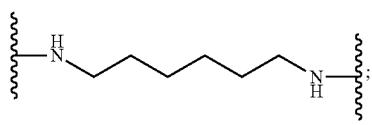

and W is

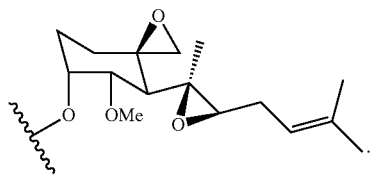

In certain embodiments, Z is H; Q-X—Y is

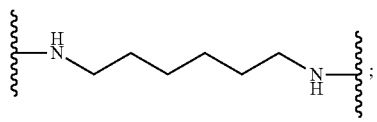 [SMILES: *NCCCCCCN*]

and
W is

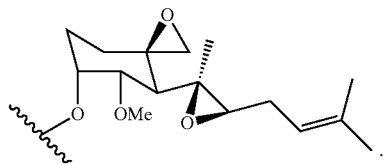

In certain embodiments, Z is H$_2$N-AA$_6$-C(O)—; AA$_6$ is glycine; Q-X—Y is

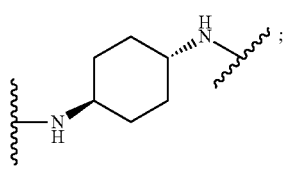 [SMILES: *N[C@H]1CC[C@H](N*)CC1]

and W is

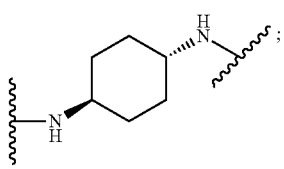 [SMILES: *N[C@H]1CC[C@H](N*)CC1]

In certain embodiments, Z is H; Q-X—Y is

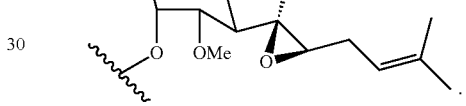

and W is

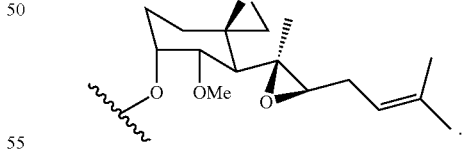

In certain embodiments, Z is H$_2$N-AA$_6$-C(O)—; AA$_6$ is glycine; Q-X—Y is;

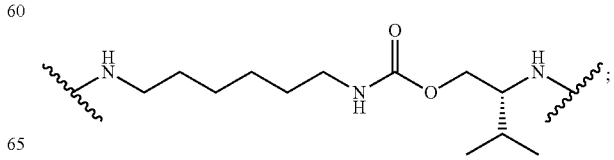

and W is

In certain embodiments, Z is H; Q-X—Y is and W is

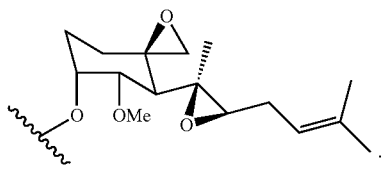

Exemplary polymers of the invention have been described in U.S. Pat. No. 4,997,878 to Bock et al, U.S. Pat. No. 5,037,883 to Kopecek et al. U.S. Pat. No. 5,258,453 to Kopecek et al, U.S. Pat. No. 6,464,850 to Zhang et al., U.S. Pat. No. 6,803,438 to Brocchini et al., each of which is incorporated by reference in its entirety. Additional exemplary polymers have been described in Subr et al., J Controlled Release, 18, 123-132 (1992). Exemplary peptides of the invention have been described in U.S. Pat. No. 6,835,807 to Susaki et al, U.S. Pat. No. 6,291,671 to Inoue et al, U.S. Pat. No. 6,811,996 to Inoue et al, U.S. Pat. No. 7,041,818 to Susaki et al, U.S. Pat. No. 7,091,186 to Senter et al, U.S. Pat. No. 7,553,816 to Senter et al. each of which is incorporated by reference in its entirety. Additional exemplary peptides and their cleavage have been described in Shiose et al. *Biol. Pharm. Bull.* 30(12) 2365-2370 (2007) and Shiose et al. Bioconjugate Chem. 20(1) 60-70 (2009).

In some embodiments, the method of synthesis of the polymer may lead to the coupling of two or more polymer chains and may increase the weight average molecular weight of the polymer conjugate. It is further recognized that if this coupling occurs, the linkages will be biodegradable.

Exemplary MetAP2 inhibitors have been described in U.S. Pat. No. 6,242,494 to Craig et al, U.S. Pat. No. 6,063,812 to Hong et al, U.S. Pat. No. 6,887,863 to Craig et al, U.S. Pat. No. 7,030,262 to BaMaung et al., U.S. Pat. No. 7,491,718 to Comess et al, each of which is incorporated by reference in its entirety. Additional exemplary MetAP2 inhibitors have been described in Wang et al. "Correlation of tumor growth suppression and methionine aminopeptidase-2 activity blockade using an orally active inhibitor," *PNAS* 105(6) 1838-1843 (2008); Lee at al. "Design, Synthesis, and Antiangiogenic Effects of a Series of Potent Novel Fumagillin Analogues," *Chem. Pharm. Bull.* 55(7) 1024-1029 (2007); Jeong et al. "Total synthesis and antiangiogenic activity of cyclopentane analogues of fumagillol," *Bioorganic and Medicinal Chemistry Letters* 15, 3580-3583 (2005); Arico-Muendel et al. "Carbamate Analogues of Fumagillin as Potent, Targeted Inhibitors of Methionine Aminopeptidase-2," *J. Med. Chem.* 52, 8047-8056 (2009); and International Publication No. WO 2010/003475 to Heinrich et al.

Because the scientific literature has established a causal link between inhibition of MetAP2 and the resultant inhibition of endothelial cell proliferation and angiogenesis, it can be inferred that the MetAP2 inhibitors described herein possess antiangiogenic activity. As angiogenesis inhibitors, such compounds are useful in the treatment of both primary and metastatic solid tumors, including carcinomas of breast, colon, rectum, lung, oropharynx, hypopharynx, esophagus, stomach, pancreas, liver, gallbladder and bile ducts, small intestine, urinary tract (including kidney, bladder, and urothelium), female genital tract (including cervix, uterus, and ovaries as well as choriocarcinoma and gestational trophoblastic disease), male genital tract (including prostate, seminal vesicles, testes, and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, and meninges (including astrocytomas, gliomas, glioblastomas, retinoblastomas, neuromas, neuroblastomas, Schwannomas, and meningiomas). Such compounds may also be useful in treating solid tumors arising from hematopoietic malignancies such as leukemias (i.e., chloromas, plasmacytomas and the plaques and tumors of mycosis fungosides and cutaneous T-cell lymphoma/leukemia) as well as in the treatment of lymphomas (both Hodgkin's and non-Hodgkin's lymphomas). In addition, these compounds may be useful in the prevention of metastases from the tumors described above either when used alone or in combination with radiotherapy and/or other chemotherapeutic agents. The compounds of the invention can also be useful in the treatment of the aforementioned conditions by mechanisms other than the inhibition of angiogenesis.

Further uses include the treatment and prophylaxis of diseases such as blood vessel diseases such as hemagiomas, and capillary proliferation within atherosclerotic plaques; Osier-Webber Syndrome; myocardial angiogenesis; plaque neovascularization; telangiectasia; hemophiliac joints; angiofibroma; and wound granulation. Other uses include the treatment of diseases characterized by excessive or abnormal proliferation of endothelial cells, including not limited to intestinal adhesions, Crohn's disease, atherosclerosis, scleroderma, and hypertrophic scars, i.e., keloids. Another use is as a birth control agent, by inhibiting ovulation and establishment of the placenta. The compounds of the invention are also useful in the treatment of diseases that have angiogenesis as a pathological consequence such as cat scratch disease (*Rochele minutesalia quintosa*) and ulcers (*Helicobacter pylori*). The compounds of the invention are also useful to reduce bleeding by administration prior to surgery, especially for the treatment of resectable tumors.

Another aspect of the present invention relates to a pharmaceutical composition, comprising any one of the compounds described herein, and a pharmaceutically acceptable carrier or excipient. In certain embodiments, the pharmaceutical composition comprises DMSO.

Yet another aspect of the present invention relates to a method of treating a disease or condition by administering to a subject in need thereof a therapeutically effective amount of a compound or composition described herein, wherein the disease is cancer, a disease characterized by irregular vasculature, a disease or condition characterized by hyperpermeable vasculature, cardiovascular, coronary vasculitis, pleural effusion, IL-2 associated edema, edema, or transplant rejection. In certain embodiments, the disease is a solid tumor. In certain embodiments, the solid tumor is a melanoma, metastases, adenocarcinoma, sarcoma, thymoma, lymphoma, lung tumor, liver tumor, colon tumor, kidney tumor, non-Hodgkin's lymphoma, Hodgkin's lymphoma, leukemia, uterine tumor, breast tumor, testicular tumor, bone tumor, muscle tumor, tumor of the head and neck, esophagus tumor, thyroid tumor, nasopharyngeal tumor, endocrine tumor, brain tumor, tumor of the skin, soft tissue tumor, tumor of the placenta or gastric tumor.

Another aspect of the present invention relates to a method of treating an angiogenic disease by administering to a subject in need thereof a therapeutically effective amount of a compound or composition described herein.

Another aspect of the present invention relates to a method of treating cancer by administering to a subject in need thereof a therapeutically effective amount of a compound or composition described herein. In certain embodiments, the cancer is adenocarcinoma, anal, astrocytoma, bladder, blood, bone, brain, breast, carcinoma, colon, cervical, endocrine, endometrial, esophageal, eye, gastric, genital, head and neck, hemangioma, non-Hodgkin's lymphoma, Hodgkin's lymphoma, kidney, laryngeal, leukemia, liver, lung, lymphoma, melanoma, mesothelioma, metastatic, mouth, muscle, myeloma, nasal, nasopharyngeal, oral, ovarian, pancreatic, penile, placenta, prostate, rectal, renal, sarcoma, skin, soft tissue, testicular, throat, thymoma, thyroid, transitional cell, ureter, uterine or vaginal.

Another aspect of the present invention relates to a method of treatment or inhibition of an undesirable proliferation of cells by administering to a subject in need thereof a therapeutically effective amount of a compound or composition described herein.

The compounds of the present invention are useful in inhibiting the proliferation of endothelial cells, tumor cells, smooth muscle cells, metastatic cells and others both in vitro and in vivo. Of particular interest is the prevention or inhibition of endothelial cell differentiation into capillary structures. The endothelial cells amenable to inhibition by the compounds of the invention are present at several sites in a mammal and include but are not limited to dermis, epidermis, endometrium, retina, surgical sites, gastrointestinal tract, liver, kidney, reproductive system, skin, bone, muscle, endocrine system, brain, lymphoid system, central nervous system, respiratory system, umbilical cord, breast tissue, urinary tract and the like. The methods of treatment of the present invention using the compounds described herein are particularly useful in preventing or inhibiting endothelial cell proliferation at sites of irregular vasculature, hyperpermeable vasculature, inflammation and tumorigenesis.

The compounds of the invention are particularly useful in methods of inhibiting tumorigenesis in a mammal. Tumors which may be prevented or inhibited by preventing or inhibiting tumor cell proliferation with the compound include but are not limited to melanoma, metastases, adenocarcinoma, sarcomas, thymoma, lymphoma, lung tumors, liver tumors, colon tumors, kidney tumors, non-Hodgkins lymphoma, Hodgkins lymphoma, leukemias, multiple myeloma, uterine tumors, breast tumors, prostate tumors, renal tumors, ovarian tumors, pancreatic tumors, brain tumors, testicular tumors, bone tumors, muscle tumors, tumors of the placenta, gastric tumors and the like.

In certain embodiments, the subject is a vertebrate. In certain embodiments, the vertebrate is a mammal. In certain embodiments, the mammal is a human.

In providing a mammal with one or more of the compounds described herein, the dosage of administered compound(s) will vary depending upon such factors as the mammal's age, weight, height, sex, general medical condition, previous medical history, disease progression, tumor burden, route of administration, formulation and the like. For example, a suitable dose of a compound of the invention for a mammal in need of treatment as described herein is in the range of about 0.01 mg to about 2000 mg compound per kilogram of body weight. In addition, due to the effects of being bound to the polymer, agents may be administered at lower doses than typically used in the treatment of a particular disorder. Surprisingly, in some embodiments the polymer conjugates of the invention are more active on a weight/weight basis than the corresponding small molecules.

The present invention also encompasses combination therapy in which compounds described herein are used in combination with, for example, a chemotherapeutic agent, or an anti-hypertensive agent. The therapeutic agents may also be conjugated to a polymer.

The route of administration may be intravenous (I.V.), intramuscular (I.M.), subcutaneous (S.C.), intradermal (I.D.), intraperitoneal (I.P.), intrathecal (I.T.), intrapleural, intrauterine, rectal, vaginal, topical, intratumor and the like.

Definitions

The term "alkyl" refers to a fully saturated branched or unbranched carbon chain radical having the number of carbon atoms specified, or up to 30 carbon atoms if no specification is made. For example, a "lower alkyl" refers to an alkyl having from 1 to 10 carbon atoms, such as methyl, ethyl, propyl, butyl, pentyl, hexyl, heptyl, and octyl, and those which are positional isomers of these alkyls. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In certain embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, certain cycloalkyls have from 3-10 carbon atoms in their ring structure, and may have 5, 6, or 7 carbons in the ring structure.

Unless the number of carbons is otherwise specified, "lower alkyl", as used herein, means an alkyl group, as defined above, but having from one to ten carbons, or from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, certain alkyl groups are lower alkyls. In certain embodiments, a substituent designated herein as alkyl is a lower alkyl.

The term "carbocycle", as used herein, refers to an aromatic or non-aromatic ring in which each atom of the ring is carbon.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

"Alkenyl" refers to any branched or unbranched unsaturated carbon chain radical having the number of carbon atoms specified, or up to 26 carbon atoms if no limitation on the number of carbon atoms is specified; and having 1 or more double bonds in the radical. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl and tetracosenyl, in their various isomeric forms, where the unsaturated bond(s) can be located anywhere in the radical and can have either the (Z) or the (E) configuration about the double bond(s).

The term "alkynyl" refers to hydrocarbyl radicals of the scope of alkenyl, but having one or more triple bonds in the radical.

The terms "alkoxyl" or "alkoxy" as used herein refers to an alkyl group, as defined below, having an oxygen radical attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_1$, where m and $R_1$ are described below.

The terms "heterocyclyl" or "heterocyclic group" refer to 3- to 10-membered ring structures, more preferably 3- to 7-membered rings, whose ring structures include one to four heteroatoms. Heterocycles can also be poly cycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfmyl, ether, alkylthio, sulfonyl, ketone, aldehyde, ester, a heterocyclyl, an aromatic or heteroaromatic moiety, —$CF_3$, —CN, or the like.

The term "alkylthio" refers to an alkyl group, as defined above, having a sulfur radical attached thereto. In certain embodiments, the "alkylthio" moiety is represented by one of —(S)-alkyl, —(S)-alkenyl, —(S)-alkynyl, and —(S)—$(CH_2)_m$—$R_1$, wherein m and $R_1$ are defined below. Representative alkylthio groups include methylthio, ethylthio, and the like.

As used herein, the term "nitro" means —$NO_2$; the term "halogen" designates F, Cl, Br or I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formulae:

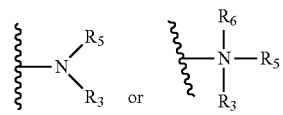

wherein $R_3$, $R_5$ and $R_6$ each independently represent a hydrogen, an alkyl, an alkenyl, —$(CH_2)_m$—$R_1$, or $R_3$ and $R_5$ taken together with the N atom to which they are attached complete a heterocycle having from 4 to 8 atoms in the ring structure; $R_1$ represents an alkenyl, aryl, cycloalkyl, a cycloalkenyl, a heterocyclyl or a polycyclyl; and m is zero or an integer in the range of 1 to 8. In certain embodiments, only one of $R_3$ or $R_5$ can be a carbonyl, e.g., $R_3$, $R_5$ and the nitrogen together do not form an imide. In certain embodiments, $R_3$ and $R_5$ (and optionally $R_6$) each independently represent a hydrogen, an alkyl, an alkenyl, or —$(CH_2)_m$—$R_1$. Thus, the term "alkylamine" as used herein means an amine group, as defined above, having a substituted or unsubstituted alkyl attached thereto, i.e., at least one of $R_3$ and $R_5$ is an alkyl group. In certain embodiments, an amino group or an alkylamine is basic, meaning it has a $pK_a \geq 7.00$. The protonated forms of these functional groups have $pK_a$s relative to water above 7.00.

The term "carbonyl" (C(O)) is art-recognized and includes such moieties as can be represented by the general formula:

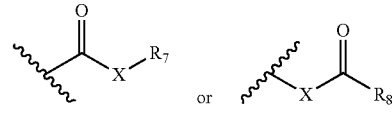

wherein X is a bond or represents an oxygen or a sulfur, and $R_7$ represents a hydrogen, an alkyl, an alkenyl, —$(CH_2)_m$—$R_1$ or a pharmaceutically acceptable salt, $R_8$ represents a hydrogen, an alkyl, an alkenyl or —$(CH_2)_m$—$R_1$, where m and $R_1$ are as defined above. Where X is an oxygen and $R_7$ or $R_8$ is not hydrogen, the formula represents an "ester". Where X is an oxygen, and $R_7$ is as defined above, the moiety is referred to herein as a carboxyl group, and particularly when $R_7$ is a hydrogen, the formula represents a "carboxylic acid". Where X is an oxygen, and $R_8$ is hydrogen, the formula represents a "formate". In general, where the oxygen atom of the above formula is replaced by sulfur, the formula represents a "thiocarbonyl" group. Where X is a sulfur and $R_7$ or $R_8$ is not hydrogen, the formula represents a "thioester" group. Where X is a sulfur and $R_7$ is hydrogen, the formula represents a "thiocarboxylic acid" group. Where X is a sulfur and $R_8$ is hydrogen, the formula represents a "thioformate" group. On the other hand, where X is a bond, and $R_7$ is not hydrogen, the above formula represents a "ketone" group. Where X is a bond, and $R_7$ is hydrogen, the above formula represents an "aldehyde" group.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "sulfamoyl" is art-recognized and includes a moiety that can be represented by the general formula:

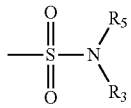

in which $R_3$ and $R_5$ are as defined above.

The term "sulfate" is art recognized and includes a moiety that can be represented by the general formula:

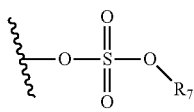

in which $R_7$ is as defined above.

The term "sulfamido" is art recognized and includes a moiety that can be represented by the general formula:

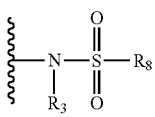

in which $R_2$ and $R_4$ are as defined above.

The term "sulfonate" is art-recognized and includes a moiety that can be represented by the general formula:

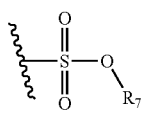

in which $R_7$ is an electron pair, hydrogen, alkyl, cycloalkyl, or aryl.

The terms "sulfoxido" or "sulfmyl", as used herein, refers to a moiety that can be represented by the general formula:

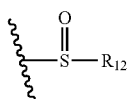

in which $R_{12}$ is selected from the group consisting of hydrogen, alkyl, alkenyl, alkynyl, cycloalkyl, heterocyclyl, aralkyl, or aryl.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

For purposes of this invention, the chemical elements are identified in accordance with the Periodic Table of the Elements, CAS version, Handbook of Chemistry and Physics, 67th Ed., 1986-87, inside cover.

The phrase "pharmaceutically acceptable" is employed herein to refer to those ligands, materials, compositions, and/or dosage forms which are, within the scope of sound medical judgment, suitable for use in contact with the tissues of human beings and animals, substantially non-pyrogenic, without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter, DMSO and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salts" refers to the relatively non-toxic, inorganic and organic acid addition salts of the inhibitor(s). These salts can be prepared in situ during the final isolation and purification of the inhibitor(s), or by separately reacting a purified inhibitor(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. (See, for example, Berge et al. (1977) "Pharmaceutical Salts", *J. Pharm. Sci.* 66:1-19)

In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of an inhibitor(s). These salts can likewise be prepared in situ during the final isolation and purification of the inhibitor(s), or by separately reacting the purified inhibitor(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

A "therapeutically effective amount" of a compound, with respect to use in treatment, refers to an amount of a compound in a preparation which, when administered as part of a desired dosage regimen (to a mammal, preferably a human) alleviates a symptom, ameliorates a condition, or slows or prevents the onset of disease conditions according to clinically acceptable standards for the disorder or condition to be treated or the cosmetic purpose, e.g., at a reasonable benefit/risk ratio applicable to any medical treatment. A "therapeutically effective amount" is synonymous with "efficacious dose".

A "patient" or "subject" to be treated by the subject method can mean either a human or non-human subject.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "amino acid" is intended to embrace all compounds, whether natural or synthetic, which include both an amino functionality and an acid functionality, including amino acid analogs and derivatives. In certain embodiments, the amino acids contemplated in the present invention are those naturally occurring amino acids found in proteins, or the naturally occurring anabolic or catabolic products of such amino acids, which contain amino and carboxyl groups. Naturally occurring amino acids are identified throughout by the conventional three-letter and/or one-letter abbreviations, corresponding to the trivial name of the amino acid, in accordance with the following list. The abbreviations are accepted in the peptide art and are recommended by the IUPAC-IUB commission in biochemical nomenclature.

By the term "amino acid residue" is meant an amino acid. In general the abbreviations used herein for designating the naturally occurring amino acids are based on recommendations of the IUPAC-IUB Commission on Biochemical Nomenclature (see Biochemistry (1972) 11:1726-1732). For instance Met, He, Leu, Ala and Gly represent "residues" of methionine, isoleucine, leucine, alanine and glycine, respectively. By the residue is meant a radical derived from the corresponding a-amino acid by eliminating the OH portion of the carboxyl group and the H portion of the a-amino group.

The term "amino acid side chain" is that part of an amino acid residue exclusive of the backbone, as defined by K. D. Kopple, "Peptides and Amino Acids", W. A. Benjamin Inc., New York and Amsterdam, 1966, pages 2 and 33; examples of such side chains of the common amino acids are $-CH_2CH_2SCH_3$ (the side chain of methionine), $-CH_2(CH_3)-CH_2CH_3$ (the side chain of isoleucine), $-CH_2CH(CH_3)_2$ (the side chain of leucine) or H— (the side chain of glycine). These side chains are pendant from the backbone Cα carbon.

The term "peptide," as used herein, refers to a sequence of amino acid residues linked together by peptide bonds or by modified peptide bonds. The term "peptide" is intended to encompass peptide analogs, peptide derivatives, peptidomimetics and peptide variants. The term "peptide" is understood to include peptides of any length. Peptide sequences set out herein are written according to the generally accepted convention whereby the N-terminal amino acid is on the left, and the C-terminal amino acid is on the right (e.g., $H_2N$-$AA_1$-$AA_2$-$AA_3$-$AA_4$-$AA_5$-$AA_6$-$CO_2H$).

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis or by derivation with a chiral auxiliary, where the resulting diastereomeric mixture is separated and the auxiliary group cleaved to provide the pure desired enantiomer. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomer.

EXEMPLIFICATION

The invention now being generally described, it will be more readily understood by reference to the following examples, which are included merely for purposes of illustration of certain aspects and embodiments of the present invention, and are not intended to limit the invention.
General Procedures Tangential Flow Filtration (TFF) was used to purify the polymer products of the invention. TFF was performed with a Pall Minimate™ Capsule and Minimate™ TFF system according to the manufacturer's instructions. Either a Minimate TFF Capsule with 5 kDa Omega membrane (5K) or Minimate TFF Capsule with 10 kDa Omega membrane (10K) cartridge was used for purification. In all cases, the permeate was discarded and the retentate lyophilized to yield the polymer product. Structures of products were confirmed by $^1H$ NMR, small molecules were also characterized by MS. Polymer weights reported in the examples were not corrected for water content.

Carbamoylfumagillol and chloroacetylcarbamoylfumagillol can be prepared according to the methods disclosed in U.S. Pat. No. 5,166,172 (Kishimoto, et al., incorporated herein by reference). p-Nitrophenyl fumagill-6-yl carbonate can be prepared according to published procedures. (See Han, C. et al. Biorg. Med. Chem. Lett. 2000, 10, 39-43). MA-GFLG-ONp can be prepared according to the methods disclosed in U.S. Pat. No. 5,258,453 (Kopecek et al. incorporated herein by reference.)

Example 1: Synthesis of poly(HPMA-co-MA-GFLG-ONp)

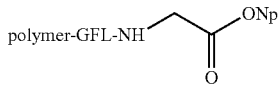

A mixture of hydroxypropylmethacrylamide (HPMA, 22.16 g, 155 mmol), N-methyacryl-gly-phe-leu-gly p-nitrophenyl ester (MA-GFLG-ONp, 10.00 g, 17.19 mmol), AIBN (1.484 g, 9.037 mmol) and acetone (225 g) was degassed (freeze, pump, thaw, 4 cycles). The resulting reaction mixture was stirred at 50° C. for 48 hours, then cooled to room temperature. The desired product was purified by trituration with acetone, then dried under vacuum to yield 17.6 g of poly(HPMA-co-MA-GFLG-ONp) as a white solid. The structure was verified by $^1$H NMR and the product shown to be free from substantial impurities (e.g., p-nitrophenol). Based on UV absorbance, the copolymer contained 0.47 mmoles of p-nitrophenyl ester per gram of polymer. The copolymer of this example is used in most of the subsequent examples. A wide range of copolymers based on different monomers and/or monomer ratios may be made following this procedure by adjusting the stoichiometry and/or using different monomers.

Example 2. Synthesis of poly(HPMA-co-MA-GFLG-OH)

Poly(HPMA-co-MA-GFLG-ONp) (700 mg) was added portionwise to a solution of 0.1 M NaOH (11.3 mL) at 0° C. The yellow reaction mixture was stirred at 0° C. for 0.5 hours, then at room temperature for 4 hours. One-half of the solution was acidified with 0.1 M HCl to pH=6. The aqueous phase was extracted with ethyl acetate to remove excess p-nitrophenol. The aqueous phase was lyophilized to afford poly(HPMA-co-MA-GFLG-OH) as a colorless solid (360 mg).

Example 3. Synthesis of poly(HPMA-co-MA-GFLG-NHCH2CH2N(Me)BOC) and General Procedure A

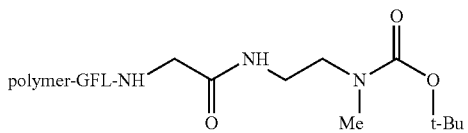

A solution of poly(HPMA-co-MA-GFLG-ONp) (1.0 g, 0.534 mmol) in DMF (6 mL) and H$_2$O (10 mL) was added dropwise over a 15 minute interval to a solution of tert-butyl N-(2-aminoethyl)-N-methylcarbamate (0.20 g, 1.15 mmol) in water (20 mL) at 0° C. The reaction mixture was stirred at 0° C. for 15 minutes, then warmed to room temperature and stirred for 12 hours. The solvents were evaporated under reduced pressure. The resulting residue was dissolved in water (50 mL), the pH was adjusted to approximately 8.0 with 0.1 M NaOH. The solution was filtered through a VacuCap filter, then purified using TFF (10 K). The polymer-containing solution was washed (as part of the TFF process) with 25 mM NaCl solution (800 mL) to remove p-nitrophenol, the pH of the solution was adjusted to approximately 4 with 0.1 M HCl, and then washed (as part of the TFF process) with water (400 mL). The polymer solution was lyophilized to isolate the compound poly(HPMA-co-MA-GFLG-NHCH$_2$CH$_2$N(Me)BOC) as a pale yellow solid (720 mg, 71%).

Example 4. Synthesis of poly(HPMA-co-MA-GFLG-NHCH2CH2NHMe)

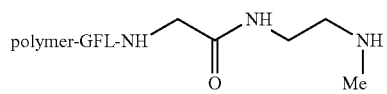

A solution of poly(HPMA-co-MA-GFLG-NHCH$_2$CH$_2$N(Me)BOC) (260 mg, 0.136 mmol) in D$_2$O (5.2 mL) was irradiated with microwave radiation at 150° C. with stirring for 6 hours. The $^1$H NMR of this material indicated that deprotection of BOC group had occurred. The aqueous solution was lyophilized to isolate the poly(HPMA-co-MA-GFLG-NHCH$_2$CH$_2$NHMe) as a pale yellow solid (210 mg, 85%).

Example 5. Synthesis of N-({[2-(acetylamino)ethyl](methyl)amino}acetyl)carbamoylfumagillol and General Procedure B

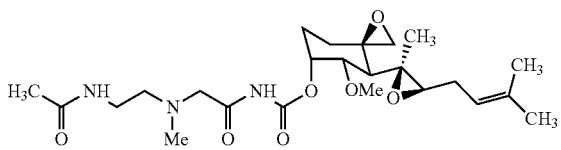

Diisopropylethylamine (DIEA) (130 mg) was added to a solution of N-[2-(methylamino)ethyl]acetamide hydrochloride (76 mg) and chloroacetylcarbamoylfumagillol (200 mg) in anhydrous DMF at 0° C. under N$_2$. The reaction mixture was allowed to warm to room temperature, and stirred for 12 hours. The solvent was removed under reduced pressure and the resulting residue was suspended in water (30 mL) and extracted with EtOAc (aqueous and organic phases from the emulsion formed were separated using a centrifuge) to remove excess chloroacetylcarbamoylfumagillol. Nitrogen was passed through the aqueous solution to reduce the residual level of EtOAc. The product was purified by flash chromatography (methanol/methylene chloride) to yield N-({[2-(acetylamino)ethyl](methyl)amino}acetyl)carbamoylfumagillol (75 mg) as an off-white foam.

Example 6. BocNHCH$_2$CH$_2$N(Me)CH$_2$C(O)NHC(O)$_2$-fumagill-6-yl (Alkylation of N—BOC, N'-methylethylenediamine with chloroacetylcarbamoylfumagillol)

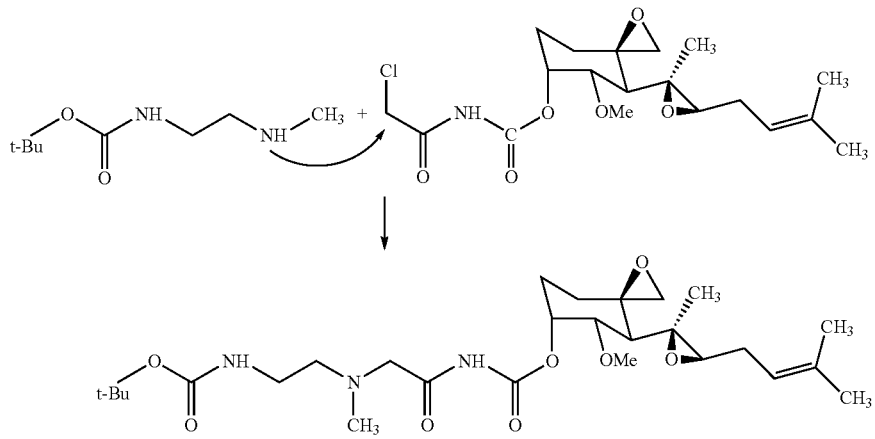

A solution of TNP-470 (0.2 g) and DIEA (0.105 g) in DMF (3 mL) was cooled to 0° C. A solution of tert-butyl N-[2-(methylamino)ethyl]carbamate (0.105 g) in DMF (3 mL) was added, and the mixture was stirred for 3 hours at 0° C. and then overnight. The reaction was diluted with ethyl acetate and extracted with water. The aqueous phase was back extracted with ethyl acetate, and the combined organic phases were extracted with brine, dried (MgSO$_4$) and evaporated to afford an oil. Purification by silica gel chromatography (methanol/methylene chloride) and evaporation of the product fractions gave BocNHCH$_2$CH$_2$N(Me)CH$_2$C(O)NHC(O)$_2$-fumagill-6-yl a white foam (0.16 g, 60%).

Example 7. Reaction of tert-butyl N-[2-aminoethyl] carbamate with chloroacetylcarbamoylfumagillol

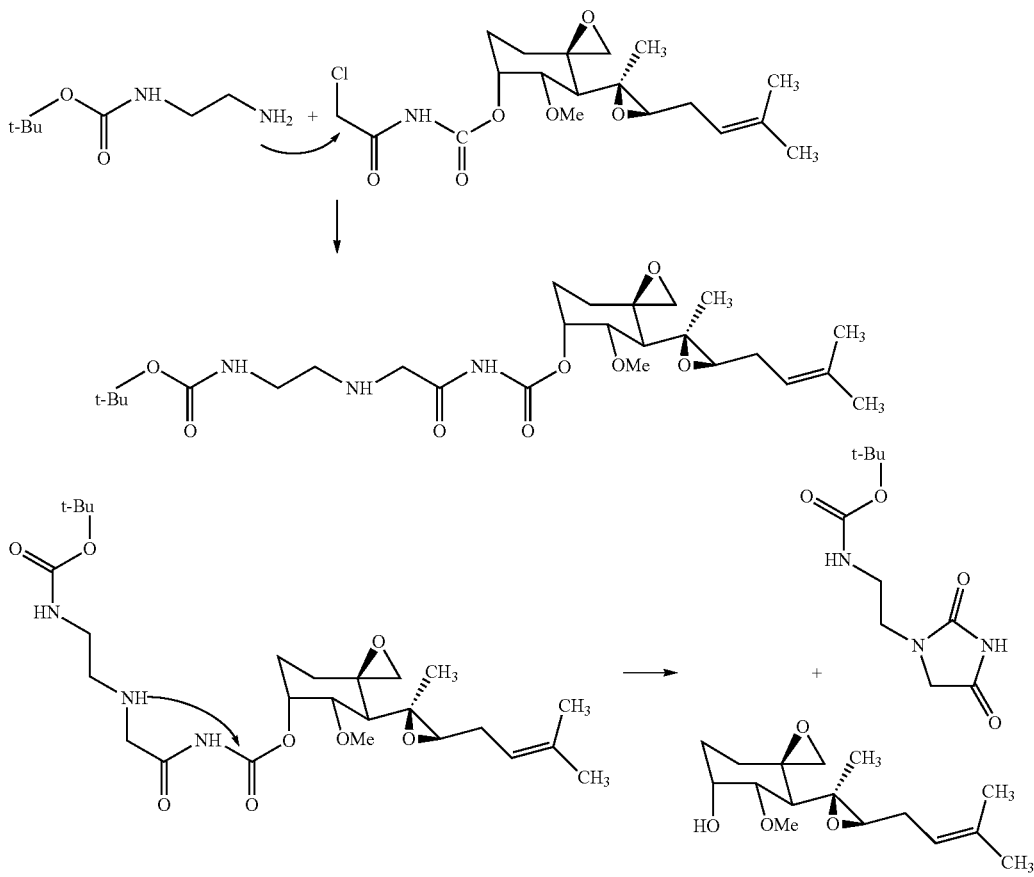

A 30 uL aliquot of a 1 M solution of Boc-ethylenediamine in DMF was added to DMF (270 uL). The solution was cooled to 0° C., and a solution of TNP-470 (48 mg) in DMF (600 uL) was added dropwise over 2 minutes. The reaction was monitored by LC/MS. The largest amount of the desired alkylation product observed was 34%. Carbamoylfumagillol was also produced. The ratio of desired product to carbamoylfumagillol was 1.0 to 0.4. Attempted isolation of the desired product resulted in the isolation of hydantoin and fumagillol.

Example 8. Synthesis poly(HPMA-co-MA-GFLG-NHCH$_2$CH$_2$N(Me)CH$_2$C(O)NHC(O)$_2$-fumagill-6-yl)

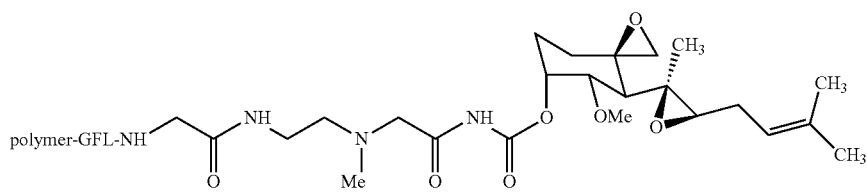

General Procedure B was followed using poly(HPMA-co-MA-GFLG-NHCH$_2$CH$_2$NHMe) (105 mg, 0.058 mmol) and chloroacetylcarbamoylfumagillol (46 mg, 0.114 mmol) in DMF (5 mL) to which DIEA (29.5 mg, 0.228 mmol) was added N$_2$. The product was purified using TFF (5 K) by washing with water (150 mL) to remove DIEA hydrochloride. The polymer solution was lyophilized to obtain the polymer conjugate (60 mg, 48%) as a pale yellow solid.

Example 9. Synthesis of pol(HPMA-co-MA-GFLG-NHCH$_2$CH$_2$NH$_2$HCl) and General Procedure C for the Reaction of Diamines with poly(HPMA-co-MA-GFLG-ONp)

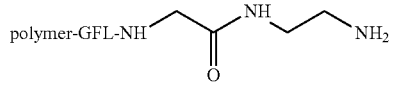

A solution of ethylenediamine (0.33 g, 5.49 mmole) in water (20 mL), pH 11.7, was adjusted to pH 9.1 by the addition of 37% aq HCl (17-18 drops). The solution was cooled in an ice bath and poly(HPMA-co-MA-GFLG-ONp) (1.03 g) in DMF (6 mL) was added dropwise over 20 minutes while maintaining the temperature below 4° C. The solution was stirred 20 minutes at 4° C., 50 minutes at room temperature to give a lemon yellow solution, pH 8.1. The solution was evaporated at 40° C. H$_2$O (3×10 mL) was added and evaporated. The product was diluted with water (60 mL), the solution adjusted with NaOH to pH 8.0. The solution was filtered through a VacuCap filter and purified by TFF as follows. The polymer solution was first washed with 25 mM NaCl solution (800 mL) to remove p-nitrophenol. The solution was washed with water (400 mL) then adjusted to pH 4 with 0.1 M HCl. The TFF retentate was collected and the filter was washed with 2×10 mL of water. The combined retentate and washes gave a polymer solution which was lyophilized to isolate the compound poly(HPMA-co-MA-GFLG-NHCH$_2$CH$_2$NH$_2$HCl) as a pale yellow solid (0.71 g, 72%).

Example 10. Synthesis of poly(HPMA-co-MA-GFLG-N(Me)CH$_2$CH$_2$NHMe-HCl)

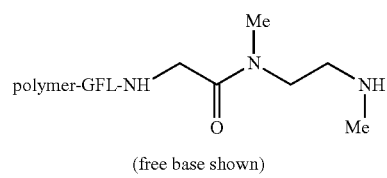

(free base shown)

General Procedure C was followed using N,N'-dimethylethylenediamine (0.47 g, 5.36 mmol) and poly(HPMA-co-MA-GFLG-ONp) (1.0 g) to yield poly(HPMA-co-MA-GFLG-N(Me)CH$_2$CH$_2$NHMe HCl) as an off-white solid (0.78 g).

Example 11. Synthesis of poly(HPMA-co-MA-GFLG-N(Me)CH$_2$CH$_2$N(Me)CH$_2$C(O)NHC(O)$_2$-fumagill-6-yl)

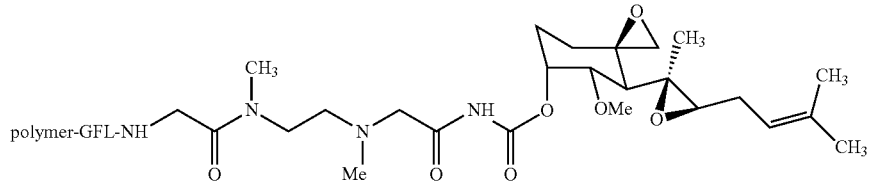

General procedure B was followed using poly(HPMA-co-MA-GFLG-N(Me)CH₂CH₂NHMe) (200 mg, 0.108 mmol) and chloroacetylcarbamoylfumagillol (86 mg, 0.213 mmol) to yield poly(HPMA-co-MA-GFLG-N(Me)CH₂CH₂N(Me)CH₂C(O)NHC(O)₂-fumagill-6-yl) as a pale yellow solid (180 mg).

Example 12. Synthesis of N-f (2R) 1-hydroxy-2-methylbutan-2-yl] carbamoylfumagillol and General Procedure D

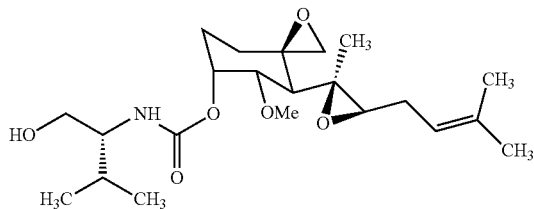

A solution of p-nitrophenyl fumagill-6-yl carbonate (400 mg, 0.89 mmol) and (R)-2-amino-3-methyl-1-butanol (280 mg, 2.71 mmol) were stirred in ethanol (10 mL) at room temperature for 12 hours. The yellow solution was concentrated and the residue purified by flash chromatography (methanol/methylene chloride) to yield N-[(2R)1-hydroxy-2-methylbutan-2-yl]carbamoylfumagillol (340 mg, 0.83 mmol) as a colorless oil.

Example 13. Synthesis of N-(6-hydroxyhexyl)carbamoylfumagillol

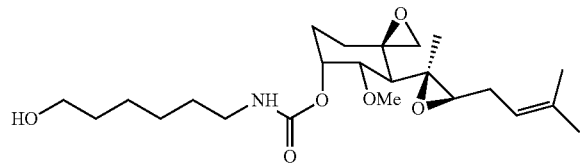

General Procedure D was followed using p-nitrophenyl fumagill-6-yl carbonate (150 mg) in ethanol (10 mL) and 6-aminohexanol (48 mg). The product was isolated as a colorless oil (110 mg, 78%).

Example 14. Synthesis of N-[l-(hydroxymethyl)cyclopentyl]carbamoylfumagillol

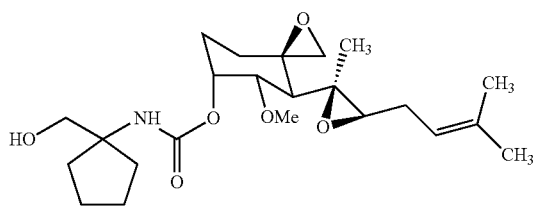

General Procedure D was followed using p-nitrophenyl fumagill-6-yl carbonate (100 mg) in ethanol (3 mL) and THF (1 mL) and cycloleucinol (52 mg) to afford N-[l-(hydroxymethyl)cyclopentyl]carbamoylfumagillol as an oil (50 mg).

Example 15. Synthesis of N-(l-hydroxy-2-methyl-propan-2-yl)carbamoylfumagillol

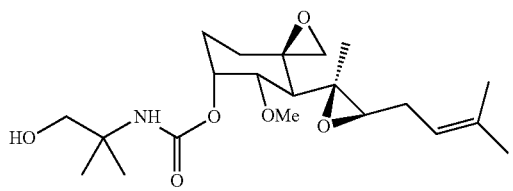

General Procedure D was followed using p-nitrophenyl fumagill-6-yl carbonate (100 mg) in ethanol (3 mL) and THF (2 mL) and 2-amino-2-methylpropanol (40 mg) to afford N-(1-hydroxy-2-methylpropan-2-yl)carbamoylfumagillol as an oil (37 mg).

Example 16. Synthesis of fumagill-6-yl (2S)-2-(hydroxymethyl)pyrrolidine-l-carboxylate

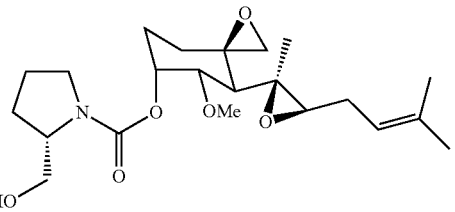

General procedure D was followed. The S-prolinol (68 mg, 0.67 mmol) was reacted with p-nitrophenyl fumagill-6-yl carbonate (150 mg, 0.335 mmol) in ethanol (4 mL) The product was purified by flash chromatography (methanol/methylene chloride) to yield fumagill-6-yl (2S)-2-(hydroxymethyl)pyrrolidine-l-carboxylate as a white foam (81 mg, 63%).

Example 17. Synthesis of fumagill-6-yl (2S)-2-({[(chloroacetyl)carbamoyl]oxy}methyl)pyrrolidine-l-carboxylate

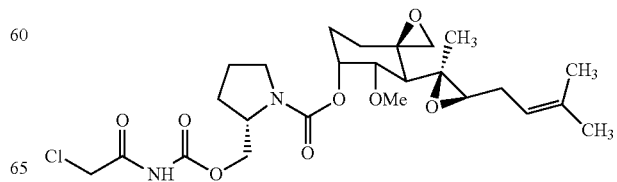

A solution of fumagill-6-yl (2S)-2-(hydroxymethyl)pyrrolidine-1-carboxylate (330 mg) in methylene chloride (2.1 mL) was cooled to 0° C. and chloroacetylisocyanate (115 mg) in methylene chloride (1.5 mL) was added dropwise. After 40 minutes, the mixture was diluted with methylene chloride (20 mL) and the organic phase washed with water (3×). The organic phase was dried (Na$_2$SO$_4$) and evaporated to yield fumagill-6-yl (2S)-2-({[(chloroacetyl)carbamoyl]oxy}methyl)pyrrolidine-1-carboxylate as a white foam (400 mg).

Example 18. Synthesis of poly[HPMA-co-MA-GFLG-NCH$_2$CH$_2$N(Me)-acetylcarbamoyl-[(2R)-1-hydroxy-3-methylbutan-2-yl]carbamoylfumagillol]

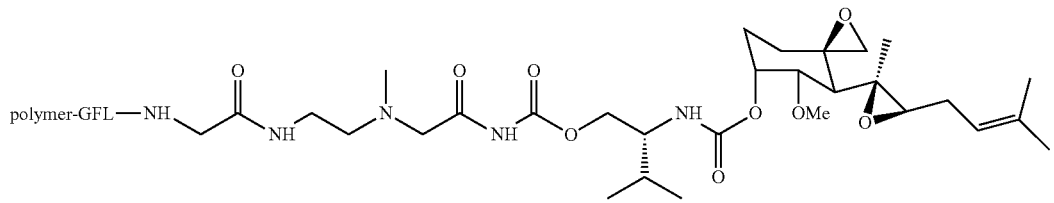

General procedure B was followed using chloroacetylcarbamoyl[(2R)-1-hydroxy-3-methylbutan-2-yl]carbamoylfumagillol (120 mg) (and poly(HPMA-co-MA-GFLG-NHCH$_2$CH$_2$NHMe) (200 mg) with DIEA (57 mg) in DMF (5 mL) to yield 2-poly[HPMA-co-MA-GFLG-NCH$_2$CH$_2$N(Me)]-acetylcarbamoyl-[1-hydroxy-3-methylbutan-2-yl]carbamoylfumagillol (200 mg, 80%).

Example 19. Synthesis of fumagill-6-yl 2-(poly[HPMA-co-MA-GFLG-NCH$_2$CH$_2$N(Me)]-acetylcarbamoylhydroxymethyl)pyrrolidine-1-carboxylate)

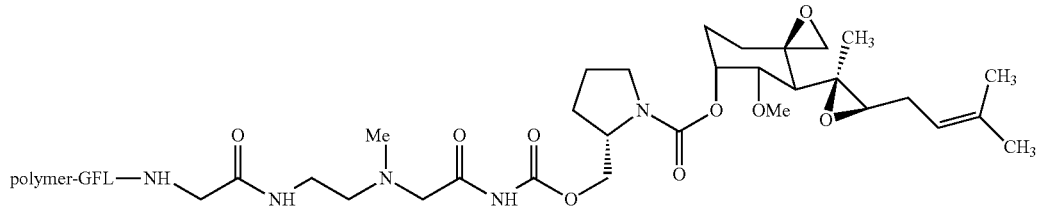

General procedure B was followed using the fumagill-6-yl (2S)-2-(chloroacetylcarbamoylhydroxymethyl)pyrrolidine-1-carboxylate (90 mg) (and poly(HPMA-co-MA-GFLG-NHCH$_2$CH$_2$NHMe) (200 mg) with DIEA (57 mg) in DMF (5 mL) to yield fumagill-6-yl 2-poly [HPMA-co-MA-GFLG-NCH$_2$CH$_2$N(Me)]-acetylcarbamoylhydroxymethyl)pyrrolidine-1-carboxylate as a pale yellow solid (150 mg, 60%).

Example 20. Synthesis of N-(6-aminohexyl)carbamoylfumagillol

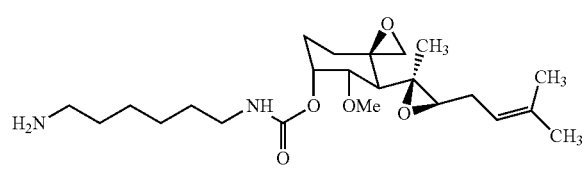

A solution of 1,6-diaminohexane (0.13 g) in methanol (8 mL) was cooled to 0° C. and p-nitrophenyl fumagill-6-yl carbonate (0.13 g) in methanol (2 mL) was added dropwise. The solvent was reduced to about 2 mL by rotary evaporation. Ethyl acetate was added and the organic phase was washed with water, 0.1 N NaOH, water, brine and dried with sodium sulfate. The solvent was evaporated and the residue dissolved in ethanol (15 mL). DL-tartaric acid (16 mg) was added, the solution was stored overnight and then evaporated to about 0.5 mL. Ether was added and a white solid formed. The solid was collected by filtration, washed with ether and dried to yield the tartrate salt of N-(6-aminohexyl)carbamoylfumagillol (74 mg).

Example 21. Synthesis of poly [HPMA-co-MA-GFLG-NH(CH$_2$)$_6$NH$_2$HCl]

General Procedure C was followed using 1,6-diaminohexane (621 mg, 5.36 mmol) and poly(HPMA-co-MA-GFLG-ONp) (1.0 g). The crude product was purified by TFF (5 K) using aqueous NaCl (25 mM) and then acidified to pH 4.0 with 0.1 M HCl and further purified by TFF with water to yield poly[HPMA-co-MA-GFLG-NH(CH$_2$)$_6$NH$_2$HCl] as an off-white solid (860 mg).

Example 22. Synthesis of p-nitrophenyl N-[(2R) 1-hydroxy-2-methylbutan-2-yl]carbamoylfumagill-6-yl carbonate and General Procedure E

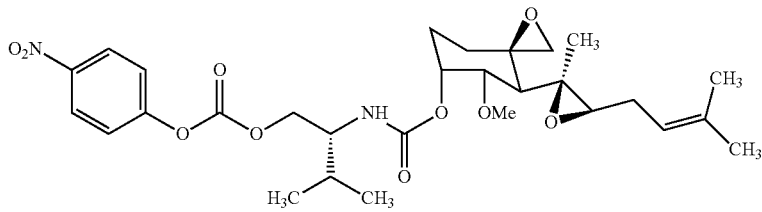

To a solution of the alcohol N-[(2R)1-hydroxy-2-methylbutan-2-yl]carbamoylfumagillol (1.11 g) in methylene chloride at 0° C. under $N_2$ was added DMAP (660 mg, 5.40 mmol) followed by the portionwise addition of p-nitrophenyl chloro formate (810 mg). The reaction mixture was stirred at 0° C. for 1 hour. The solvent was evaporated and the resulting residue was dissolved in EtOAc and washed with water, brine and dried ($Na_2SO_4$). Evaporation of EtOAc provided the crude product, which was purified by flash chromatography (silica, eluting with 100% hexanes and then with 2-30% EtOAc). The fractions containing pure product were combined and evaporated to isolate N-[(2R)1-(p-nitrophenolcarbonylhydroxy-2-methylbutan-2-yl]carbamoylfumagillol (1.25 g, 80%) as a white solid.

Example 23. Synthesis of N-[1-(p-nitrophenoxycarbonylhydroxymethyl)-2-methylpropan-2-yl)carbamoylfumagillol

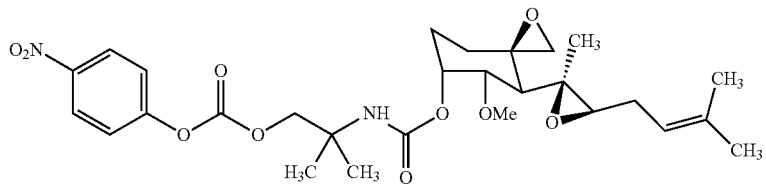

Following General Procedure E, dimethylalcohol (60 mg), p-nitrophenyl fumagill-6-yl carbonate (46 mg), and DMAP (37 mg) were reacted in methylene chloride (8 mL). The reaction mixture was diluted with ethyl acetate and washed with water (3×) and then brine. The organic phase was dried ($Na_2SO_4$) and evaporated to a yellow foam (87 mg) which was used without further purification.

Example 24. Synthesis of N-[1-(p-nitrophenoxycarbonylhydroxymethyl)cyclopentyl]carbamoylfumagillol

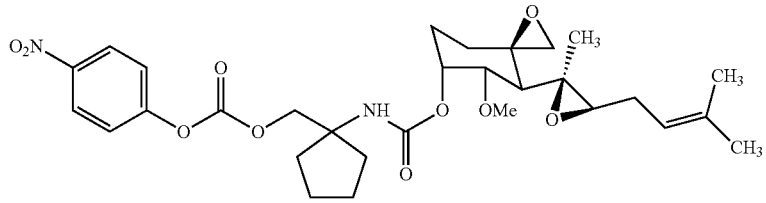

Following General Procedure E, N-[1-(hydroxymethyl)cyclopentyl]carbamoylfumagillol (product from Example 14, 74 mg), p-nitrophenyl chloroformate (53 mg), and DMAP (43 mg) were reacted in methylene chloride (5 mL). After the extractive workup, N-[1-(p-nitrophenoxycarbonylhydroxymethyl)cyclopentyl]carbamoylfumagillol (100 mg) was used without further purification.

Example 25. Synthesis of poly[HPMA-co-MA-GFLG-NH(CH$_2$)$_6$NHcarbamoyl-[1-hydroxy-3-methylbutan-2-yl]carbamoylfumagillol] and General Procedure F

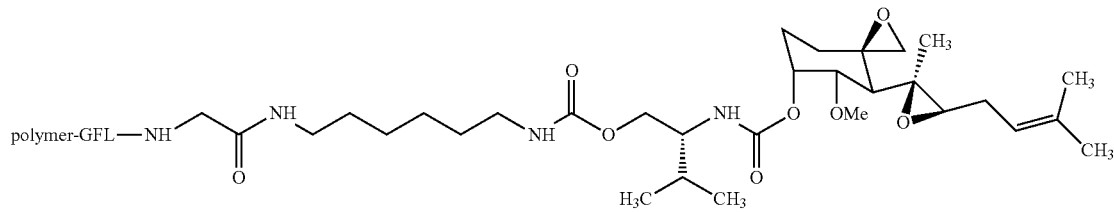

15

To a solution of polymer (400 mg) and p-nitrophenyl N-[(2R)1-hydroxy-3-methylbutan-2-yl]carbamoylfumagill-6-yl carbonate (240 mg) in DMF (8 mL) at 0° C. was added DIEA (0.11 g) dropwise. The solution was stirred at 0° C. for one hour and allowed to warm to room temperature. After 3 days, the solvent was evaporated and water (80 mL) was added. The aqueous phase was extracted with ethyl acetate (500 mL total) until none of the starting carbonate was detectable by MS. The aqueous phase was purified by TFF (10 K) and the retentate lyophilized to yield the conjugate as a white solid (380 mg, 77%).

$^1$H NMR (DMSO-d6): δ 8.25 (bs, 2H, amide-NH), 8.0 (bs, 1H, amide-NH), 7.70 (bs, 2H, amide-NH), 7.10-7.30 (m, 15H, Phenylalanine and amide-NH), 7.10 (bt, 1H, NH-Fum), 6.92 (bd, 1H, NH-Fum), 5.26 (m, H-5-Fum), 5.18 (bt, alkene-Fum), 4.50-4.80 (m, 1H, phenylalanine alpha proton), 4.0-4.21 (m, 1H, leucine alpha proton), 3.50-3.84 (m, 19H), 3.29 (s, 3H, OMe-Fum), 2.80-3.10 (m, 28H), 2.51 (d, 1H, J=4.4 Hz, H-2-Fum), 2.19 (m, 2H, allylic-Fum), 0.82-1.92 [m, 131H {1.84 (m, 2H, Fum), 1.72 (s, 3H, Fum-Me), 1.60 (s, 3H, Fum-Me), 1.09 (s, 3H, Fum-Me), 0.84 (dd, 6H, Fum-isopropyl}].

Example 26. Synthesis of poly[HPMA-co-MA-GFLG-N-(2-aminoethyl)carbamoylfumagillol]

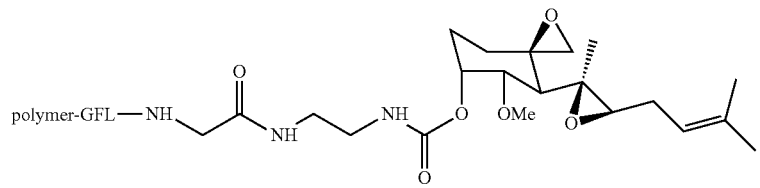

General procedure F was followed using poly(HPMA-co-MA-GFLG-NHCH$_2$CH$_2$NH$_2$HCl) (200 mg), p-nitrophenyl fumagill-6-yl carbonate (100 mg) and DIEA (57 mg) in DMF (10 mL). The product was purified by TFF (10 K) with water and lyophilized to yield the conjugate as a pale yellow solid (160 mg).

Example 27. Synthesis of poly[HPMA-co-MA-GFLG-N(Me)-(2-methylaminoethyl)carbamoylfumagillol]

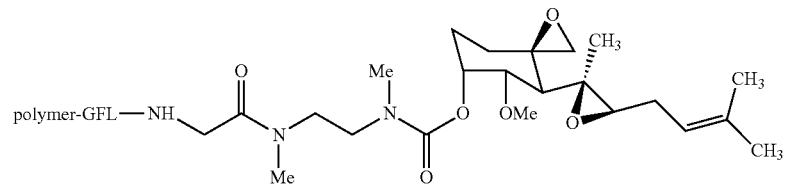

General procedure F was followed using poly(HPMA-co-MA-GFLG-N(Me)CH$_2$CH$_2$NHMe HCl) (200 mg), p-nitrophenyl fumagill-6-yl carbonate (100 mg) and DIEA (57 mg) in DMF (5 mL). The product was purified using TFF (10 K) with water and lyophilized to yield the conjugate as an off-white solid (180 mg).

Example 28. Synthesis of poly(HPMA-co-MA-GFLG-N-(2-aminoethyl)carbamoyldihydrofumagillol

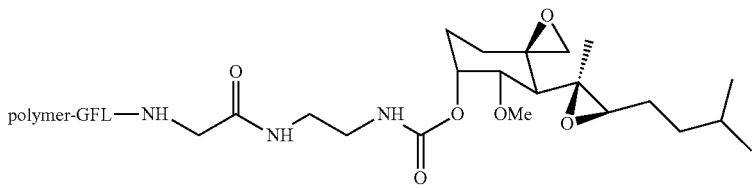

General procedure F was followed using poly(HPMA-co-MA-GFLG-NHCH$_2$CH$_2$NH$_2$ HCl) (200 mg), p-nitrophenyl dihydrofumagill-6-yl carbonate (200 mg) and DIEA (57 mg) in DMF (10 mL). The product was purified by TFF (10 K) with water (150 mL) and lyophilized to yield poly(HPMA-co-MA-GFLG-N-(2-aminoethyl)carbamoyldihydrofumagillol as a pale yellow solid (160 mg).

Example 29. Synthesis of poly[HPMA-co-MA-GFLG-N-(3-aminopropyl)carbamoylfumagillol]

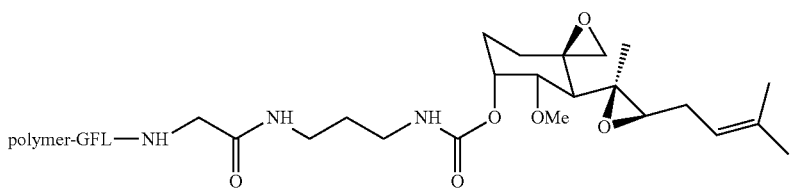

General procedure F was followed using poly(HPMA-co-MA-GFLG-NHCH$_2$CH$_2$CH$_2$NH$_2$HCl) (220 mg), p-nitrophenyl fumagill-6-yl carbonate (110 mg) and DIEA (63 mg) in DMF (6 mL). The solvent was evaporated and the resulting solution diluted with water. The aqueous phase was extracted with ethyl acetate and purified by TFF using 350 mL of water. The retentate was lyophilized to yield poly[HPMA-co-MA-GFLG-N-(3-aminopropyl)carbamoylfumagillol] as a light pink powder (200 mg).

Example 30. Synthesis of poly[HPMA-co-MA-GFLG-N-(6-aminohexyl)carbamoylfumagillol]

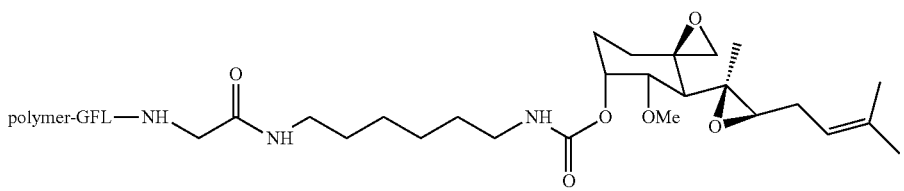

General procedure F was followed using poly[HPMA-co-MA-GFLG-N-(6-aminohexylamine.HCl)] (1.0 g), p-nitrophenyl fumagill-6-yl carbonate (0.48 g) and DIEA (0.27 g) in DMF (25 mL). The solvent was evaporated and the solution diluted with water. The aqueous phase (300 mL) was extracted with ethyl acetate (700 mL total) and purified by TFF using an additional 350 mL of water. The retentate was lyophilized to yield poly[HPMA-co-MA-GFLG-N-(6-aminohexyl)carbamoylfumagillol] as a light pink solid (0.9 g).

$^1$H NMR (DMSO-d6): δ 8.10-8.35 (m, 3H, amide-NH), 7.90-8.10 (m, amide-NH), 7.05-7.32 (m, 22H, amide-NH) 5.27 (m, H-5-Fum), 5.18 (bt, alkene-Fum), 4.60-4.90 (m, 14H), 4.50-4.60 (m, 1H, phenylalanine alpha proton), 4.10-4.30 (m, 1H, leucine alpha proton), 3.40-3.80 (m, 21H), 3.27 (s, 3H, OMe-Fum), 2.80-3.20 (m, 33H), 2.56 (d, 1H, H=3.90 Hz, H-2-Fum), 2.18 (m, 2H, allylic-Fum), 0.37-2.0 [m, 147H {1.70 (s, 3H, Fum-Me), 1.60 (s, 3H, Fum-Me), 1.07 (s, 3H, Fum-Me)}].

Example 31. Synthesis of poly[HPMA-co-MA-GFLG-N-(trans-4-aminocyclohexyl)carbamoylfumagillol]

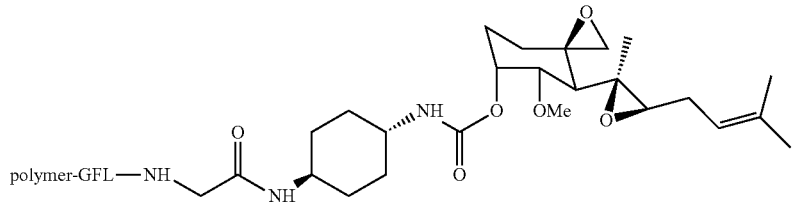

General procedure F was followed using poly[HPMA-co-MA-GFLG-N-(trans-4-aminocyclohexylamine.HCl)] (1.0 g), p-nitrophenyl fumagill-6-yl carbonate (0.48 g) and DIEA (0.27 g) in DMF 25 mL. The solvent was evaporated and the solution diluted with water. The aqueous phase (300 mL) was extracted with ethyl acetate (700 mL total) and purified by TFF using an additional 350 mL of water. The retentate was lyophilized to yield poly[HPMA-co-MA-GFLG-N-(trans-4-aminocyclohexyl)carbamoylfumagillol] as a light pink solid (0.9 g).

$^1$H NMR (DMSO-d6): δ 7.90-8.35 (m, 4H, amide-NH), 7.0-7.70 (m, 25H, Phenylalanine and amide-NH), 5.26 (m, H-5-Fum), 5.18 (bt, alkene-Fum), 4.60-4.90 (m, 14H), 4.50-4.60 (m, 1H, phenylalanine alpha proton), 4.10-4.30 (m, 1H, leucine alpha proton), 3.40-3.80 (m, 21H), 3.26 (s, 3H, OMe-Fum), 2.80-3.10 (m, 31H), 2.17 (m, 2H, allylic-Fum), 0.37-2.0 [m, 166H {1.69 (s, 3H, Fum-Me), 1.59 (s, 3H, Fum-Me), 1.07 (s, 3H, Fum-Me)}]

Example 32. Synthesis of poly[HPMA-co-MA-GFLG-N-[2-(4-aminophenyl)ethyl]carbamoylfumagillol]

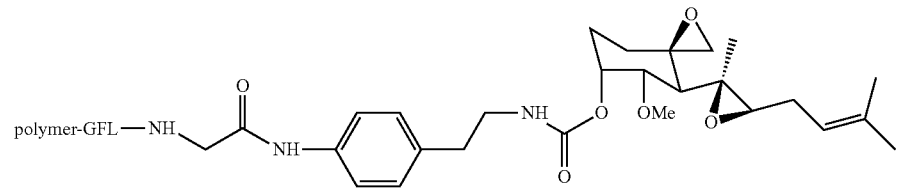

To a suspension of poly[HPMA-co-MA-GFLG-OH] (200 mg), N-[2-(4-aminophenyl)ethyl]carbamoylfumagillol] (100 mg) and DIEA (75 mg) in DMF (6 mL) at 0° C. was added EDCI (total 44 mg) in portions. The solution was allowed to warm to room temperature and stirred overnight. The solvent was evaporated, the residue was suspended in water and the suspension extracted with EtOAc (7 times, total 250 mL). The aqueous phase was purified by TFF (10 K) using water (350 mL). The retentate was lyophilized to afford the polymer as a white fluffy solid (170 mg).

Example 33. Synthesis of poly[HPMA-co-MA-GFLG-NH-2-[(2-(2-aminoethoxy)ethoxy)ethyl]carbamoylfumagillol]

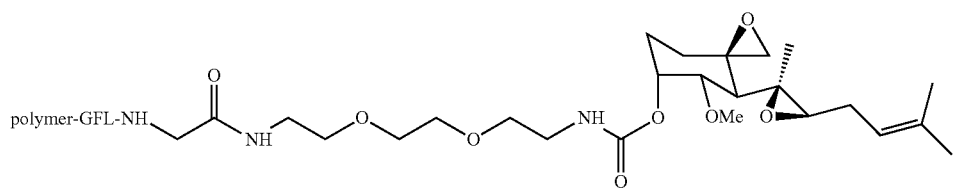

To a solution of 2,2'-(Ethylenedioxy)bis(ethylamine) (0.79 g, 5.34 mmol) in distilled water (20 mL) at 0° C. (pH=11.56) was added conc. HCl until pH of the solution was 9.01 (measured by pH meter). Poly(HPMA-co-MA-GFLG-ONp) (1.0 g, 0.534 mmol) in DMF (6 mL) and H$_2$O (10 mL) was added to the amine-containing solution dropwise over a period of 15 minutes and the reaction mixture was stirred at 0° C. for 15 minutes. The reaction mixture was then allowed to warm to room temperature and stirred for 2 hours. The pH of the solution was measured to be 8.15. The reaction mixture was diluted with distilled water (300 mL) and filtered through a VacuCap filter, reaction flask was washed with water (100 mL). The polymer solution was concentrated to 40 mL by TFF (10 K) and was washed with 25 mM NaCl (800 mL) to remove p-nitrophenol, the pH was then adjusted to 4 with 0.1 M HCl and finally washed with water (400 mL). The pure polymer solution was lyophilized to isolate poly[HPMA-co-MA-GFLG-NH-2-[2-(2-aminoethoxy)ethoxy]ethylamine-HCl] as a pink solid (800 mg, 78%).

To a mixture of p-nitrophenyl fumagill-6-yl carbonate (93 mg, 0.208 mmol) and poly[HPMA-co-MA-GFLG-N-2-[(2-(2-aminoethoxy)]ethoxy)ethylamine-HCl] (200 mg, 0.104 mmol) in anhydrous DMF (5 mL) at 0° C. under N$_2$ was added DIEA (57 mg, 0.416 mmol). The reaction mixture was allowed to warm to room temperature and stirred for 12 hours. The solvent was removed under reduced pressure and the resulting residue was suspended in water (30 mL) and extracted with EtOAc (aqueous and organic phases from the emulsion formed were separated using centrifuge) to remove excess of p-nitrophenyl fumagill-6-yl carbonate and p-nitrophenol. Nitrogen was passed through the aqueous solution to remove traces of EtOAc and it was purified using TFF (5K) by washing it with water (150 mL) to remove DIEA hydrochloride. The polymer solution was lyophilized to obtain the desired polymer conjugate poly[HPMA-co-MA-GFLG-N-2-[2-(2-aminoethoxy)ethoxy ethyl] carbamoylfumagillol] (220 mg, 95%) as an off-white solid.

Example 34. Synthesis of poly[HPMA-co-MA-GFLG-NH-(6-aminodecyl)carbamoylfumagillol]

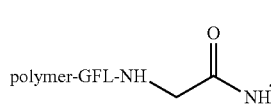

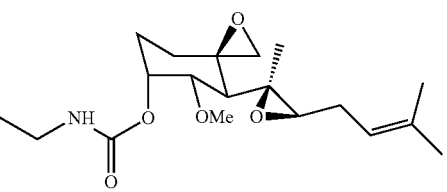

To a mixture of p-nitrophenyl fumagill-6-yl carbonate (300 mg, 0.67 mmol) and poly[HPMA-co-MA-GFLG-N-10-[decylamine-HCl] (300 mg, 0.15 mmol; made in a similar manner to Example 33 except 1,10-diaminodecane was used as the amine) in anhydrous DMF (6 mL) at 0° C. under N$_2$ was added DIEA (83 mg, 0.64 mmol). The reaction mixture was allowed to warm to room temperature and stirred for 12 hours. The solvent was removed under reduced pressure and the resulting residue was suspended in water (30 mL) and extracted with EtOAc (aqueous and organic phases from the emulsion formed were separated using a centrifuge) to remove excess of p-nitrophenyl fumagill-6-yl carbonate and p-nitrophenol. Nitrogen was passed through the aqueous solution to remove traces of EtOAc. The crude aqueous solution was purified using TFF (10K) by washing with water (150 mL) to remove DIEA hydrochloride. The polymer solution was lyophilized to obtain the desired polymer conjugate poly[HPMA-co-MA-GFLG-NH-(10-aminodecyl)carbamoylfumagillol] (300 mg, 87%) as an off-white solid.

Example 35. Synthesis of N-(2-acetamidoethyl)carbamoylfumagillol

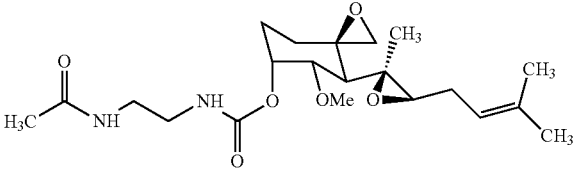

To a solution of p-nitrophenyl fumagill-6-yl carbonate (200 mg) in ethanol (5 mL) at 0° C. was added N-(2-aminoethyl)acetamide (0.132 mL). The solution was stirred at 0° C. for one hour and overnight at room temperature. The reaction was diluted with ethyl acetate, washed with water. The aqueous phase was back extracted with ethyl acetate and the combined organic phases dried (MgS)$_4$). The crude product was purified by flash chromatography. The product was a yellow solid (120 mg).

Example 36. Lysine Conjugate of Polymer and Met AP 2 Inhibitor Moiety

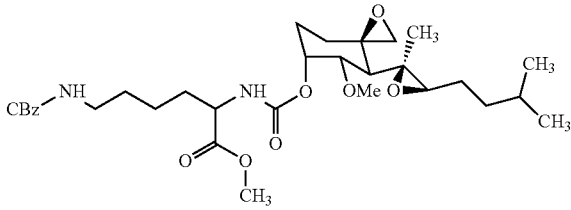

To a solution of p-nitrophenyl fumagill-6-yl carbonate (400 mg) and N-ε-Cbz-O-methyl-L-lysine hydrochloride in DMF (10 mL) at 0° C. was added DIEA (350 mg). The reaction was warmed to room temperature and the stirred overnight. The solution was diluted with ethyl acetate, washed with 0.1 N NaOH (4×), water, and then brine. The organic phase was dried (Na$_2$SO$_4$), filtered and evaporated. The residue was purified by flash chromatography (silica; methanol/methylene chloride) to provide the N-ε-Cbz-O-methyl-lysine-carbonylfumagillol (550 mg).

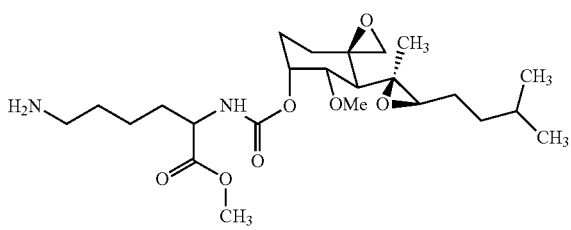

To a solution of N-ε-Cbz-O-methyl-lysine-carbonylfumagillol (200 mg) in ethyl acetate (10 mL) was added PtO2 monohydrate (20 mg) and the solution hydrogenated at STP for 20 minutes. Reduction of the double bond but not deprotection of the Cbz was verified by MS. The solution was filtered and evaporated. The residue was dissolved in methanol (10 mL) and 10% Pd/C (20 mg) was added. The solution was hydrogenated under STP for 5 minutes, and removal of the Cbz group confirmed by MS. The solution was filtered with celite, and evaporated to provide O-methyl-L-Lys-carbonyldihydrofumagillol as a colorless oil (0.15 g).

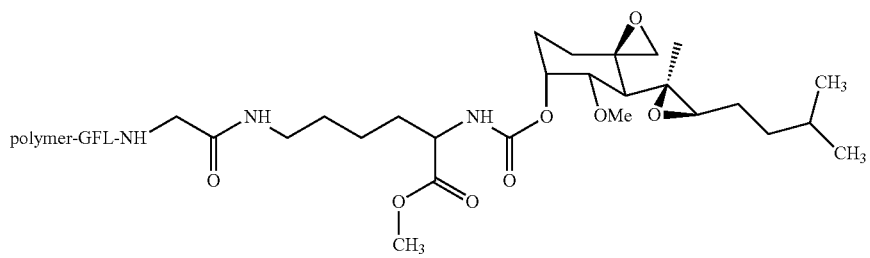

To a stirred solution of O-methyl-L-Lys-carbonyldihydrofumagillol (150 mg, 0.32 mmol) in DMF (6 mL) was added poly(HPMA-co-MA-GFLG-ONp) (300 mg) at 0° C. The resulting yellow solution was allowed to warm to room temperature overnight. The solvent was evaporated and the residue suspended in water (30 mL). The suspension was extracted six times with ethyl acetate (total ethyl acetate volume=150 mL). The aqueous phase was lyophilized to provide the polymer conjugate as a white solid (180 mg, 63%).

Example 37. Aminothiophenol Conjugate of Polymer and Met AP 2 Inhibitor Moiety

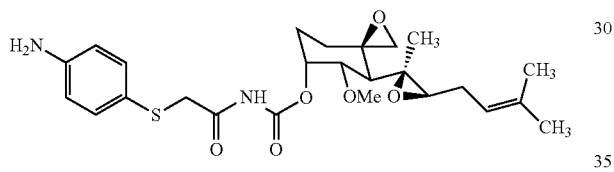

To a solution of chloroacetylcarbamoylfumagillol (500 mg) and 4-aminothiophenol (180 mg) in DMF (10 mL) at 0° C. was added DIEA (193 mg). The solution was stirred at 0° C. for 1.5 hours and then at room temperature overnight. The solution was diluted with water and extracted with ethyl acetate. Purification by flash chromatography (MeOH/CH$_2$Cl$_2$) followed by a second chromatography (EtOAc/hexanes) gave 4-aminophenylthioacetylcarbamoylfumagillol (460 mg).

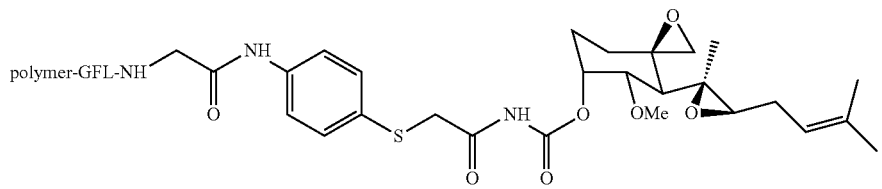

To a solution of poly(HPMA-co-MA-GFLG-ONp) (200 mg) and 4-aminophenylthioacetylcarbamoylfumagillol (100 mg) in DMF (5 mL) at 0° C. was added DIEA (106 mg). The solution was allowed to warm to room temperature and then heated to 50° C. and stirred overnight. The solvent was evaporated and the residue suspended in water. The suspension was extracted with ethyl acetate (150 mL). The aqueous phase was lyophilized to yield the polymer conjugate as a white solid (180 mg).

Example 38

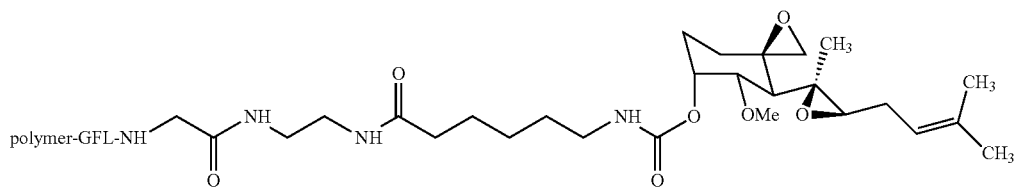

To a solution of poly(HPMA-co-MA-GFLG-NHCH$_2$CH$_2$NH$_2$HCl) (200 mg) and N-(5-carboxypentyl)carbamoylfumagillol (96 mg) in DMF (6 mL) at 0° C. was added DIEA (104 mg) followed by N-(3-dimethylaminopropyl)-N'-ethylcarbodiimide hydrochloride (42 mg). The solution was allowed to warm to RT and stirred overnight. The solvent was evaporated and the residue dissolved in water (50 mL) and extracted with ethyl acetate (200 mL). The aqueous phase was purified by TFF with water (450 mL). The retentate was lyophilized to yield the polymer (200 mg) as a pale yellow solid.

Example 39

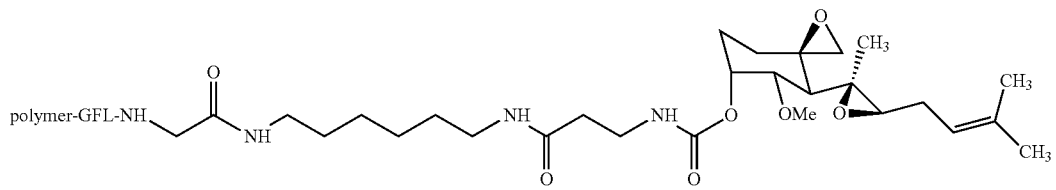

To a solution of poly[HPMA-co-MA-GFLG-N(CH$_2$)$_6$NH$_2$ HCl] (216 mg), 2-carboxyethylcarbamoylfumagillol (91 mg) in DMF (8 mL) at 0° C. was added DIEA (118 mg) followed by N-(3-Dimethylaminopropyl)-N'-ethylcarbodiimide hydrochloride (88 mg). The solution was allowed to warm to room temperature and stirred overnight. The solvent was evaporated and the residue dissolved in water (50 mL) and extracted with ethyl acetate (200 mL). The aqueous phase was purified by TFF (10 K) with water (1 L). The retentate was lyophilized to yield the polymer (170 mg) as a pale yellow solid.

Example 40

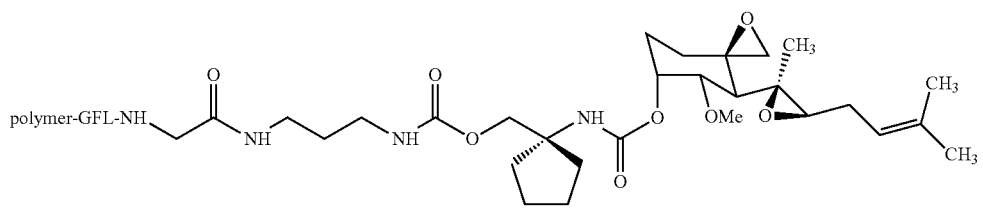

General Procedure F was followed using poly(HPMA-co-MA-GFLG-NHCH$_2$CH$_2$CH$_2$NH$_2$HCl) (220 mg) and carbonate (Example 24, 100 mg) in DMF (6 mL) with DIEA (63 mg). The reaction was extracted with ethyl acetate. Following TFF (10 K) purification with water, and lyophilization, the product was isolated as a light pink powder (140 mg).

Example 41

General Procedure F was followed using poly(HPMA-co-MA-GFLG-NHCH$_2$CH$_2$CH$_2$NH$_2$HCl) (200 mg) and carbonate (Example 23, 86 mg) in DMF (5 mL) with DIEA (57 mg). Extraction was performed with ethyl acetate. Following TFF purification with water, and lyophilization, the product was isolated as a light pink powder (200 mg).

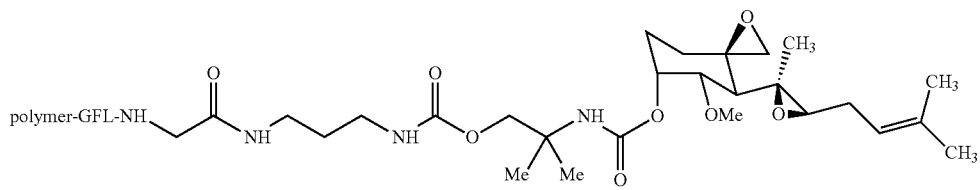

Example 42. Synthesis of poly[HPMA-co-MA-GFLG-N-(6-aminohexyl)acetamide]

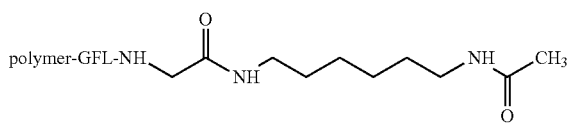

To a solution of aminohexylpolymer (600 mg) and p-nitrophenyl acetate (110 mg) in DMF (16 mL) at 0° C. was added DIEA dropwise. The solution was allowed to warm to room temperature and stirred overnight. The solvent was evaporated and the residue was dissolved in water (50 mL), filtered through a vacu-cap filter with an additional 25 mL of water. The pH was adjusted to 8.0 with 0.1 M NaOH and the solution concentrated to 50 mL (TFF). The retentate was washed with aqueous NaCl (25 mM, 450 mL) until the permeate was almost colorless and then washed with water (400 mL) to a conductivity of 0.00 uS. The retentate was lyophilized to yield 0.59 g of a pink solid.

Example 43. Aqueous Stability of Carbamoylfumagillol

A stock solution of carbamoylfumagillol in DMSO was diluted in a 15 mL polypropylene screw top tube with either 5 mL of 10 mM sodium acetate buffer at either pH 4.0 or 5.3, or potassium phosphate buffer at pH 6.7 or 8.0 at 37° C. The final concentration of carbamoylfumagillol in the buffer solution was 5 μM. At the appropriate time points, a 50 μL sample was withdrawn and diluted with three volumes of methanol containing propranolol as an internal standard (one solution was made for the entire study). The concentration of carbamoylfumagillol in the solution was analyzed by LC/MS/MS over seven days. From pH 5.3 to 8.0, less than 20% decomposition was observed over the seven day period. Estimated rate constants are presented in Table 1.

TABLE 1

Natural Rate Constant of Carbamoylfumagillol after Incubation 37° C. in Aqueous Buffer at Various pHs

| pH | Natural Rate Constant ($hr^{-1}$) | T ½ (hr) |
|---|---|---|
| 4.0 | 0.0054 | 129 |
| 5.3 | 0.0017 | *407* |
| 6.7 | 0.0010 | *728* |
| 8.0 | 0.0011 | *613* |

*the values in italics are approximate as the decompositions did not reach 50% in 168 hours
** The half life is calculated as ln(2)/rate constant.

Example 44. Water in Polymer Conjugates

Selected polymers were analyzed by Karl Fisher (QTI Salem Industrial Park—Bldg. #5 Whitehouse, N.J. 08888) to determine the water content of the polymer. The results are summarized below in Table 2.

TABLE 2

| Sample | Water Constant % |
|---|---|
| O-7175 | 6.56 |
| O-7320 | 9.65 |
| O-7271 | 6.71 |
| O-7376 | 5.13 |

Example 45. Reaction of Carbamoylfumagillol with 2-Mercaptopyrimidine

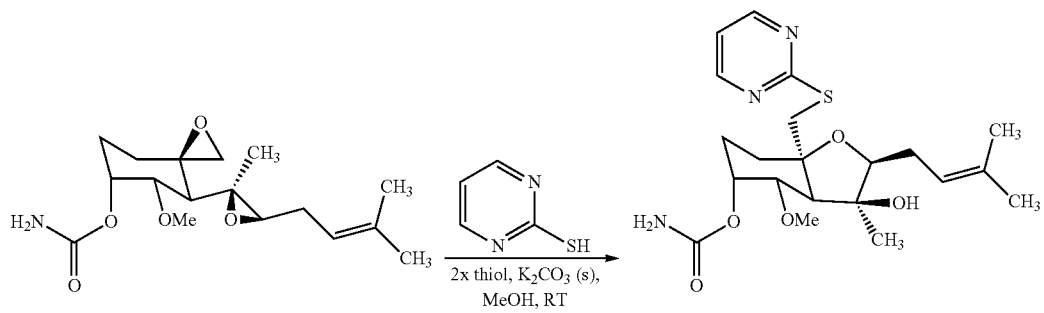

A stock solution, 1 mg/mL, of 2-mercaptopyrimidine (2.2 mL) in methanol-D4 was added to carbamoylfumagillol (6.4 mg). One mL of the resulting solution was removed and a second portion of the stock solution was added (1 mL). Solid $K_2CO_3$ was added and the solution monitored by $^1$H NMR. A single product was identified, the 1:1 adduct of 2-mercaptopyrimidine and carbamoylfumagillol.

The following resonances were used to monitor the reaction by $^1$H NMR:

2-Mercaptopyrimidine showed resonances at 6.7 ppm (lH, H-4) and 8.1 ppm (2H, H-3, H-5).

The adduct of 2-mercaptopyrimidine showed resonances at 7.2 ppm (1H, H-4) and 8.5-8.6 ppm (2H, H-3, H-5).

Example 46. Reaction of Polymer Conjugates with 2-Mercaptopyrimidine

A stock solution, 1 mg/mL, of 2-mercaptopyrimidine (1.1 mL) in methanol-D4 was added to the polymer conjugate (10 mg). The solution was stirred at room temperature overnight, and analyzed by $^1$H NMR to determine the ratio of unreacted thiol (8.1 ppm) to reacted thiol (8.5-8.6 ppm). The amount of reacted thiol was expected to be equivalent to the quantity of fumagillol in the polymer conjugate. The acetamide capped polymer containing no epoxide showed no reaction product with 2-mercaptopyrimidine as indicated in Table 3.

TABLE 3

| Sample | Reacted thiol/g polymer |
|---|---|
| O-7175 | 0.37 mmols/g |
| O-7320 | 0.37 mmols/g |
| O-7376 | <0.001 mmols/g |

Example 47. Cathepsin B Release of Fumagillol Analogs

Cathepsin B (Sigma Cat# C6286 Lot#025K7672) was diluted to a 10× concentration in activation buffer consisting of approximately 400 nM enzyme, 30 mM DTT, 15 mM EDTA and acetate buffer, pH=5.5 for 15 minutes at room temperature.

The HPMA conjugates were made into a 10× stock solution in pH 5.5 buffer. The final reaction was performed by diluting the enzyme and substrate 10 fold into either buffer at pH=5.5 or pH=6.8. The final enzymatic reaction consisted of 40 nM Cathepsin B, approximately 2.5 mg/mL test agent, and buffer at 37° C. The reaction was stopped at 0, 2, 6, and 24 hour. To stop the reaction, 3 volumes of ice-cold methanol containing propranolol internal standard (at 1.0 µM) was added and left on ice. The samples were then analyzed by LC/MS/MS.

Poly[HPMA-co-MA-GFLG-N-(6-aminohexyl)carbamoylfumagillol] was shown to release N-(6-aminohexyl)carbamoylfumagillol and fumagil-6-yl {6-[(aminoacetyl)amino]hexyl} carbamate.

Poly(HPMA-co-MA-GFLG-NHCH$_2$CH$_2$N(Me)CH$_2$C(O)NHC(O)$_2$-fumagill-6-yl) was shown to release fumagillol, carbamoylfumagillol, and fumagil-6-yl (2-aminoethyl)methylcarbamate.

Poly(HPMA-co-MA-GFLG-N(Me)CH$_2$CH$_2$N(Me)CH$_2$C(O)NHC(O)$_2$-fumagill-6-yl) was shown to release fumagillol, carbamoylfumagillol, fumagil-6-yl methyl[2-(methylamino)ethyl]carbamate, and ethyl {2-[(aminoacetyl)(methyl)amino]ethyl}methylcarbamate.

Example 48. General Materials and Methods for In Vitro Analysis

Test compounds, small molecules or polymer conjugates, were dissolved in dimethyl sulfoxide to a stock concentration of 5 mg/mL. The test agents were then diluted to an intermediate concentration at 200 µg/mL in 10% DMSO. Further dilutions were completed serially 3-fold in 10% DMSO to produce 12 decreasing concentrations for in-vitro analysis. To achieve the target concentrations of the in-vitro assays, 1 of the intermediate drug preparation was delivered to the cells (seeded in a volume of 50 µL). The final DMSO concentration for the tests was 0.2% for all doses of test agent.

Cells were exposed to twelve increasing concentrations of formulated test agent from $2 \times 10^{-6}$ to 4.0 µg/mL for 72 hours. Following 72 hour exposure, 25 µL of CellTiter-Glo® Reagent was added to each well. The plates were incubated for 60 minutes at 37° C. in a humidified incubator. After incubation, luminescence was recorded using the Molecular Devices AnalystGT multi-mode reader.

IC50 Determination

Data are expressed as the percent cell growth of the untreated (vehicle) control calculated from the luminescence signals. The surviving fraction of cells is determined by dividing the mean luminescence values of the test agents by the mean luminescence values of untreated control. The inhibitory concentration value for the test agent(s) and control were estimated using Prism 5 software (GraphPad Software, Inc.) by curve-fitting the data using the non-linear regression analysis.

Example 49. A549 Human Non-Small Cell Lung Carcinoma Cell Viability Assay

The human tumor cell lines A549 and HCT-116 were obtained from American Type Culture Collection (Manassas, Va.). The Human umbilical vein epithelial cells (HUVEC) were obtained from Lonza (Basel, Switzerland). The A549 cells were maintained RPMI 1640 w/L-glut supplemented with 5% FBS. The HCT-116 cells were maintained in McCoy's 5a supplemented with 5% FBS. The HUVEC line was grown in Endothelial Growth Medium with supplements and growth factors (BBE, hydrocortisone, hEGF, FBS and gentamicin/amphotericin-B). All cells were house in an atmosphere of 5% $CO_2$ at 37° C. Cells were dissociated with 0.05% Trypsin and 0.02% EDTA.

The human tumor cell line A549 was obtained from American Type Culture Collection (Manassas, Va.). The A549 cells were maintained RPMI 1640 w/L-glut supplemented with 5% FBS. A549 cells were seeded at 500 cells per well 24 hours prior to test agent exposure in a volume of 50 µL. The cells were housed in an atmosphere of 5% $CO_2$ at 37° C. Cells were dissociated with 0.05% Trypsin and 0.02% EDTA.

TABLE 4

A549—Small Molecules
Table 4

| Compound | A549 IC50 Average ng/mL | Compound # |
|---|---|---|
|  | 0.508 | O-7233 |
|  | 0.777 | O-7299 |
|  | 1.50 | O-7322 |
|  | 5.99 | O-7319 |
|  | 23.2 | O-7287 |
|  | 0.215 | O-7177 |
|  | 1.06 | O-7216 |
| Carbamoylfumagillol | 2.89 | O-7127-1 |
| TNP-470 | 8.97 | O-7178 |
| Fumagillol | 30.1 | O-7126-1 |

TABLE 5

549—Polymer Conjugates
Table 5

| Compound | A549 IC50 Average ng/mL | Compound # |
|---|---|---|
|  | 0.86 | O-7172 |
|  | 1.08 | O-7173 |
|  | 0.40 | O-7174 |
|  | 0.50 | O-7175 |
|  | 2.57 | O-7176 |
|  | 1.11 | O-7192 |
|  | 0.28 | O-7193 |
|  | 1.12 | O-7195 |
|  | 0.67 | O-7196 |
|  | 0.12 | O-7215 |
|  | 0.52 | O-7232 |
|  | 0.40 | O-7234 |
|  | 1.16 | O-7271 |
|  | 0.08 | O-7272 |
|  | 0.17 | O-7303 |
|  | 0.42 | O-7304 |
|  | 4.00 | O-7305 |
|  | 0.89 | O-7306 |
|  | 0.32 | O-7320 |
|  | 0.42 | O-7321 |
|  | 0.98 | O-7323 |
|  | 1.54 | DRS-226-46E |

Example 50. HCT-116 Human Colon Tumor Cell Viability Assay

The human tumor cell lines A549 and HCT-116 were obtained from American Type Culture Collection (Manassas, Va.). The HCT-116 cells were maintained in McCoy's 5a supplemented with 5% FBS. HCT-116 cells were seeded at 500 cells per well 24 hours prior to test agent exposure in a volume of 50 µL. The cells were housed in an atmosphere of 5% $CO_2$ at 37° C. Cells were dissociated with 0.05% Trypsin and 0.02% EDTA.

Cells were exposed to twelve increasing concentrations of formulated test agent from $2.3 \times 10^{-6}$ to 4.02 µg/mL for 72 hours. Following 72 hour exposure, 25 µL of CellTiter-Glo® Reagent was added to each well. The plates were incubated for 60 minutes at 37° C. in a humidified incubator. After incubation, luminescence was recorded using the Molecular Devices AnalystGT multi-mode reader.

TABLE 6

HCT116—Small Molecules
Table 6

| Compound | HCT116 IC50 Average ng/mL | Compound # |
|---|---|---|
|  | 0.236 | O-7177 |
|  | 0.408 | O-7194 |
|  | 0.918 | O-7216 |
| Carbamoylfumagillol | 1.035 | O-7127-1 |
| TNP-470 | 2.64 | O-7178 |
| Fumagillol | 45.8 | O-7216-1 |

TABLE 7

HCT116—Polymer Conjugates
Table 7

| Compound | HCT116 IC50 Average ng/mL | Compound # |
|---|---|---|
|  | 0.157 | O-7215 |
|  | 0.329 | O-7193 |
|  | 0.392 | O-7174 |
|  | 0.626 | O-7175 |
|  | 0.818 | O-7196 |
|  | 1.221 | O-7172 |
|  | 1.051 | O-7173 |
|  | 1.184 | O-7192 |
|  | 1.203 | O-7195 |
|  | 0.984 | DRS-226-46E |
|  | 5.954 | O-7176 |

Example 51. Human Umbilical Vein Epithelial Cell Viability Assay

The Human umbilical vein epithelial cells (HUVEC) were obtained from Lonza (Basel, Switzerland). The HUVEC line was grown in Endothelial Growth Medium with supplements and growth factors (BBE, hydrocortisone, hEGF, FBS and gentamicin/amphotericin-B). All cells were housed in an atmosphere of 5% $CO_2$ at 37° C. Cells were dissociated with 0.05% Trypsin and 0.02% EDTA.

HUVEC cells were seeded at 1000 cells per well 24 hours prior to test agent exposure in a volume of 50 µE. Cells were exposed to twelve increasing concentrations of formulated test agent from $2.3 \times 10^{-6}$ to 4.02 µg/mL for 72 hours. Following 72 hour exposure, 25 of CellTiter-Glo® Reagent was added to each well. The plates were incubated for 60 minutes at 37° C. in a humidified incubator. After incubation, luminescence was recorded using the Molecular Devices AnalystGT multi-mode reader.

TABLE 8

HUVEC—Small Molecules
Table 8

| Compound | HUVEC IC50 Average ng/mL | Compound # |
|---|---|---|
|  | 0.101 | O-7177 |
|  | 0.120 | O-7194 |
|  | 0.209 | O-7216 |
| Carbamoylfumagillol | 0.086 | O-7127-1 |
| TNP-470 | 0.153 | O-7178 |
| Fumagillol | 18.9 | O-7126-1 |

TABLE 9

HUVEC—Polymer Conjugates
Table 9

| Compound | HUVEC IC50 Average ng/mL | Compound # |
|---|---|---|
|  | 0.157 | O-7215 |
|  | 0.329 | O-7193 |
|  | 0.392 | O-7174 |
|  | 0.626 | O-7175 |
|  | 0.818 | O-7196 |
|  | 1.221 | O-7172 |
|  | 1.051 | O-7173 |
|  | 1.184 | O-7192 |
|  | 1.203 | O-7195 |
|  | 0.984 | DRS-226-46E |
|  | 5.954 | O-7176 |

Example 52. A549/HUVEC Selectivity

The ratio of the HUVEC IC50/A549 $IC_{50}$ is presented in Table 10 below. When compared to carbamoylfumagillol and TNP-470, the polymer conjugates are more active against the tumor cells, A549, than against the normal HUVEC cells.

TABLE 10

| Compound | A549/HUVEC IC50 | Compound # |
|---|---|---|
| IC50 ratio | | |
|  | 2.14 | O-7177 |
|  | 2.97 | O-7194 |
|  | 5.06 | O-7216 |
| Carbamoylfumagillol | 33.63 | O-7127-1 |
| TNP-470 | 58.53 | O-7178 |
| Fumagillol | 1.59 | O-7126-1 |
| Polymer Conjugates | | |
|  | 0.66 | O-7215 |
|  | 3.13 | O-7193 |

TABLE 10-continued

| Compound | A549/HUVEC IC50 | Compound # |
|---|---|---|
|  | 2.04 | O-7174 |
|  | 2.64 | O-7175 |
|  | 2.26 | O-7196 |
|  | 1.52 | O-7172 |
|  | 1.30 | O-7173 |
|  | 1.81 | O-7192 |
|  | 1.66 | O-7195 |
|  | 4.33 | DRS-226-46E |
|  | 0.98 | O-7176 |

Example 53. A549 Metabolites

Cells were treated as in Example 51 except that at the end of 72 hour exposure to test agent, the cells were frozen (−70° C.) and stored for subsequent evaluation by LC/MS. Metabolites identified from the cells treated with poly [HPMA-co-MA-GFLG-N-(6-aminohexyl)carbamoylfumagillol] include N-(6-aminohexyl)carbamoylfumagillol, fumagill-6-yl {6-[(aminoacetyl)amino]hexyl}carbamate, and the epoxide hydrolysis product, (3S',7aR)-7a-(hydroxymethyl)-4-methoxy-3-methyl-2-(3-methylbut-2-en-1-yl)octahydro-1-benzofuran-3-ol-5-yl 6-aminohexyl carbamate.

Example 54. In Vivo Testing B16-F10 Murine Melanoma

C57B16 female mice (N=8) were injected (tail vein) with $1 \times 10^5$ B16-F10 tumor cells. After one day, mice were treated with polymer conjugates as solutions in saline (IV administration, q4d, four doses except that in one group O-7175 was administered as a single dose on day 1). TNP-470 was used as a positive control, saline as a negative control. Mice were sacrificed after 15 days. Treatment outcomes were assessed by counting lung metastases.

TABLE 11

Metastases Counts
Table 11

| Group | Dose mg/kg* | Metastases Counts |
|---|---|---|
| Saline control | 0 | 36.8 |
| TNP-470 | 30 | 39.5 |
| O-7175 | 50 | 17.0 |
| O-7175 | 100 | 24.5 |
| O-7175 | 200 | 20.9 |
| O-7320 | 200 | 7.6 |
| O-7271 | 200 | 20.0 |
| O-7215 | 200 | 32.5 |
| O-7175 | 1000 | 10.1 |

*All groups, N = 8. IV dosing q4d, days 1, 5, 9 and 13 except TNP-470 (qod) and O-7175 at 1000 mg/kg (single dose on day 1).

Example 55. In Vivo Testing C57B16 Mice—Weight Changes

C57B16 female mice (N=8) were injected (tail vein) with $1 \times 10^5$ B16-F10 tumor cells. After one day, mice were treated with polymer conjugates as solutions in saline (IV administration, q4d, four doses). The weight changes for three polymers relative to saline vehicle control and TNP-470 are shown in FIG. 1. Weight changes are referenced to the group weight at time zero. All polymers were dosed at 100 mg/kg. Polymer doses and the saline vehicle were administered on days 1, 5, and 9. The 100 mg/kg polymer doses and TNP-470 showed a reduction in metastases from 44-63% relative to the saline control.

Example 56. In Vivo Testing C57B16 Mice Weight Changes

Figure 2:
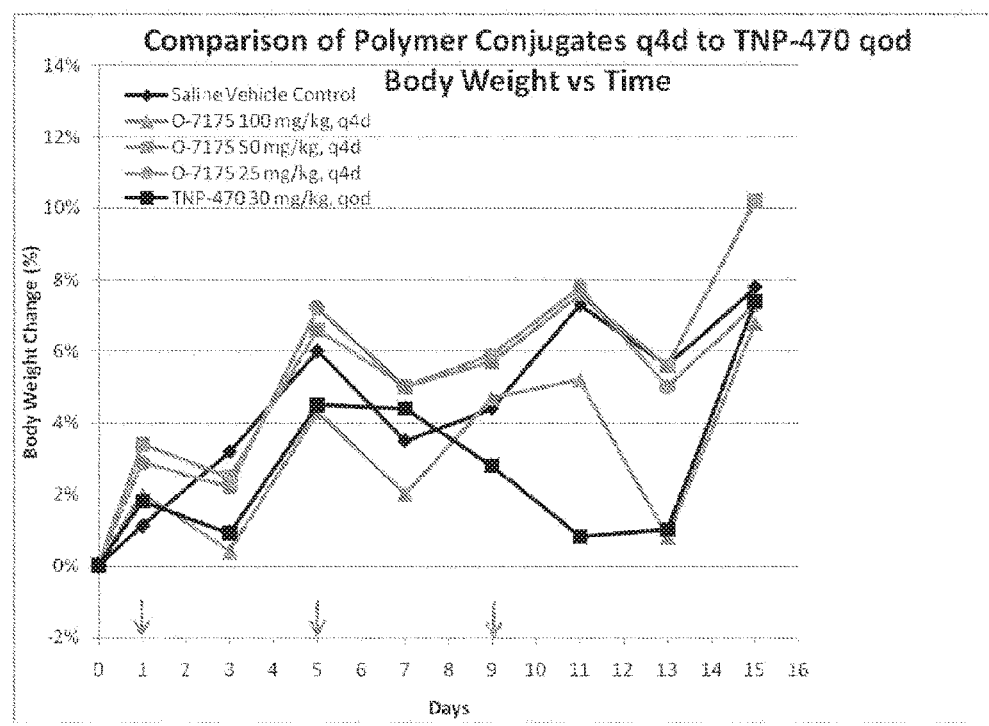
FIG. 2 shows percentage weight change as a function of time for C57Bl/6 mice, injected initially with B16-F10 tumor cells (1×10$^5$), to which a polymer conjugate (dosed at 100, 50 and 25 mg/kg, q4d) has been administered. Comparative data are included for TNP-470 (dosed at 30 mg/kg, qod) and saline control.

C57B16 female mice (N=8) were injected (tail vein) with $1 \times 10^5$ B16-F10 tumor cells. After one day, mice were treated with polymer conjugates as solutions in saline (IV administration, q4d, four doses). The weight changes for one polymer at three different doses relative to control are shown in FIG. 2. Weight changes are referenced to the group weight at time zero. The polymer doses were 50 mg/kg, or 100 mg/kg. Polymer doses were administered on days 1, 5, and 9. The 25, 50 and 100 mg/kg polymer doses and TNP-470 showed a reduction in metastases from 45-61% relative to the saline control.

Example 57. In Vivo Testing nu/nu Mice—A 549 Xenograft

Figure 3:
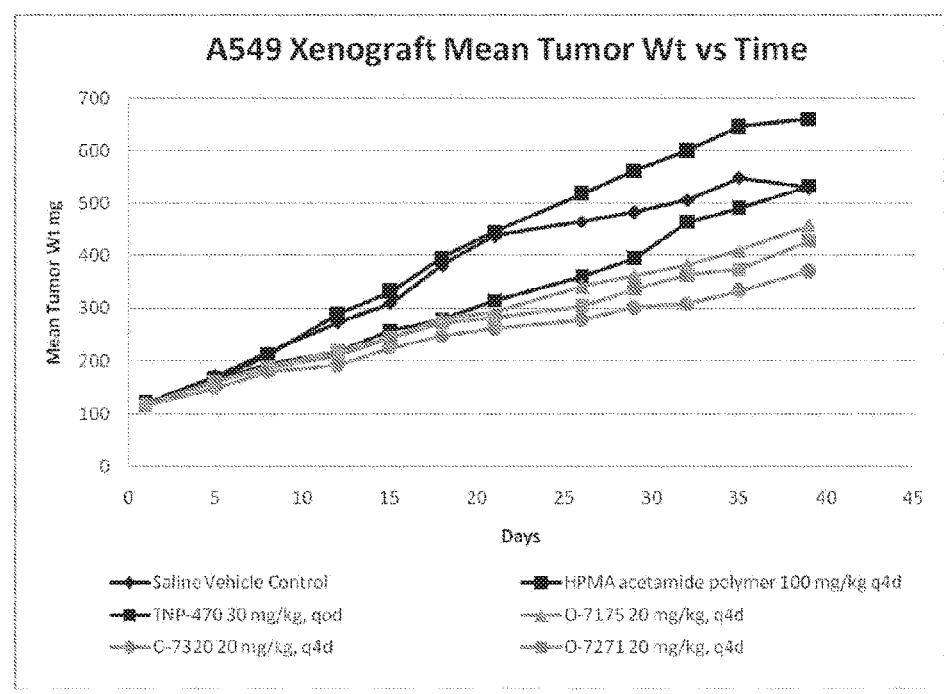
FIG. 3 shows the change in tumor size as a function of time for nu/nu mice, injected initially with A549 tumor cells, to which one of three polymer conjugates (dosed at 20 mg/kg, q4d) has been administered. Comparative data are included for TNP-470 (30 mg/kg, qod), a polymer without drug (100 mg/kg, q4d) and saline control.

Nu/nu female mice (N=8) were injected (subcutaneous right flank) with $5 \times 10^6$ A549 tumor cells (inoculation vehicle 50% media/matrigel, subcutaneous right flank). After the tumors reached a size of 116 mg, mice were treated with polymer conjugates as solutions in saline (20 mg/kg, IV administration, q4d, six doses) or with a control polymer without a MetAP2 inhibitory moiety (100 mg/kg, q4d) or with TNP-470 (30 mg/kg, qod, nine doses). Tumor growth was determined by measuring tumor size in two directions with calipers at intervals of a few days. The tumor size vs time is shown in FIG. 3. The doses used are summarized in the table below.

TABLE 12

|  | Schedule | # doses | Single Dose mg/kg | Total Dose mg | Total Dose mmol active |
|---|---|---|---|---|---|
| TNP-470 | qod | 9 | 30 | 270 | 0.67 |
| Polymer | Q4d | 6 | 20 | 120 | 0.044 |
|  | frequency | # doses | wt/wt | wt/wt | mol/mol |
| Polymer % | 50% | 67% | 67% | 44% | 7% |

Figure 4:
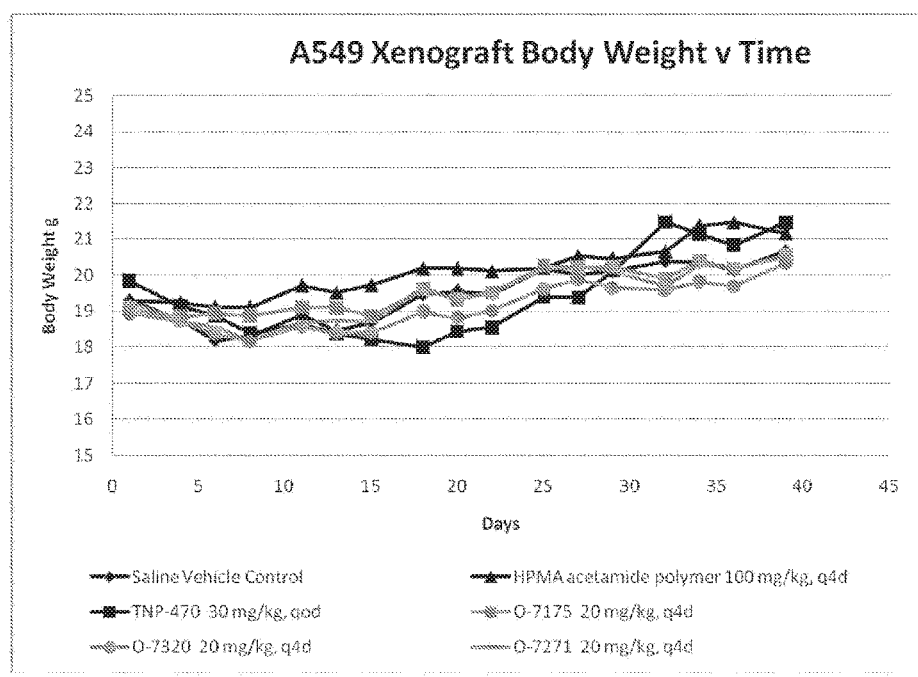
FIG. 4 shows the change in body weight change as a function of time for nu/nu mice, injected initially with A549 tumor cells, to which one of three polymer conjugates (dosed at 20 mg/kg, q4d) has been administered. Comparative data are included for TNP-470 (30 mg/kg, qod), a polymer without drug (100 mg/kg, q4d) and saline control.

The change in body weight vs time for the A549 Xenograft experiment is shown in FIG. 4. The mice in the active polymer treated groups show similar weight changes to the TNP-470 group and the control groups.

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:
1. A pharmaceutical composition comprising the compound:

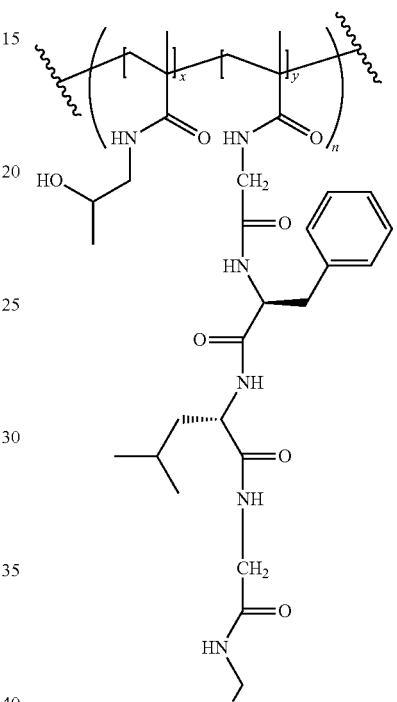

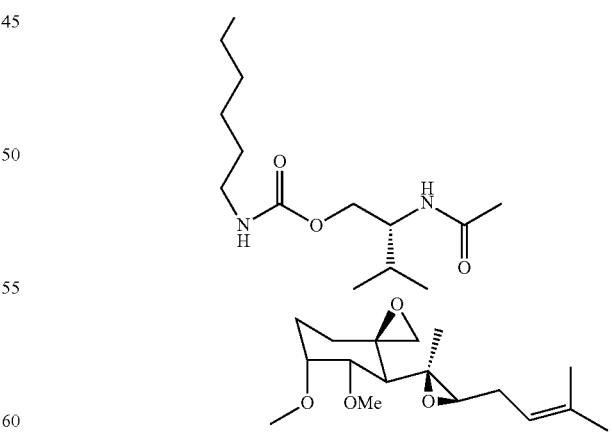

wherein x is between 1 and about 450, y is between 1 and about 30, and n is between 1 and about 50; and
a pharmaceutically acceptable carrier.
2. A pharmaceutical composition comprising the compound:

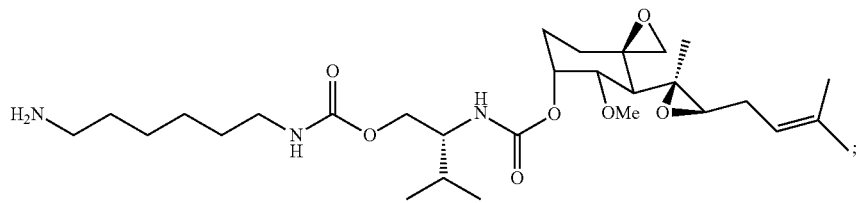
and
a pharmaceutically acceptable carrier.